(12) United States Patent
Chen et al.

(10) Patent No.: US 11,987,560 B2
(45) Date of Patent: *May 21, 2024

(54) INHIBITORS OF LYSINE SPECIFIC DEMETHYLASE-1

(71) Applicant: CELGENE QUANTICEL RESEARCH, INC., San Diego, CA (US)

(72) Inventors: Young K. Chen, San Marcos, CA (US); Toufike Kanouni, Rancho Santa Fe, CA (US); Stephen W. Kaldor, San Diego, CA (US); Jeffrey Alan Stafford, San Diego, CA (US); James Marvin Veal, Apex, NC (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/356,389

(22) Filed: Jun. 23, 2021

(65) Prior Publication Data

US 2022/0153706 A1 May 19, 2022

Related U.S. Application Data

(63) Continuation of application No. 16/841,595, filed on Apr. 6, 2020, now Pat. No. 11,084,793, which is a continuation of application No. 16/007,937, filed on Jun. 13, 2018, now Pat. No. 10,654,810, which is a continuation of application No. 15/687,251, filed on Aug. 25, 2017, now Pat. No. 10,023,543, which is a continuation of application No. 15/401,894, filed on Jan. 9, 2017, now Pat. No. 9,776,974, which is a continuation of application No. 14/988,022, filed on Jan. 5, 2016, now Pat. No. 9,573,930, which is a continuation of application No. 14/701,304, filed on Apr. 30, 2015, now Pat. No. 9,255,097.

(60) Provisional application No. 61/987,354, filed on May 1, 2014.

(51) Int. Cl.
| | |
|---|---|
| C07D 239/47 | (2006.01) |
| A61K 31/4545 | (2006.01) |
| A61K 31/513 | (2006.01) |
| A61K 31/5377 | (2006.01) |
| A61K 31/551 | (2006.01) |
| C07B 59/00 | (2006.01) |
| C07D 239/36 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| C07D 405/14 | (2006.01) |
| C07D 471/10 | (2006.01) |

(52) U.S. Cl.
CPC ........ *C07D 239/47* (2013.01); *A61K 31/4545* (2013.01); *A61K 31/513* (2013.01); *A61K 31/5377* (2013.01); *A61K 31/551* (2013.01); *C07B 59/002* (2013.01); *C07D 239/36* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/14* (2013.01); *C07D 471/10* (2013.01); *C07B 2200/05* (2013.01)

(58) Field of Classification Search
CPC .. C07D 401/04; C07D 401/14; C07D 403/04; C07D 403/14; A61K 31/4545; A61K 31/506; A61K 31/513
See application file for complete search history.

(56) References Cited

U.S. PATENT DOCUMENTS

| | | |
|---|---|---|
| 5,550,147 A | 8/1996 | Matsua et al. |
| 7,037,918 B2 | 5/2006 | Nuss et al. |
| 7,767,669 B2 | 8/2010 | Nuss et al. |
| 8,980,879 B2 | 3/2015 | Liu et al. |
| 9,034,900 B2 | 5/2015 | Bennett et al. |
| 9,255,097 B2 | 2/2016 | Chen et al. |
| 9,573,930 B2 | 2/2017 | Chen et al. |
| 9,771,329 B2 * | 9/2017 | Chen ..................... C07B 59/002 |
| 9,776,974 B2 | 10/2017 | Chen et al. |
| 9,828,358 B2 | 11/2017 | Chen et al. |
| 10,023,543 B2 | 7/2018 | Chen et al. |

(Continued)

FOREIGN PATENT DOCUMENTS

| | | |
|---|---|---|
| WO | WO 2004/048365 A1 | 6/2004 |
| WO | WO 2010/012740 A1 | 2/2010 |

(Continued)

OTHER PUBLICATIONS

Merck Manual Professional Online Edition, Acute Leukemia, 6 pages, 2013.*

(Continued)

*Primary Examiner* — Deepak R Rao
(74) *Attorney, Agent, or Firm* — Foley & Lardner LLP

(57) ABSTRACT

The present invention relates generally to compositions and methods for treating cancer and neoplastic disease. Provided herein are substituted heterocyclic derivative compounds and pharmaceutical compositions comprising said compounds. The subject compounds and compositions are useful for inhibition of lysine specific demethylase-1. Furthermore, the subject compounds and compositions are useful for the treatment of cancer.

4 Claims, No Drawings

(56) References Cited

U.S. PATENT DOCUMENTS

| | | | |
|---|---|---|---|
| 10,047,069 B2 | 8/2018 | Chen et al. | |
| 10,207,999 B2 * | 2/2019 | Chen | C07D 401/12 |
| 10,316,016 B2 | 6/2019 | Chen et al. | |
| 10,385,051 B2 | 8/2019 | Chen et al. | |
| 10,654,810 B2 * | 5/2020 | Chen | C07D 401/14 |
| 10,703,739 B2 | 7/2020 | Chen et al. | |
| 11,084,793 B2 * | 8/2021 | Chen | C07B 59/002 |
| 2004/0242608 A1 | 12/2004 | Durley | |
| 2007/0219210 A1 | 9/2007 | Kanaya et al. | |
| 2010/0048591 A1 | 2/2010 | Flynn et al. | |
| 2011/0201650 A1 | 8/2011 | Morita et al. | |
| 2013/0040929 A1 | 2/2013 | Hale et al. | |
| 2014/0011857 A1 | 1/2014 | Casero et al. | |
| 2016/0022684 A1 | 1/2016 | Kuo et al. | |
| 2016/0130247 A1 | 5/2016 | Chen et al. | |
| 2016/0152595 A1 | 6/2016 | Chen et al. | |
| 2017/0114024 A1 | 4/2017 | Chen et al. | |
| 2017/0349555 A1 | 12/2017 | Chen et al. | |
| 2017/0349556 A1 | 12/2017 | Chen et al. | |
| 2018/0325900 A1 | 11/2018 | Chen et al. | |
| 2020/0231549 A1 | 7/2020 | Chen et al. | |

FOREIGN PATENT DOCUMENTS

| | | |
|---|---|---|
| WO | WO 2012/135113 A2 | 10/2012 |
| WO | WO 2013/175789 A1 | 11/2013 |
| WO | WO 2015/018522 A1 | 2/2015 |
| WO | WO 2016/097870 A1 | 6/2016 |

OTHER PUBLICATIONS

Office Action issued in Brazilian Application No. 112016025248-9, dated Jul. 27, 2021.
Office Action issued in Ecuadorian Patent Application No. IEPI-2016-91608, dated Feb. 15, 2022.
Office Action issued in Mexican Patent Application No. MX/a/2016/007585, dated May 27, 2019.
Notice of Allowance issued in co-pending U.S. Appl. No. 16/166,832, dated Apr. 5, 2019.
Berge et al., Pharmaceutical Salts. Journal of Pharmaceutical Sciences 66(1):1-19 (Jan. 1977).
Bundgard et al., Design of Prodrugs, pp. 1-10, 21-24 (1985).
Han et al., Synergistic Re-Activation of Epigenetically Silenced genes by Combinatorial Inhibition of DNMTs and LSD1 in Cancer Cells. PLOS One 8(9):e75136 (2013).
Higuchi et al., Pro-drugs as Novel Delivery Systems, A.C.C. Symposium Series, vol. 14 (1975).
International Preliminary Report on Patentability dated, Nov. 10, 2016, cited in related International Application No. PCT/US2015/28635.
International Search Report and Written Opinion dated, Aug. 4, 2015, cited in related International Application No. PCT/US2015/28635.
Stahl et al., Handbook of Pharmaceutical Salts. Verlag Helvetica Chimica Acta, Zurich (2002).
Gura et al., Systems for identifying new drugs are often faulty, Science, 278:1041-1042, 1997.
Johnson, et al., Relationships between drug activity in NCI preclinical in vitro and in vivo models and early clinical trials, British Journal of Cancer, 84(10):1424-1431,2001.
Pearce, et al., Failure modes in anticancer drug discovery and development, Cancer Drug Design and Discovery Edited by Stephen Neidle, Chapter 18, pp. 424-435 (2008).
Simone, Oncology: Introduction, Cecil Textbook of Medicine, 20th Edition, vol. 1, pp. 1004-1010, 1995.
International Search Report and Written Opinion dated Jan. 11, 2018, in PCT/US2017/058614.
Extended European Search Report dated Dec. 12, 2017, cited in related EP Patent Application No. 15785884.5, filed Nov. 30, 2016, based on PCT/US2016/28635 (filed on Apr. 30, 2015).

* cited by examiner

INHIBITORS OF LYSINE SPECIFIC DEMETHYLASE-1

CROSS REFERENCE

This application is a continuation of U.S. patent application Ser. No. 16/841,595, filed Apr. 6, 2020, which is a continuation of U.S. patent application Ser. No. 16/007,937, filed Jun. 13, 2018, now U.S. Pat. No. 10,654,810, which is a continuation of U.S. application Ser. No. 15/687,251, now U.S. Pat. No. 10,023,543, filed Aug. 25, 2017, which is a continuation of U.S. application Ser. No. 15/401,894, filed Jan. 9, 2017, now U.S. Pat. No. 9,776,974, which is a continuation of Ser. No. 14/988,022, filed Jan. 5, 2016, now U.S. Pat. No. 9,573,930, which is a continuation of Ser. No. 14/701,304, filed Apr. 30, 2015, now U.S. Pat. No. 9,255,097, which claims the priority benefit of U.S. Provisional Application No. 61/987,354, filed May 1, 2014, the contents of these applications are hereby incorporated by reference in their entireties for all purposes.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for inhibition lysine specific demethylase-1 (LSD-1). Furthermore, the subject compounds and compositions are useful for the treatment of cancer, such as acute myeloid leukemia (AML), acute lymphoblastic leukemia (ALL), small cell lung cancer (SCLC), non-small cell lung cancer (NSCLC), neuroblastoma, small round blue cell tumors, glioblastoma, prostate cancer, breast cancer, bladder cancer, lung cancer and/or melanoma and the like. The substituted heterocyclic derivative compounds described herein are based upon a central heterocyclic ring system, such as pyrimidinone, or the like. Said pyrimidinone ring system is further substituted with a 4-cyanophenyl group and additional groups, such as aryl, heteroaryl or heterocyclic groups.

One embodiment provides a compound having the structure of Formula (I), or a pharmaceutically acceptable salt thereof,

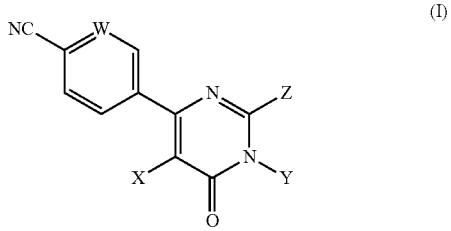

(I)

wherein,
W is N, C—H, or C—F;
X is hydrogen, halogen, —CN, optionally substituted alkyl, optionally substituted alkynyl, optionally substituted carbocyclylalkynyl, optionally substituted aryl, or optionally substituted heteroaryl;
Y is hydrogen, optionally substituted alkyl, optionally substituted cycloalkyl, or optionally substituted cycloalkylalkyl;
Z is an optionally substituted group chosen from alkyl, carbocyclyl, C-attached heterocyclyl, N-attached heterocyclyl, heterocyclylalkyl, heterocyclylalkenyl, —O-heterocyclyl, —N(R)-heterocyclyl, —O-heterocyclylalkyl, —N(R)-heterocyclylalkyl, —N(R)($C_1$-$C_4$alkylene)-$NR_2$, —O($C_1$-$C_4$alkylene)-$NR_2$, and R is hydrogen or $C_1$-$C_4$alkyl.

One embodiment provides a compound having the structure of Formula (Ia), or a pharmaceutically acceptable salt thereof,

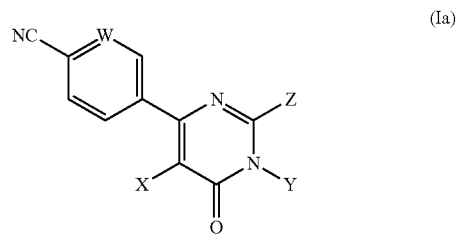

(Ia)

wherein,
W is N, C—H, or C—F;
X is hydrogen, halogen, —CN, optionally substituted alkynyl, optionally substituted carbocyclylalkynyl, optionally substituted aryl, or optionally substituted heteroaryl;
Y is hydrogen, optionally substituted alkyl, optionally substituted cycloalkyl, or optionally substituted cycloalkylalkyl; and
Z is an optionally substituted group chosen from N-attached heterocyclyl, —O-heterocyclylalkyl, —N(H)-heterocyclyl, —N(Me)-heterocyclyl, —N(H)-heterocyclylalkyl, or —N(Me)-heterocyclylalkyl.

One embodiment provides a compound having the structure of Formula (Ib), or a pharmaceutically acceptable salt thereof,

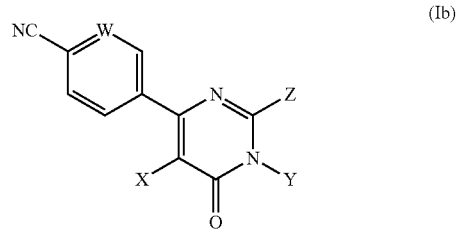

(Ib)

wherein,
W is N, C—H, or C—F;
X is hydrogen, halogen, optionally substituted alkynyl, optionally substituted carbocyclylalkynyl, optionally substituted aryl, or optionally substituted heteroaryl;
Y is hydrogen, optionally substituted alkyl, or optionally substituted cycloalkyl; and
Z is an optionally substituted group chosen from N-heterocyclyl, —O-heterocyclylalkyl, —N(H)-heterocyclylalkyl, or —N(Me)-heterocyclylalkyl.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (Ia), or a pharmaceutically acceptable salt thereof, and a pharmaceutically acceptable excipient. One embodiment provides a pharmaceutical composition comprising a compound of Formula (Ib), or a pharmaceutically acceptable salt thereof, and a pharmaceutically acceptable excipient.

One embodiment provides a method of regulating gene transcription in a cell comprising inhibiting lysine-specific demethylase 1 activity by exposing the lysine-specific demethylase 1 enzyme to a compound of Formula (I). One embodiment provides a method of regulating gene transcription in a cell comprising inhibiting lysine-specific demethylase 1 activity by exposing the lysine-specific demethylase 1 enzyme to a compound of Formula (Ia). One embodiment provides a method of regulating gene transcription in a cell comprising inhibiting lysine-specific demethylase 1 activity by exposing the lysine-specific demethylase 1 enzyme to a compound of Formula (Ib).

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (Ia), or a pharmaceutically acceptable salt thereof. One embodiment provides a method of treating cancer in a patient in need thereof, comprising administering to the patient a compound of Formula (Ib), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_8$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R')S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The point(s) of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)OR$^a$ (where t is 1 or 2), —S(O)$_1$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

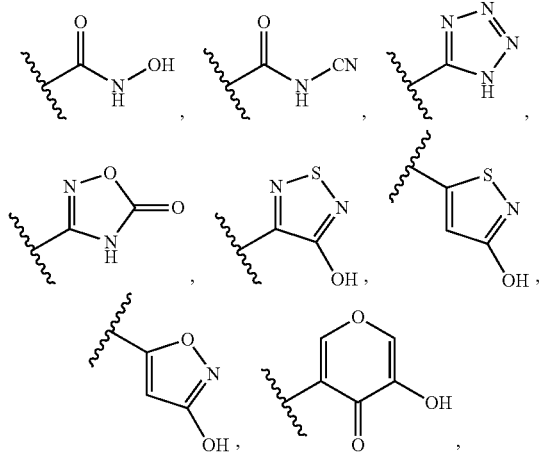

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R_2$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical, as defined above, containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetra-hydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

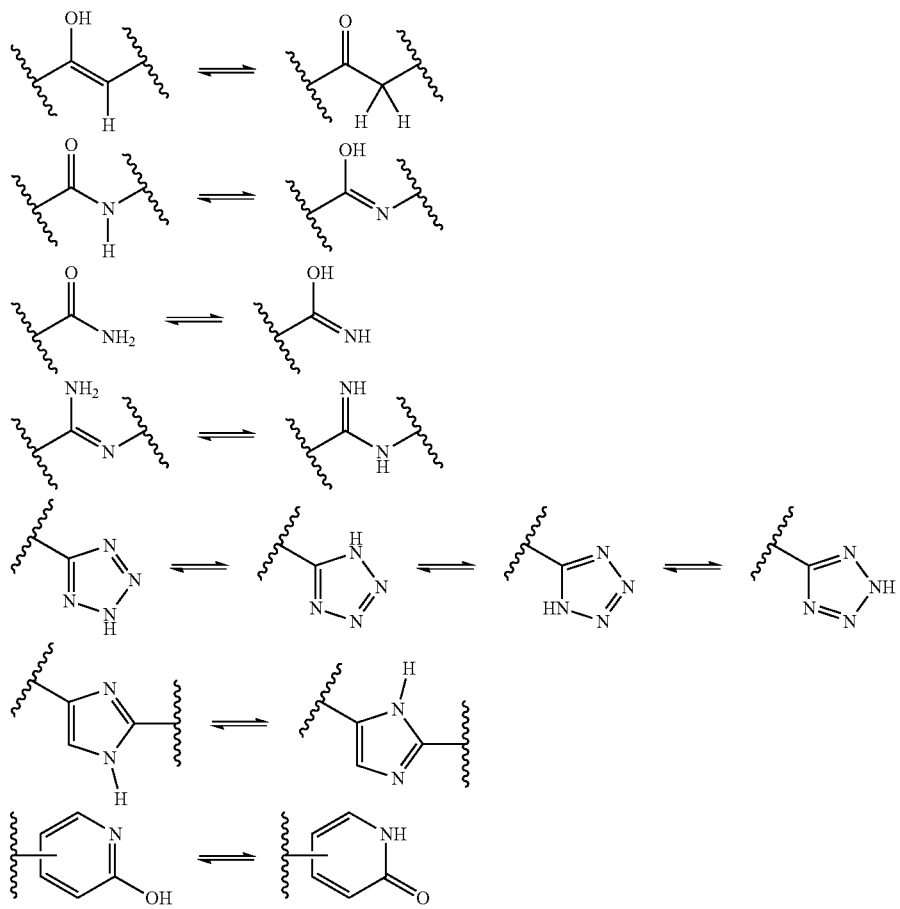

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., *Pharmaceutical Salts*, J. Pharma. Sci. 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., DESIGN OF PRODRUGS (1985), pp. 7-9, 21-24 (Elsevier, Amsterdam).

A discussion of prodrugs is provided in Higuchi, T., et al., *Pro-drugs as Novel Delivery Systems*, A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Heterocyclic Derivative Compounds

Substituted heterocyclic derivative compounds are described herein that are lysine specific demethylase-1 inhibitors. These compounds, and compositions comprising these compounds, are useful for the treatment of cancer and neoplastic disease.

One embodiment provides a compound having the structure of Formula (I), or a pharmaceutically acceptable salt thereof,

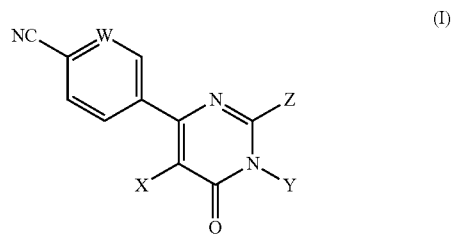

(I)

wherein,

W is N, C—H, or C—F;

X is hydrogen, halogen, —CN, optionally substituted alkyl, optionally substituted alkynyl, optionally substituted carbocyclylalkynyl, optionally substituted aryl, or optionally substituted heteroaryl;

Y is hydrogen, optionally substituted alkyl, optionally substituted cycloalkyl, or optionally substituted cycloalkylalkyl;

Z is an optionally substituted group chosen from alkyl, carbocyclyl, C-attached heterocyclyl, N-attached heterocyclyl, heterocyclylalkyl, heterocyclylalkenyl, —O-heterocyclyl, —N(R)-heterocyclyl, —O-heterocyclylalkyl, —N(R)-heterocyclylalkyl, —N(R)($C_1$-$C_4$alkylene)-$NR_2$, —O($C_1$-$C_4$alkylene)-$NR_2$, and R is hydrogen or $C_1$-$C_4$alkyl.

One embodiment provides a compound of Formula (I) having the structure of Formula (Ia), or a pharmaceutically acceptable salt thereof,

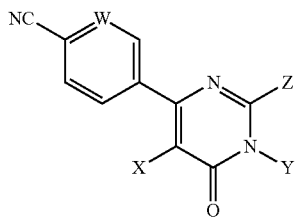

(Ia)

wherein,
W is N, C—H, or C—F;
X is hydrogen, halogen, —CN, optionally substituted alkynyl, optionally substituted carbocyclylalkynyl, optionally substituted aryl, or optionally substituted heteroaryl;
Y is hydrogen, optionally substituted alkyl, optionally substituted cycloalkyl, or optionally substituted cycloalkylalkyl; and
Z is an optionally substituted group chosen from N-attached heterocyclyl, —O-heterocyclylalkyl, —N(H)-heterocyclyl, —N(Me)-heterocyclyl, —N(H)-heterocyclylalkyl, or —N(Me)-heterocyclylalkyl.

One embodiment provides a compound of Formula (I) or (Ta) having the structure of Formula (Ib), or a pharmaceutically acceptable salt thereof,

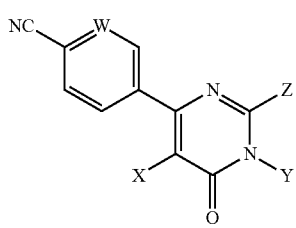

(Ib)

wherein,
W is N, C—H, or C—F;
X is hydrogen, halogen, optionally substituted alkynyl, optionally substituted carbocyclylalkynyl, optionally substituted aryl, or optionally substituted heteroaryl;
Y is hydrogen, optionally substituted alkyl, or optionally substituted cycloalkyl; and
Z is an optionally substituted group chosen from N-heterocyclyl, —O-heterocyclylalkyl, —N(H)-heterocyclylalkyl, or —N(Me)-heterocyclylalkyl.

Another embodiment provides the compound of Formula (Ib), or a pharmaceutically acceptable salt thereof, wherein W is C—H. Another embodiment provides the compound of Formula (Ib), or a pharmaceutically acceptable salt thereof, wherein W is C—F. Another embodiment provides the compound of Formula (Ib), or a pharmaceutically acceptable salt thereof, wherein W is N.

Another embodiment provides the compound of Formula (Ib), or a pharmaceutically acceptable salt thereof, wherein X is hydrogen. Another embodiment provides the compound of Formula (Ib), or a pharmaceutically acceptable salt thereof, wherein X is halogen. Another embodiment provides the compound of Formula (Ib), or a pharmaceutically acceptable salt thereof, wherein X is optionally substituted alkynyl. Another embodiment provides the compound of Formula (Ib), or a pharmaceutically acceptable salt thereof, wherein X is optionally substituted carbocyclylalkynyl.

Another embodiment provides the compound of Formula (Ib), or a pharmaceutically acceptable salt thereof, wherein X is optionally substituted aryl, or optionally substituted heteroaryl. Another embodiment provides the compound of Formula (Ib), or a pharmaceutically acceptable salt thereof, wherein X is optionally substituted aryl. Another embodiment provides the compound of Formula (Ib), or a pharmaceutically acceptable salt thereof, wherein X is an optionally substituted phenyl. Another embodiment provides the compound of Formula (Ib), or a pharmaceutically acceptable salt thereof, wherein X is optionally substituted heteroaryl. Another embodiment provides the compound of Formula (Ib), or a pharmaceutically acceptable salt thereof, wherein X is chosen from an optionally substituted pyridinyl, optionally substituted pyrazolyl, or optionally substituted indazolyl.

Another embodiment provides the compound of Formula (Ib), or a pharmaceutically acceptable salt thereof, wherein Y is hydrogen. Another embodiment provides the compound of Formula (Ib), or a pharmaceutically acceptable salt thereof, wherein Y is optionally substituted cycloalkyl. Another embodiment provides the compound of Formula (Ib), or a pharmaceutically acceptable salt thereof, wherein Y is optionally substituted alkyl. Another embodiment provides the compound of Formula (Ib), or a pharmaceutically acceptable salt thereof, wherein Y is an optionally substituted $C_1$-$C_3$ alkyl. Another embodiment provides the compound of Formula (Ib), or a pharmaceutically acceptable salt thereof, wherein Y is an optionally substituted Ct alkyl. Another embodiment provides the compound of Formula (Ib), or a pharmaceutically acceptable salt thereof, wherein Y is a methyl group.

Another embodiment provides the compound of Formula (Ib), or a pharmaceutically acceptable salt thereof, wherein Z is an optionally substituted —O-heterocyclylalkyl. Another embodiment provides the compound of Formula (Ib), or a pharmaceutically acceptable salt thereof, wherein Z is an optionally substituted —N(H)-heterocyclylalkyl. Another embodiment provides the compound of Formula (Ib), or a pharmaceutically acceptable salt thereof, wherein Z is an optionally substituted —N(Me)-heterocyclylalkyl.

Another embodiment provides the compound of Formula (Ib), or a pharmaceutically acceptable salt thereof, wherein Z is an optionally substituted —O-heterocyclylalkyl and the heterocyclylalkyl group has the formula —$R^c$-heterocyclyl and the $R^c$ is an optionally substituted $C_1$-$C_3$ alkylene chain. Another embodiment provides the compound of Formula (Ib), or a pharmaceutically acceptable salt thereof, wherein Z is an optionally substituted —O-heterocyclylalkyl and the heterocyclylalkyl group has the formula —$R^c$-heterocyclyl and the $R^c$ is an optionally substituted $C_1$ alkylene chain.

Another embodiment provides the compound of Formula (Ib), or a pharmaceutically acceptable salt thereof, wherein Z is an optionally substituted —O-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted —N(H)-heterocyclylalkyl and the heterocyclylalkyl group has the formula —$R^c$-heterocyclyl and the $R^c$ is an optionally substituted $C_1$-$C_3$ alkylene chain. Another embodiment provides the compound of Formula (Ib), or a pharmaceutically acceptable salt thereof, wherein Z is an optionally substituted —N(H)-heterocyclylalkyl and the heterocyclylalkyl group has the formula —R$^c$-heterocyclyl and the R$^c$ is an optionally substituted C$_1$ alkylene chain.

Another embodiment provides the compound of Formula (Ib), or a pharmaceutically acceptable salt thereof, wherein Z is an optionally substituted —N(H)-heterocyclylalkyl and the heterocyclylalkyl group has the formula —R$^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted —N(Me)-heterocyclylalkyl and the heterocyclylalkyl group has the formula —R$^c$-heterocyclyl and the R$^c$ is an optionally substituted C$_1$-C$_3$ alkylene chain. Another embodiment provides the compound of Formula (Ib), or a pharmaceutically acceptable salt thereof, wherein Z is an optionally substituted —N(Me)-heterocyclylalkyl and the heterocyclylalkyl group has the formula —R$^c$-heterocyclyl and the R$^c$ is an optionally substituted C$_1$ alkylene chain.

Another embodiment provides the compound of Formula (Ib), or a pharmaceutically acceptable salt thereof, wherein Z is an optionally substituted —N(Me)-heterocyclylalkyl and the heterocyclylalkyl group has the formula —R$^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted N-heterocyclyl. Another embodiment provides the compound of Formula (Ib), or a pharmaceutically acceptable salt thereof, wherein Z is a 4-, 5-, 6-, or 7-membered N-heterocyclyl. Another embodiment provides the compound of Formula (Ib), or a pharmaceutically acceptable salt thereof, wherein Z is a 6-membered N-heterocyclyl. Another embodiment provides the compound of Formula (Ib), or a pharmaceutically acceptable salt thereof, wherein Z is an optionally substituted piperidine. Another embodiment provides the compound of Formula (Ib), or a pharmaceutically acceptable salt thereof, wherein Z is an optionally substituted 4-aminopiperidine.

In some embodiments, the substituted heterocyclic derivative compound described in Formula (I), (Ia), or (Ib) has a structure provided in Table 1.

TABLE 1

| Chemical Synthesis Example | Structure | Name |
|---|---|---|
| 1 | 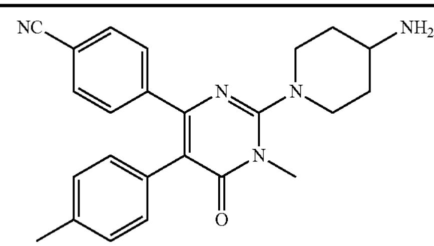 | 4-(2-(4-aminopiperidin-1-yl)-1-methyl-6-oxo-5-p-tolyl-1,6-dihydropyrimidin-4-yl)-benzonitrile |
| 2 | 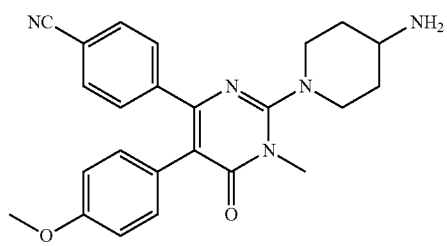 [SMILES: COc1ccc(-c2c(-c3ccc(C#N)cc3)nc(N3CCC(N)CC3)n(C)c2=O)cc1] | 4-[2-(4-amino-piperidin-1-yl)-5-(4-methoxyphenyl)-1-methyl-6-oxo-1,6-dihydro-pyrimidin-4-yl-benzonitrile |
| 3 | 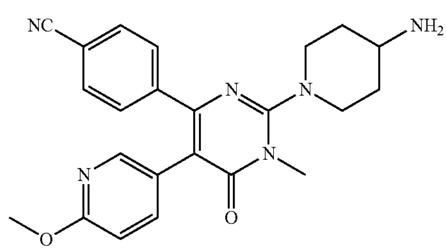 | 4-[2-(4-amino-piperidin-1-yl)-5-(6-methoxypyridin-3-yl)-1-methyl-6-oxo-1,6-dihydro-pyrimidin-4-yl]-benzonitrile |
| 4 | 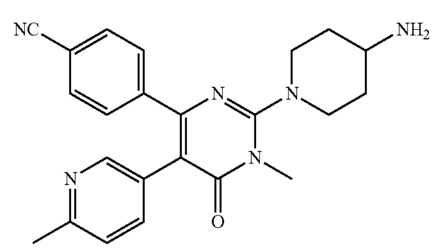 [SMILES: Cc1ccc(-c2c(-c3ccc(C#N)cc3)nc(N3CCC(N)CC3)n(C)c2=O)cn1] | 4-[2-(4-amino-piperidin-1-yl)-1-methyl-5-(6-methylpyridin-3-yl)-6-oxo-1,6-dihydro-pyrimidin-4-yl]-benzonitrile |

TABLE 1-continued

| Chemical Synthesis Example | Structure | Name |
|---|---|---|
| 5 | 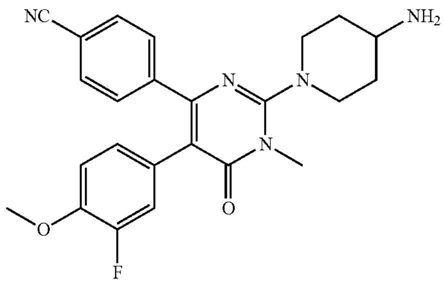 [SMILES: COc1ccc(-c2c(-c3ccc(C#N)cc3)nc(N3CCC(N)CC3)n(C)c2=O)cc1F] | 4-[2-(4-amino-piperidin-1-yl)-5-(4-methoxyphenyl)-1-methyl-6-oxo-1,6-dihydropyrimidin-4-yl]-benzonitrile |
| 6 | 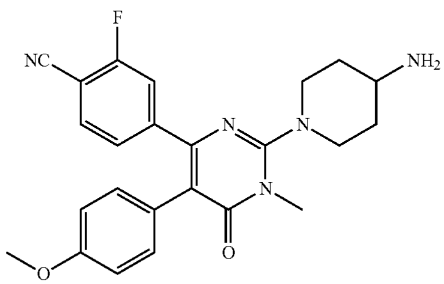 | 4-[2-(4-amino-piperidin-1-yl)-5-(4-methoxyphenyl)-1-methyl-6-oxo-1,6-dihydro-pyrimidin-4-yl]-2-fluorobenzonitrile |
| 7 | 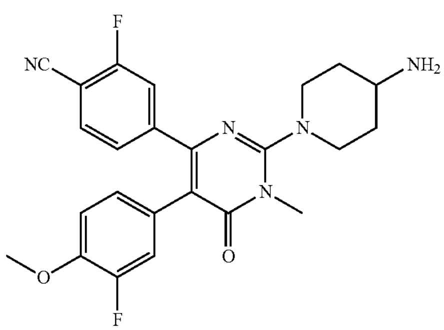 [SMILES: COc1ccc(-c2c(-c3ccc(C#N)c(F)c3)nc(N3CCC(N)CC3)n(C)c2=O)cc1F] | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile |
| 8 | 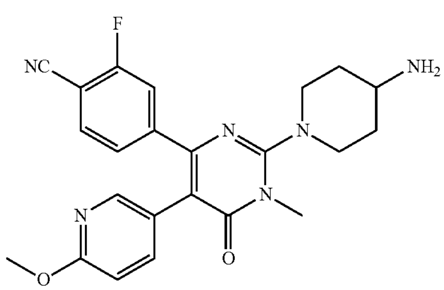 [SMILES: COc1ccc(-c2c(-c3ccc(C#N)c(F)c3)nc(N3CCC(N)CC3)n(C)c2=O)cn1] | 4-[2-(4-amino-piperidin-1-yl)-5-(6-methoxypyridin-3-yl)-1-methyl-6-oxo-1,6-dihydro-pyrimidin-4-yl]-2-fluoro-benzonitrile |
| 9 | 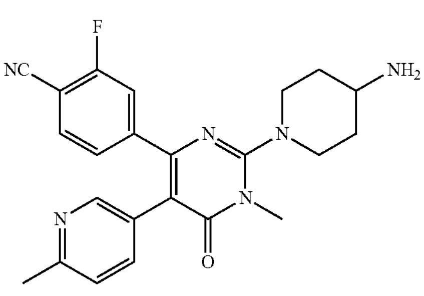 [SMILES: Cc1ccc(-c2c(-c3ccc(C#N)c(F)c3)nc(N3CCC(N)CC3)n(C)c2=O)cn1] | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 10 | 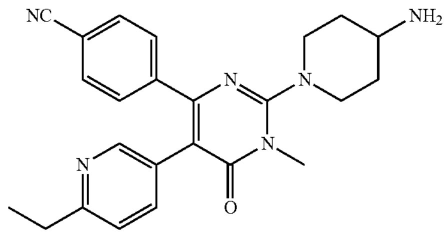 [SMILES: CCc1ccc(-c2c(-c3ccc(C#N)cc3)nc(N3CCC(N)CC3)n(C)c2=O)cn1] | 4-[2-(4-amino-piperidin-1-yl)-5-(6-ethyl-pyridin-3-yl)-1-methyl-6-oxo-1,6-dihydro-pyrimidin-4-yl]-benzonitrile |
| 11 | 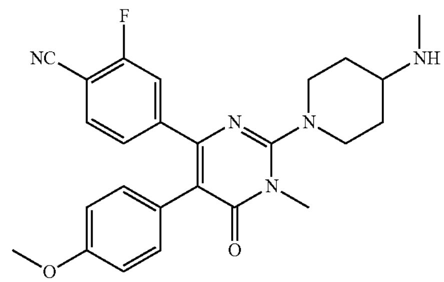 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile |
| 12 | 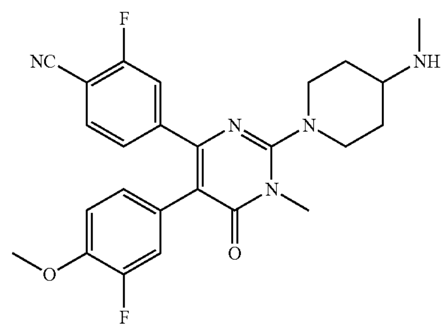 | 2-fluoro-4-[5-(3-fluoro-4-methoxy-phenyl)-1-methyl-2-(4-methylamino-piperidin-1-yl)-6-oxo-1,6-dihydro-pyrimidin-4-yl)-benzonitrile |
| 13 | 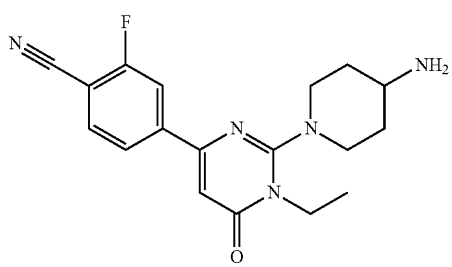 [SMILES: CCn1c(N2CCC(N)CC2)nc(-c2ccc(C#N)c(F)c2)cc1=O] | 4-[2-(4-amino-piperidin-1-yl)-1-ethyl-6-oxo-1,6-dihydro-pyrimidin-4-yl]-2-fluoro-benzonitrile |
| 14 | 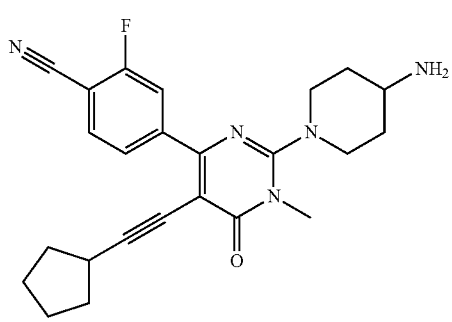 [SMILES: Cn1c(N2CCC(N)CC2)nc(-c2ccc(C#N)c(F)c2)c(C#CC2CCCC2)c1=O] | 4-[2-(4-amino-piperidin-1-yl)-5-cyclopentylethynyl-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 15 | 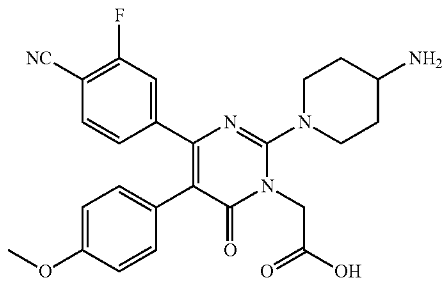 [SMILES: COc1ccc(-c2c(-c3ccc(C#N)c(F)c3)nc(N3CCC(N)CC3)n(CC(=O)O)c2=O)cc1] | [2-(4-amino-piperidin-1-yl)-4-(4-cyano-3-fluoro-phenyl)-5-(4-methoxy-phenyl)-6-oxo-6H-pyrimidin-1-yl]-acetic acid |
| 16 | 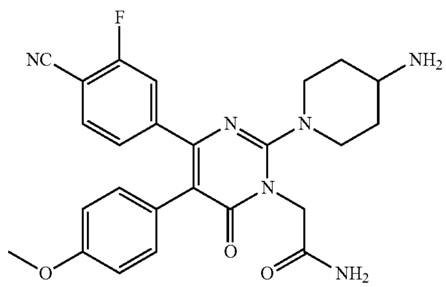 [SMILES: COc1ccc(-c2c(-c3ccc(C#N)c(F)c3)nc(N3CCC(N)CC3)n(CC(N)=O)c2=O)cc1] | 2-[2-(4-amino-piperidin-1-yl)-4-(4-cyano-3-fluoro-phenyl)-5-(4-methoxy-phenyl)-6-oxo-6H-pyrimidin-1-yl]-acetamide |
| 17 | 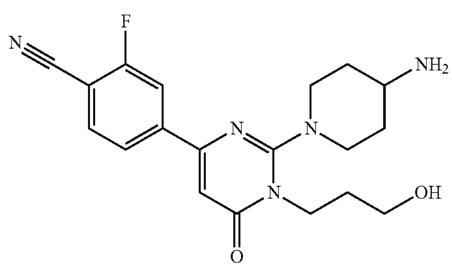 [SMILES: N#Cc1ccc(-c2cc(=O)n(CCCO)c(N3CCC(N)CC3)n2)cc1F] | 4-[2-(4-amino-piperidin-1-yl)-1-(3-hydroxy-propyl)-6-oxo-1,6-dihydro-pyrimidin-4-yl]-2-fluoro-benzonitrile |
| 18 | 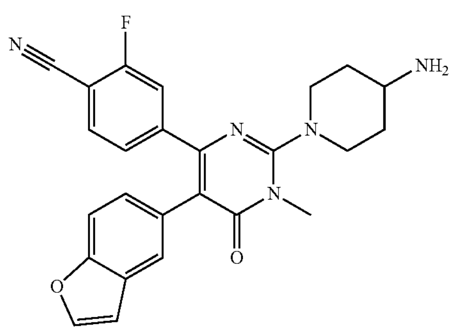 [SMILES: Cn1c(N2CCC(N)CC2)nc(-c2ccc(C#N)c(F)c2)c(-c2ccc3occc3c2)c1=O] | 4-[2-(4-amino-piperidin-1-yl)-5-benzofuran-5-yl-1-methyl-6-oxo-1,6-dihydro-pyrimidin-4-yl]-2-fluoro-benzonitrile |
| 19 | 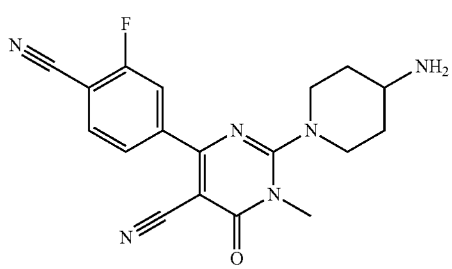 [SMILES: Cn1c(N2CCC(N)CC2)nc(-c2ccc(C#N)c(F)c2)c(C#N)c1=O] | 2-(4-amino-piperidin-1-yl)-4-(4-cyano-3-fluoro-phenyl)-1-methyl-6-oxo-1,6-dihydro-pyrimidine-5-carbonitrile |

TABLE 1-continued

| Chemical Synthesis Example | Structure | Name |
|---|---|---|
| 20 | 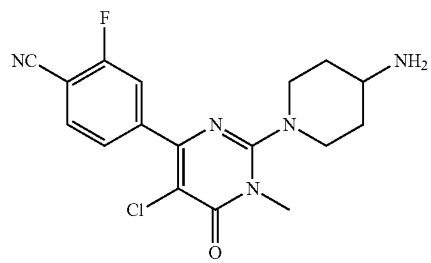 [SMILES: Cn1c(N2CCC(N)CC2)nc(-c2ccc(C#N)c(F)c2)c(Cl)c1=O] | 4-[2-(4-aminopiperidin-1-yl)-5-chloro-1-methyl-6-oxopyrimidin-4-yl]-2-fluorobenzonitrile |
| 21 | 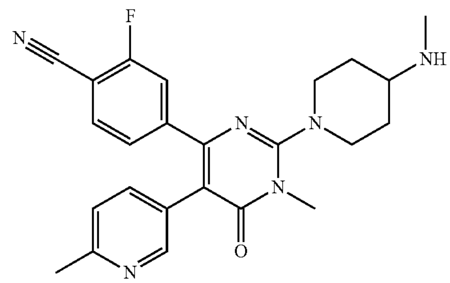 [SMILES: CNC1CCN(c2nc(-c3ccc(C#N)c(F)c3)c(-c3ccc(C)nc3)c(=O)n2C)CC1] | 2-fluoro-4-[1-methyl-2-(4-methylamino-piperidin-1-yl)-5-(6-methyl-pyridin-3-yl)-6-oxo-1,6-dihydro-pyrimidin-4-yl]-benzonitrile |
| 22 | 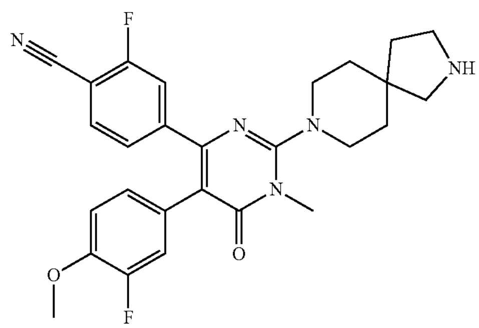 [SMILES: COc1ccc(-c2c(-c3ccc(C#N)c(F)c3)nc(N3CCC4(CCNC4)CC3)n(C)c2=O)cc1F] | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluorobenzonitrile |
| 23 | 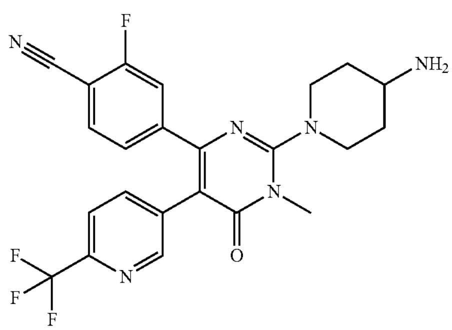 [SMILES: Cn1c(N2CCC(N)CC2)nc(-c2ccc(C#N)c(F)c2)c(-c2ccc(C(F)(F)F)nc2)c1=O] | 4-{2-(4-aminopiperidyl)-1-methyl-6-oxo-5-[6-(trifluoromethyl) (3-pyridyl)]hydropyrimidin-4-yl}-2-fluorobenzenecarbonitrile |
| 24 | 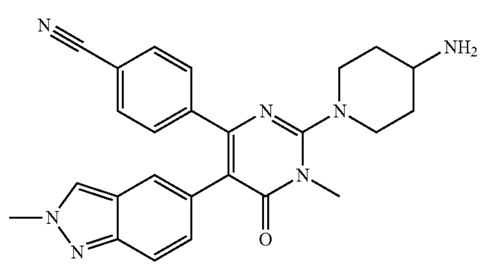 [SMILES: Cn1cc2cc(-c3c(-c4ccc(C#N)cc4)nc(N4CCC(N)CC4)n(C)c3=O)ccc2n1] | 4-[2-(4-aminopiperidyl)-1-methyl-5-(2-methyl(2H-indazol-5-yl))-6-oxohydropyrimidin-4-yl]benzenecarbonitrile |

TABLE 1-continued

| Chemical Synthesis Example | Structure | Name |
|---|---|---|
| 25 | 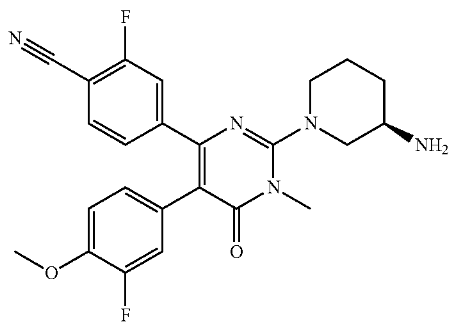 [SMILES: COc1ccc(-c2c(-c3ccc(C#N)c(F)c3)nc(N3CCC[C@@H](N)C3)n(C)c2=O)cc1F] | 4-[2-((3R)-3-aminopiperidyl)-5-(3-fluoro-4-methoxyphenyl)-1-methyl-6-oxohydropyrimidin-4-yl]-2-fluorobenzenecarbonitrile |
| 26 | 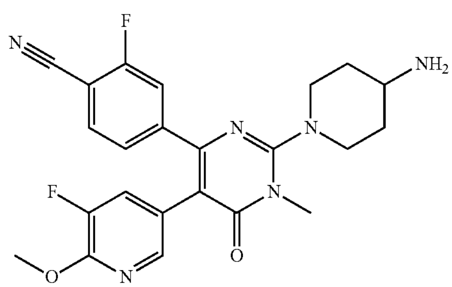 [SMILES: COc1ncc(-c2c(-c3ccc(C#N)c(F)c3)nc(N3CCC(N)CC3)n(C)c2=O)cc1F] | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile |
| 27 | 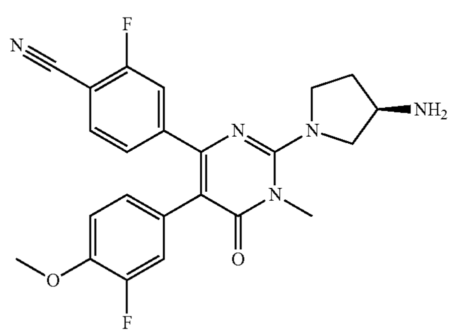 [SMILES: COc1ccc(-c2c(-c3ccc(C#N)c(F)c3)nc(N3CC[C@@H](N)C3)n(C)c2=O)cc1F] | 4-[2-((3R)-3-aminopyrrolidinyl)-5-(3-fluoro-4-methoxyphenyl)-1-methyl-6-oxohydropyrimidin-4-yl]-2-fluorobenzenecarbonitrile |
| 28 | 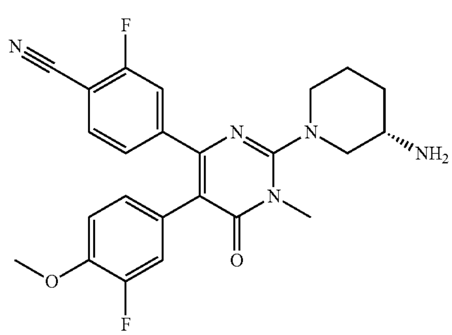 [SMILES: COc1ccc(-c2c(-c3ccc(C#N)c(F)c3)nc(N3CCC[C@H](N)C3)n(C)c2=O)cc1F] | 4-[2-((3S)-3-amino-piperidin-1-yl)-5-(3-fluoro-4-methoxy-phenyl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 29 | 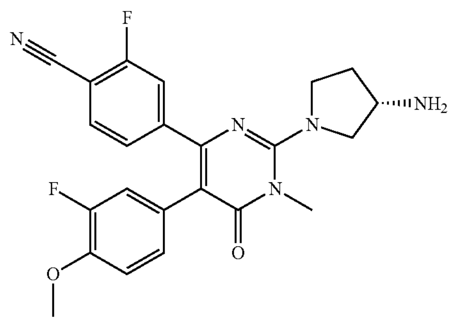 [SMILES: COc1ccc(-c2c(-c3ccc(C#N)c(F)c3)nc(N3CC[C@H](N)C3)n(C)c2=O)cc1F] | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile |
| 30 | 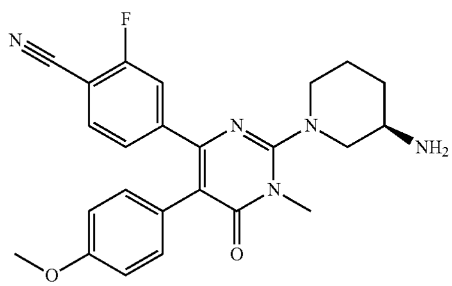 [SMILES: COc1ccc(-c2c(-c3ccc(C#N)c(F)c3)nc(N3CCC[C@@H](N)C3)n(C)c2=O)cc1] | 4-[2-((3R)-3-aminopiperidyl)-5-(4-methoxyphenyl)-1-methyl-6-oxohydro-pyrimidin-4-yl]-2-fluorobenzenecarbonitrile |
| 31 | 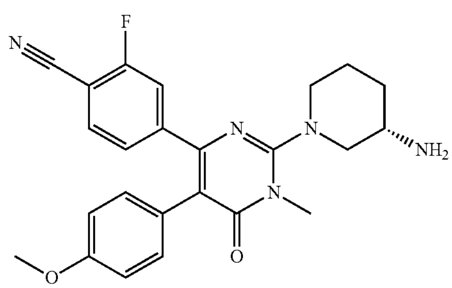 [SMILES: COc1ccc(-c2c(-c3ccc(C#N)c(F)c3)nc(N3CCC[C@H](N)C3)n(C)c2=O)cc1] | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile |
| 32 | 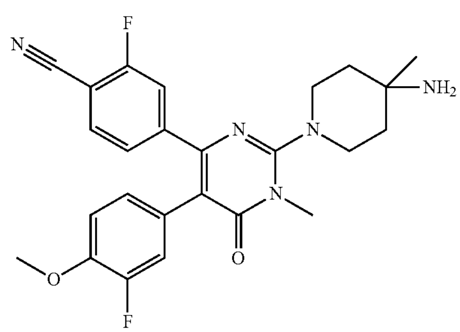 [SMILES: COc1ccc(-c2c(-c3ccc(C#N)c(F)c3)nc(N3CCC(C)(N)CC3)n(C)c2=O)cc1F] | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrile |
| 33 | 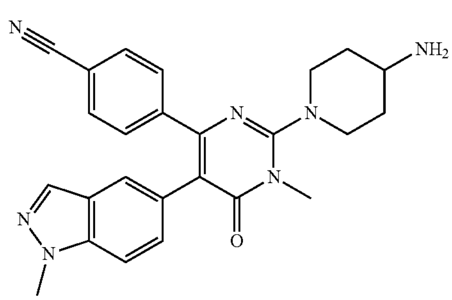 [SMILES: Cn1c(N2CCC(N)CC2)nc(-c2ccc(C#N)cc2)c(-c2ccc3c(cnn3C)c2)c1=O] | 4-[2-(4-aminopiperidyl)-1-methyl-5-(1-methyl(1H-indazol-5-yl))-6-oxohydropyrimidin-4-yl]benzenecarbonitrile |

TABLE 1-continued

| Chemical Synthesis Example | Structure | Name |
|---|---|---|
| 34 | 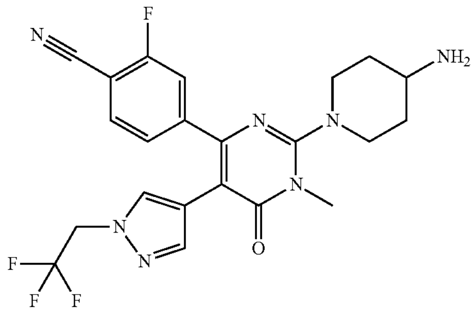 [SMILES: Cn1c(N2CCC(N)CC2)nc(-c2ccc(C#N)c(F)c2)c(-c2cnn(CC(F)(F)F)c2)c1=O] | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile |
| 35 | 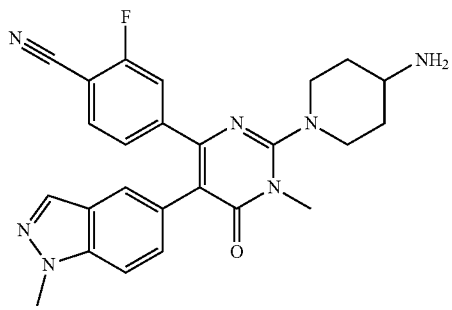 [SMILES: Cn1c(N2CCC(N)CC2)nc(-c2ccc(C#N)c(F)c2)c(-c2ccc3c(cnn3C)c2)c1=O] | 4-[2-(4-amino-piperin-1-yl)-1-methyl-5-(1-methyl-1H-indazol-5-yl)-6-oxo-1,6-dihydro-pyrimidin-4-yl]-2-fluoro-benzonitrile |
| 36 | 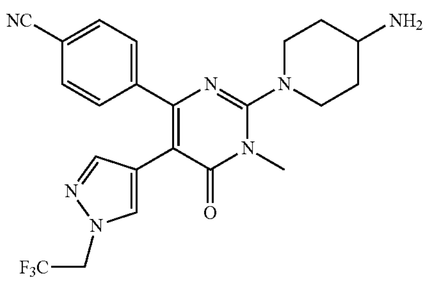 [SMILES: Cn1c(N2CCC(N)CC2)nc(-c2ccc(C#N)cc2)c(-c2cnn(CC(F)(F)F)c2)c1=O] | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile |
| 37 | 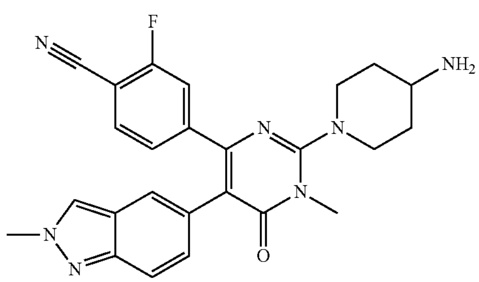 [SMILES: Cn1cc2cc(-c3c(-c4ccc(C#N)c(F)c4)nc(N4CCC(N)CC4)n(C)c3=O)ccc2n1] | 4-[2-(4-aminopiperidyl)-1-methyl-5-(2-methyl(2H-indazol-5-yl))-6-oxohydropyrimidin-4-yl]-2-fluorobenzenecarbonitrile |
| 38 | 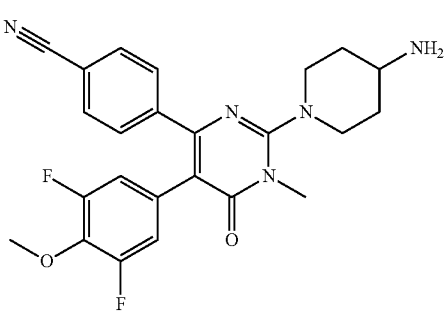 [SMILES: COc1c(F)cc(-c2c(-c3ccc(C#N)cc3)nc(N3CCC(N)CC3)n(C)c2=O)cc1F] | 4-[2-(4-aminopiperidyl)-5-(3,5-di fluoro-4-methoxyphenyl)-1-methyl-6-oxohydropyrimidin-4-yl]benzenecarbonitrile |

TABLE 1-continued

| Chemical Synthesis Example | Structure | Name |
|---|---|---|
| 39 | 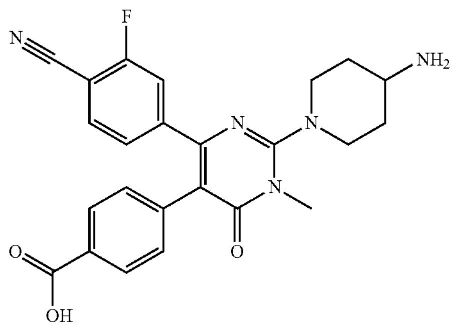 [SMILES: Cn1c(N2CCC(N)CC2)nc(-c2ccc(C#N)c(F)c2)c(-c2ccc(C(=O)O)cc2)c1=O] | 4-[2-(4-aminopiperidyl)-6-(4-cyano-3-fluorophenyl)-3-methyl-4-oxo-3-hydropyrimidin-5-yl]benzoic acid |
| 40 | 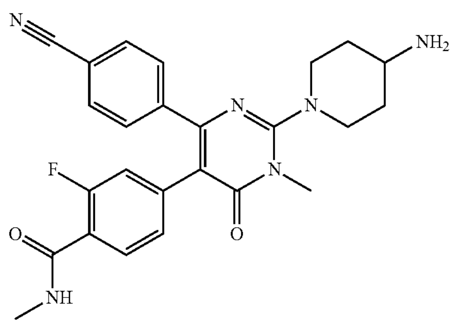 [SMILES: CNC(=O)c1ccc(-c2c(-c3ccc(C#N)cc3)nc(N3CCC(N)CC3)n(C)c2=O)cc1F] | {4-[2-(4-aminopiperidyl)-6-(4-cyanophenyl)-3-methyl-4-oxo(3-hydropyrimidin-5-yl)]-2-fluorophenyl}-N-methylcarboxamide |
| 41 | 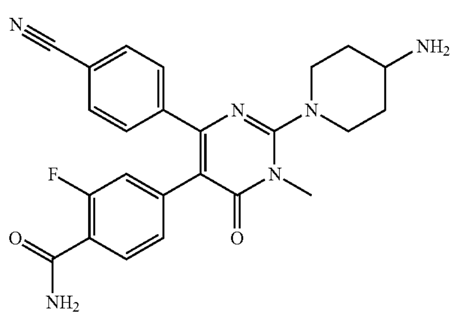 [SMILES: Cn1c(N2CCC(N)CC2)nc(-c2ccc(C#N)cc2)c(-c2ccc(C(N)=O)c(F)c2)c1=O] | 4-[2-(4-aminopiperidyl)-6-(4-cyanophenyl)-3-methyl-4-oxo(3-hydropyrimidin-5-yl)]-2-fluorobenzamide |
| 42 | 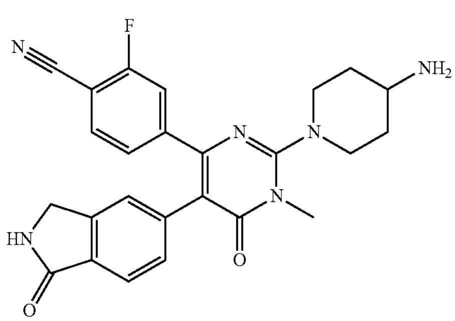 [SMILES: Cn1c(N2CCC(N)CC2)nc(-c2ccc(C#N)c(F)c2)c(-c2ccc3c(c2)CNC3=O)c1=O] | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile |

TABLE 1-continued

| Chemical Synthesis Example | Structure | Name |
|---|---|---|
| 43 | 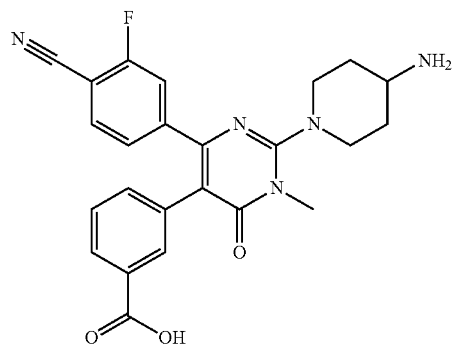 [SMILES: Cn1c(N2CCC(N)CC2)nc(-c2ccc(C#N)c(F)c2)c(-c2cccc(C(=O)O)c2)c1=O] | 3-[2-(4-amino-piperidin-1-yl)-4-(4-cyano-3-fluoro-phenyl)-1-methyl-6-oxo-1,6-dihydro-pyrimidin-5-yl]-benzoic acid |
| 44 | 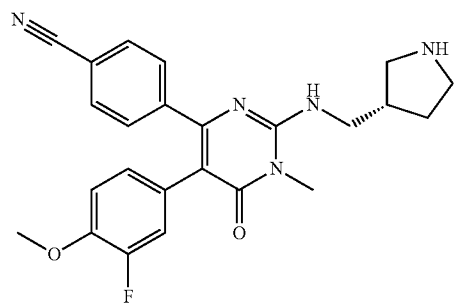 [SMILES: COc1ccc(-c2c(-c3ccc(C#N)cc3)nc(NC[C@H]3CCNC3)n(C)c2=O)cc1F] | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl}-benzonitrile |
| 45 | 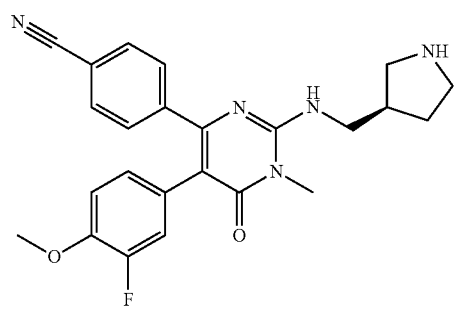 [SMILES: COc1ccc(-c2c(-c3ccc(C#N)cc3)nc(NC[C@@H]3CCNC3)n(C)c2=O)cc1F] | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl}-benzonitrile |
| 46 | 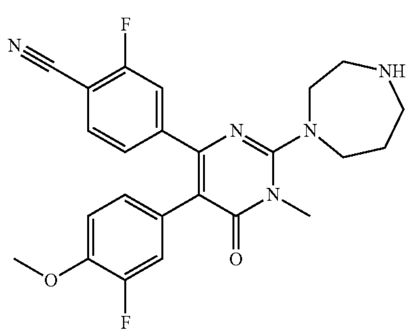 [SMILES: COc1ccc(-c2c(-c3ccc(C#N)c(F)c3)nc(N3CCCNCC3)n(C)c2=O)cc1F] | 4-[2-[1,4]diazepan-1-yl-5-(3-fluoro-4-methoxy-phenyl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 47 | 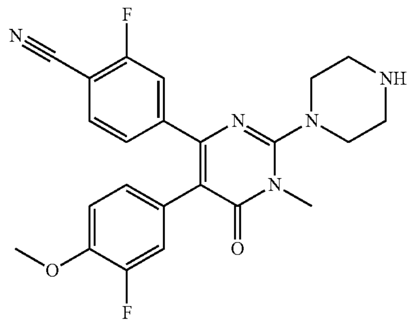 [SMILES: COc1ccc(-c2c(-c3ccc(C#N)c(F)c3)nc(N3CCNCC3)n(C)c2=O)cc1F] | 2-fluoro-4-[5-(3-fluoro-4-methoxy-phenyl)-1-methyl-6-oxo-2-piperazin-1-yl-1,6-dihydro-pyrimidin-4-yl]-benzonitrile |
| 48 | 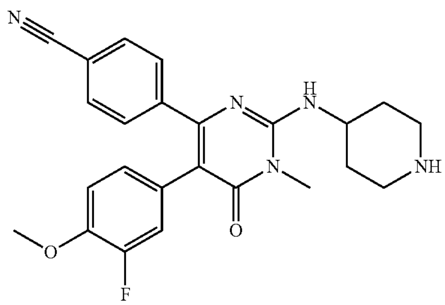 [SMILES: COc1ccc(-c2c(-c3ccc(C#N)cc3)nc(NC3CCNCC3)n(C)c2=O)cc1F] | 4-[5-(3-fluoro-4-methoxy-phenyl)-1-methyl-6-oxo-2-(piperidin-4-ylamino)-1,6-dihydro-pyrimidin-4-yl]-benzonitrile |
| 49 | 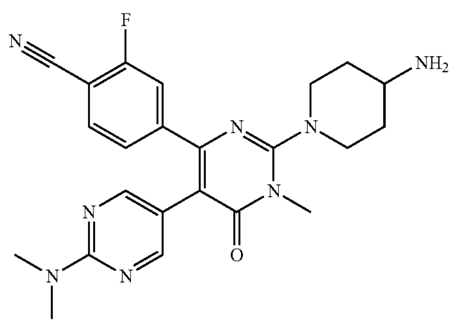 | 4-[2-(4-amino-piperidin-1-yl)-2'-dimethylamino-1-methyl-6-oxo-1,6-dihydro-[5,5']bipyrimidinyl-4-yl]-2-fluoro-benzonitrile |
| 50 | 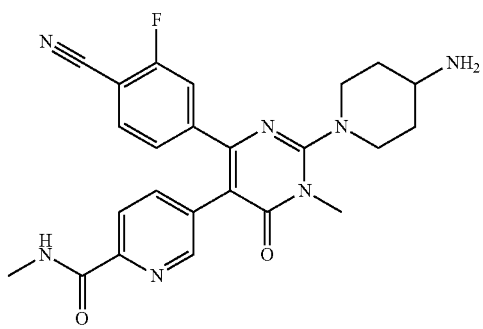 [SMILES: CNC(=O)c1ccc(-c2c(-c3ccc(C#N)c(F)c3)nc(N3CCC(N)CC3)n(C)c2=O)cn1] | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide |
| 51 | 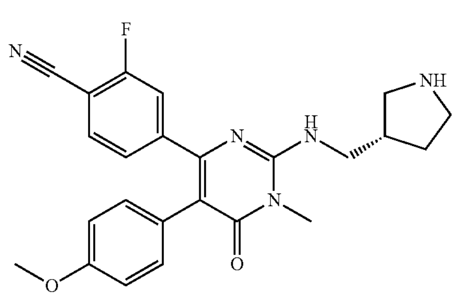 [SMILES: COc1ccc(-c2c(-c3ccc(C#N)c(F)c3)nc(NC[C@H]3CCNC3)n(C)c2=O)cc1] | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl}-benzonitrile |

TABLE 1-continued

| Chemical Synthesis Example | Structure | Name |
|---|---|---|
| 52 | 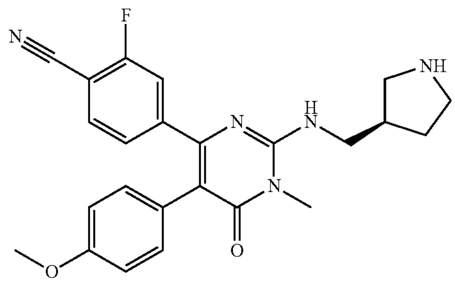 [SMILES: COc1ccc(-c2c(-c3ccc(C#N)c(F)c3)nc(NC[C@@H]3CCNC3)n(C)c2=O)cc1] | 2-fluoro-4-{5-(4-methoxy-phenyl)-1-methyl-6-oxo-2-[(3R)-(pyrrolidin-3-ylmethyl)-amino]-1,6-dihydro-pyrimidin-4-yl}-benzonitrile |
| 53 | 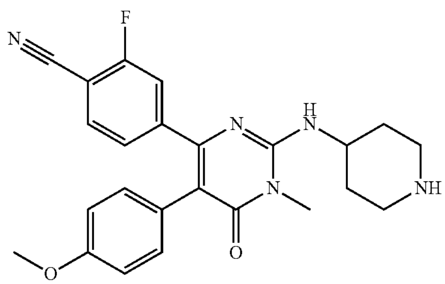 [SMILES: COc1ccc(-c2c(-c3ccc(C#N)c(F)c3)nc(NC3CCNCC3)n(C)c2=O)cc1] | 2-fluoro-4-[5-(4-methoxy-phenyl)-1-methyl-6-oxo-2-(piperidin-4-ylamino)-1,6-dihydro-pyrimidin-4-yl]-benzonitrile |
| 54 | 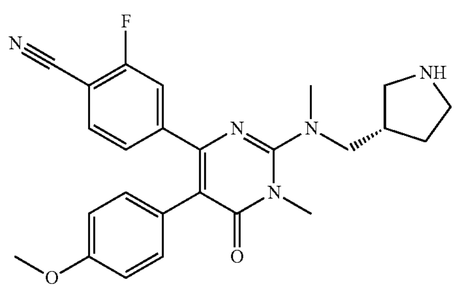 [SMILES: COc1ccc(-c2c(-c3ccc(C#N)c(F)c3)nc(N(C)C[C@H]3CCNC3)n(C)c2=O)cc1] | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile |
| 55 | 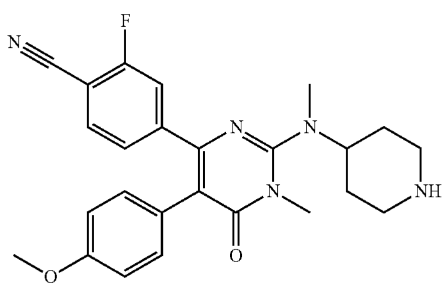 [SMILES: COc1ccc(-c2c(-c3ccc(C#N)c(F)c3)nc(N(C)C3CCNCC3)n(C)c2=O)cc1] | 2-fluoro-4-[5-(4-methoxy-phenyl)-1-methyl-2-(methyl-piperidin-4-yl-amino)-6-oxo-1,6-dihydro-pyrimidin-4-yl]-benzonitrile |
| 56 | 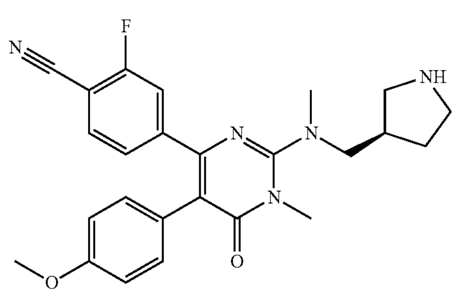 [SMILES: COc1ccc(-c2c(-c3ccc(C#N)c(F)c3)nc(N(C)C[C@@H]3CCNC3)n(C)c2=O)cc1] | 2-fluoro-4-[5-(4-methoxy-phenyl)-1-methyl-2-(methyl-pyrrolidin-3-yl methyl-amino)-6-oxo-1,6-dihydro-pyrimidin-4-yl]-benzonitrile |

TABLE 1-continued

| Chemical Synthesis Example | Structure | Name |
|---|---|---|
| 57 | 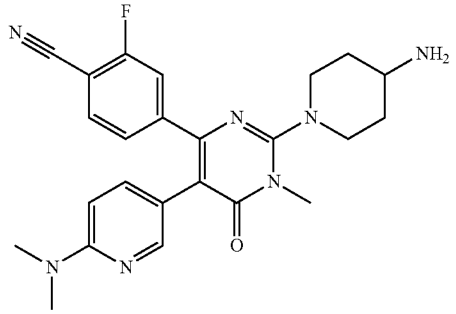 [SMILES: CN(C)c1ccc(-c2c(-c3ccc(C#N)c(F)c3)nc(N3CCC(N)CC3)n(C)c2=O)cn1] | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile |
| 58 | 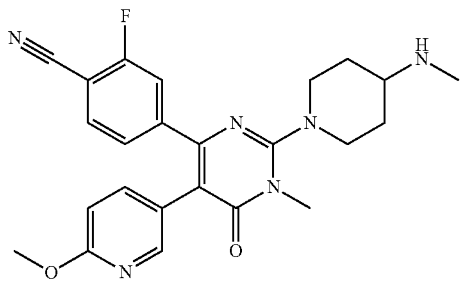 | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile |
| 59 | 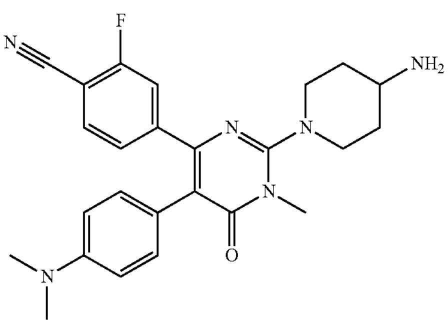 [SMILES: CN(C)c1ccc(-c2c(-c3ccc(C#N)c(F)c3)nc(N3CCC(N)CC3)n(C)c2=O)cc1] | 4-[2-(4-amino-piperidin-1-yl)-5-(4-dimethylamino-phenyl)-1-methyl-6-oxo-1,6-dihydro-pyrimidin-4-yl]-2-fluoro-benzonitrile |
| 60 | 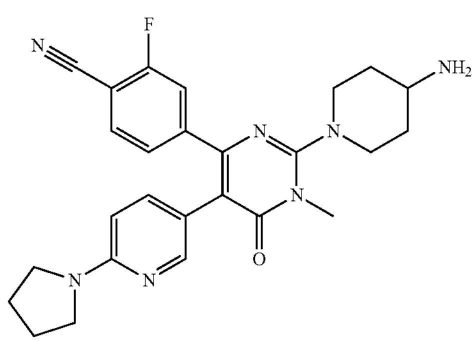 [SMILES: Cn1c(N2CCC(N)CC2)nc(-c2ccc(C#N)c(F)c2)c(-c2ccc(N3CCCC3)nc2)c1=O] | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile |
| 61 | 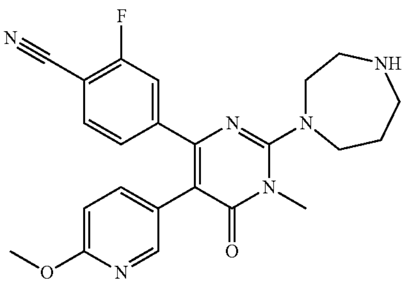 [SMILES: COc1ccc(-c2c(-c3ccc(C#N)c(F)c3)nc(N3CCCNCC3)n(C)c2=O)cn1] | 4-[2-[1,4]diazepan-1-yl-5-(6-methoxy-pyridin-3-yl)-1-methyl-6-oxo-1,6-dihydro-pyrimidin-4-yl]-2-fluoro benzonitrile |

TABLE 1-continued

| Chemical Synthesis Example | Structure | Name |
|---|---|---|
| 62 | 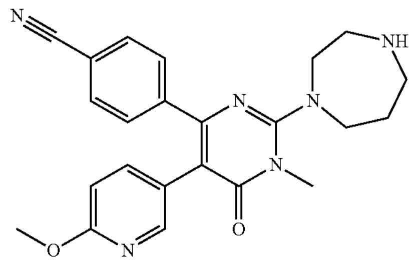 [SMILES: COc1ccc(-c2c(-c3ccc(C#N)cc3)nc(N3CCCNCC3)n(C)c2=O)cn1] | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile |
| 63 | 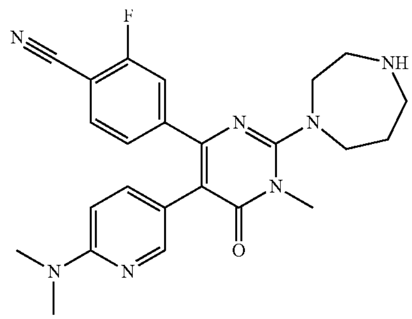 [SMILES: CN(C)c1ccc(-c2c(-c3ccc(C#N)c(F)c3)nc(N3CCCNCC3)n(C)c2=O)cn1] | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile |
| 64 | 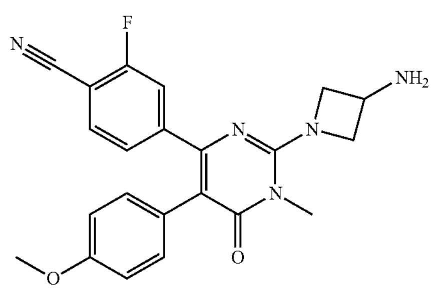 [SMILES: COc1ccc(-c2c(-c3ccc(C#N)c(F)c3)nc(N3CC(N)C3)n(C)c2=O)cc1] | 4-[2-(3-amino-azetidin-1-yl)-5-(4-methoxy-phenyl)-1-methyl-6-oxo-1,6-dihydro-pyrimidin-4-yl]-2-fluoro-benzonitrile |
| 65 | 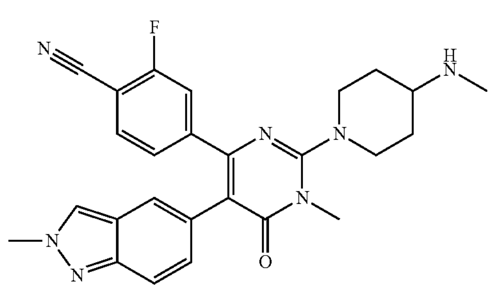 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile |
| 66 | 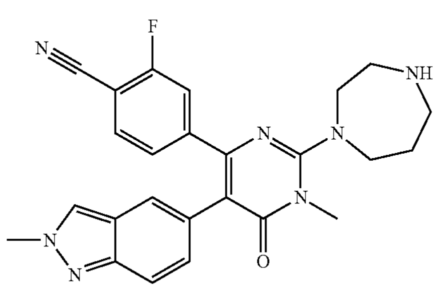 [SMILES: Cn1cc2cc(-c3c(-c4ccc(C#N)c(F)c4)nc(N4CCCNCC4)n(C)c3=O)ccc2n1] | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile |

TABLE 1-continued

| Chemical Synthesis Example | Structure | Name |
|---|---|---|
| 67 | 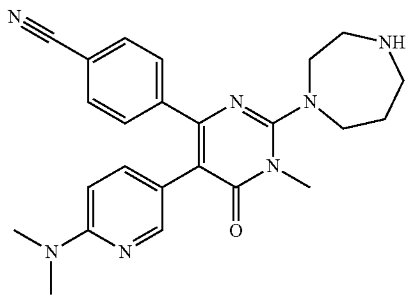 [SMILES: CN(C)c1ccc(-c2c(-c3ccc(C#N)cc3)nc(N3CCCNCC3)n(C)c2=O)cn1] | 4-[2-[1,4]diazepan-1-yl-5-(6-dimethylamino-pyridin-3-yl)-1-methyl-6-oxo-1,6-dihydro-pyrimidin-4-yl]-benzonitrile |
| 68 | 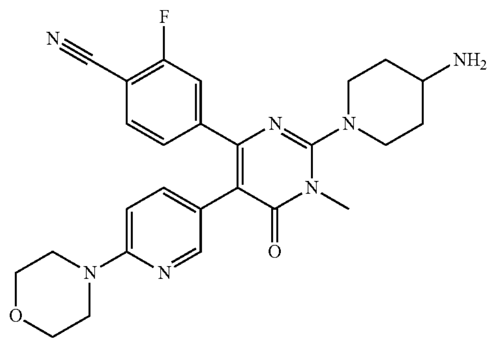 [SMILES: Cn1c(N2CCC(N)CC2)nc(-c2ccc(C#N)c(F)c2)c(-c2ccc(N3CCOCC3)nc2)c1=O] | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile |
| 69 | 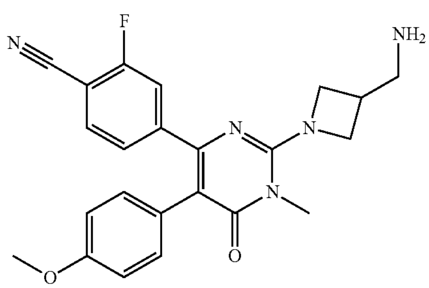 [SMILES: COc1ccc(-c2c(-c3ccc(C#N)c(F)c3)nc(N3CC(CN)C3)n(C)c2=O)cc1] | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile |
| 70 | 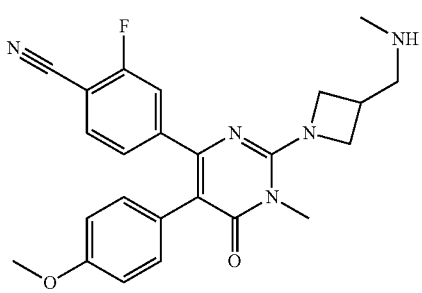 [SMILES: CNCC1CN(c2nc(-c3ccc(C#N)c(F)c3)c(-c3ccc(OC)cc3)c(=O)n2C)C1] | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile |
| 71 | 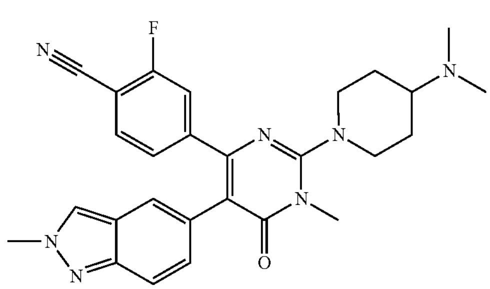 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile |

TABLE 1-continued

| Chemical Synthesis Example | Structure | Name |
|---|---|---|
| 72 | 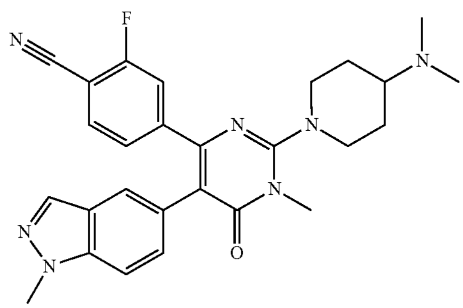 [SMILES: CN(C)C1CCN(c2nc(-c3ccc(C#N)c(F)c3)c(-c3ccc4c(cnn4C)c3)c(=O)n2C)CC1] | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile |
| 73 | 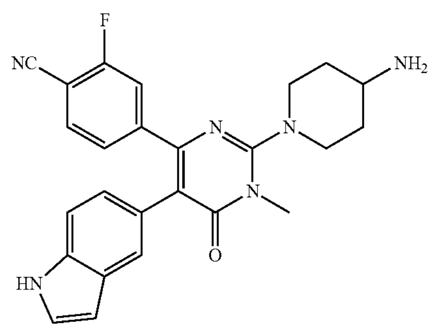 [SMILES: Cn1c(N2CCC(N)CC2)nc(-c2ccc(C#N)c(F)c2)c(-c2ccc3[nH]ccc3c2)c1=O] | 4-[2-(4-amino-piperidin-1-yl)-5-(1H-indol-5-yl)-1-methyl-6-oxo-1,6-dihydro-pyrimidin-4-yl]-2-fluoro-benzonitrile |
| 74 | 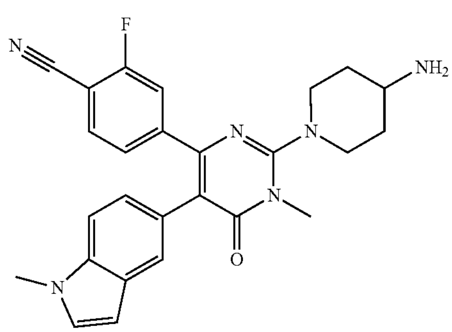 [SMILES: Cn1c(N2CCC(N)CC2)nc(-c2ccc(C#N)c(F)c2)c(-c2ccc3c(ccn3C)c2)c1=O] | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile |
| 75 | 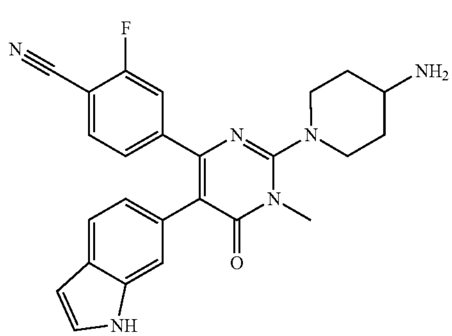 [SMILES: Cn1c(N2CCC(N)CC2)nc(-c2ccc(C#N)c(F)c2)c(-c2ccc3cc[nH]c3c2)c1=O] | 4-[2-(4-amino-piperidin-1-yl)-5-(1H-indol-6-yl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 76 | 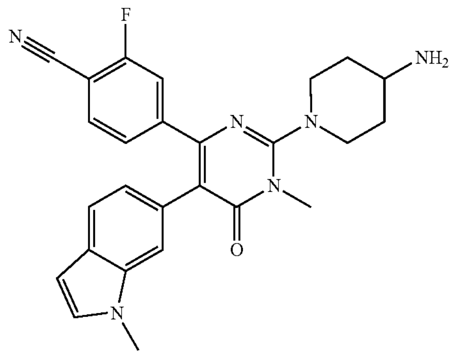 [SMILES: Cn1c(N2CCC(N)CC2)nc(-c2ccc(C#N)c(F)c2)c(-c2ccc3ccn(C)c3c2)c1=O] | 4-[2-[4-amino-piperidin-l-yl)-1-methyl-5-(1-methyl-1H-indol-6-yl)-6-oxo-1,6-dihydro-pyrimidin-4-yl]-2-fluoro-benzonitrile |
| 77 | 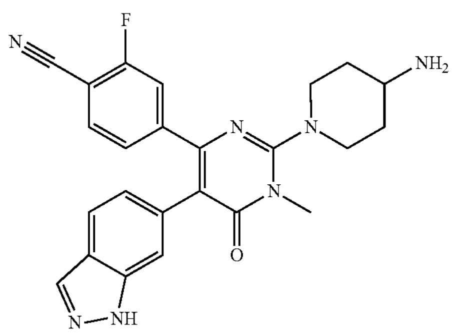 [SMILES: Cn1c(N2CCC(N)CC2)nc(-c2ccc(C#N)c(F)c2)c(-c2ccc3cn[nH]c3c2)c1=O] | 4-[2-(4-amino-piperidin-1-yl)-5-(1H-indazol-6-yl)-1-methyl-6-oxo-1,6-dihydro-pyrimidin-4-yl]-2-fluoro-benzonitrile |
| 78 | 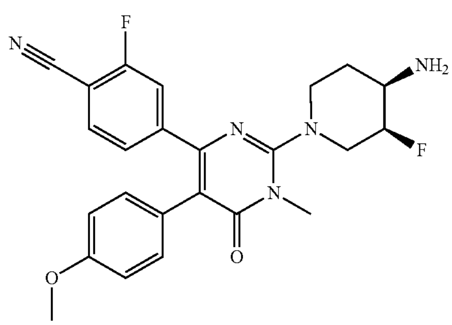 [SMILES: COc1ccc(-c2c(-c3ccc(C#N)c(F)c3)nc(N3CC[C@@H](N)[C@@H](F)C3)n(C)c2=O)cc1] | 4-[2-((4R,3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile |
| 79 | 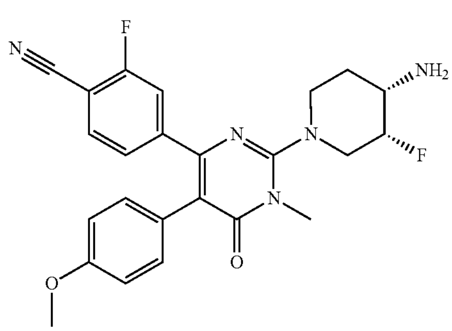 [SMILES: COc1ccc(-c2c(-c3ccc(C#N)c(F)c3)nc(N3CC[C@H](N)[C@H](F)C3)n(C)c2=O)cc1] | 4-[2-((4S,3R)-4-amino-3-fluoro-piperidin-l-yl)-5-(4-methoxy-phenyl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 80 | 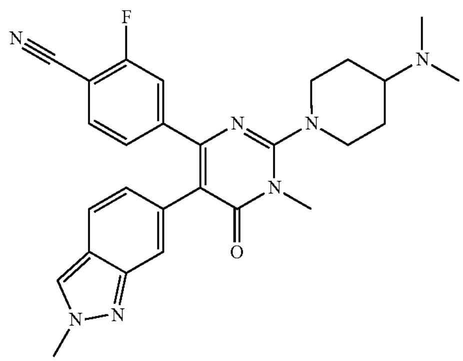 [SMILES: CN(C)C1CCN(c2nc(-c3ccc(C#N)c(F)c3)c(-c3ccc4cn(C)nc4c3)c(=O)n2C)CC1] | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile |
| 81 | 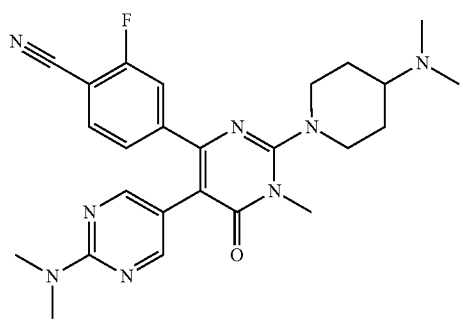 [SMILES: CN(C)c1ncc(-c2c(-c3ccc(C#N)c(F)c3)nc(N3CCC(N(C)C)CC3)n(C)c2=O)cn1] | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile |
| 82 | 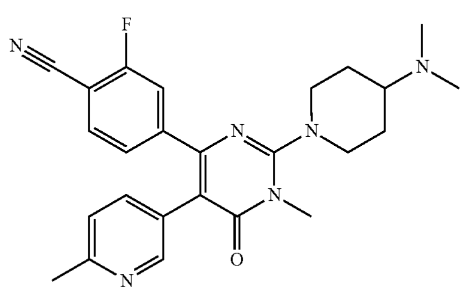 [SMILES: Cc1ccc(-c2c(-c3ccc(C#N)c(F)c3)nc(N3CCC(N(C)C)CC3)n(C)c2=O)cn1] | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile |
| 83 | 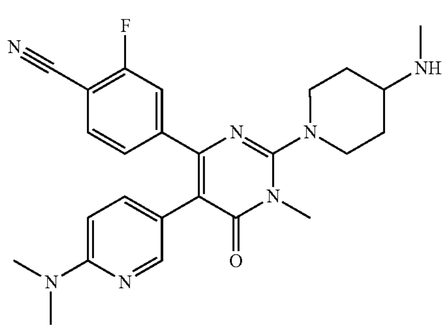 [SMILES: CNC1CCN(c2nc(-c3ccc(C#N)c(F)c3)c(-c3ccc(N(C)C)nc3)c(=O)n2C)CC1] | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile |

TABLE 1-continued

| Chemical Synthesis Example | Structure | Name |
|---|---|---|
| 84 | 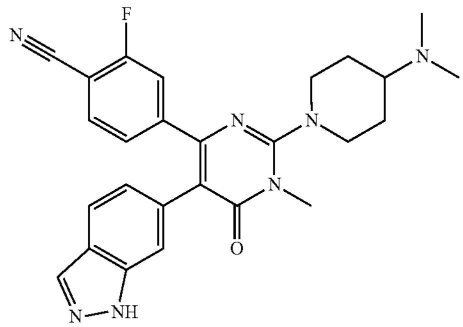 [SMILES: CN(C)C1CCN(c2nc(-c3ccc(C#N)c(F)c3)c(-c3ccc4cn[nH]c4c3)c(=O)n2C)CC1] | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile |
| 85 | 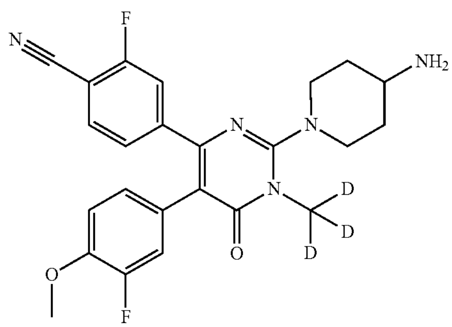 [SMILES: [2H]C([2H])([2H])n1c(N2CCC(N)CC2)nc(-c2ccc(C#N)c(F)c2)c(-c2ccc(OC)c(F)c2)c1=O] | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile |
| 86 | 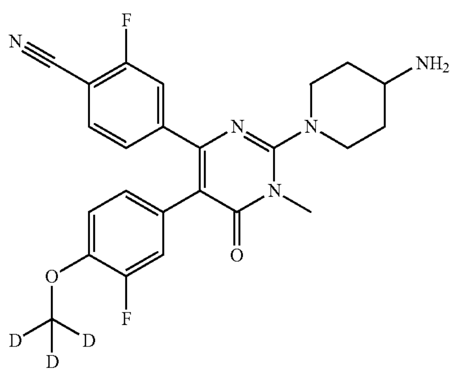 [SMILES: [2H]C([2H])([2H])Oc1ccc(-c2c(-c3ccc(C#N)c(F)c3)nc(N3CCC(N)CC3)n(C)c2=O)cc1F] | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile |
| 87 | 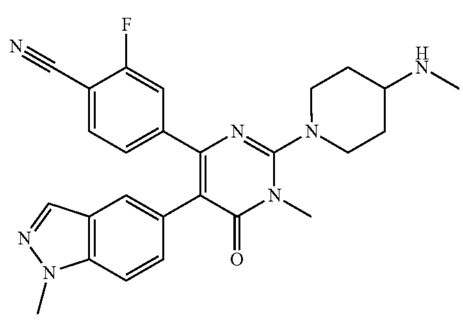 [SMILES: CNC1CCN(c2nc(-c3ccc(C#N)c(F)c3)c(-c3ccc4c(cnn4C)c3)c(=O)n2C)CC1] | 2-fluoro-4-[1-methyl-2-[4-(methylamino)piperidin-1-yl]-5-(1-methylindazol-5-yl)-6-oxopyrimidin-4-yl]benzonitrile |

TABLE 1-continued

| Chemical Synthesis Example | Structure | Name |
|---|---|---|
| 88 | 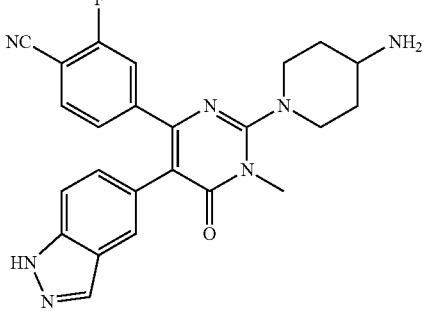 | 4-[2-(4-aminopiperidin-1-yl)-5-(1H-indazol-5-yl)-1-methyl-6-oxopyrimidin-4-yl]-2-fluorobenzonitrile |
| 89 | 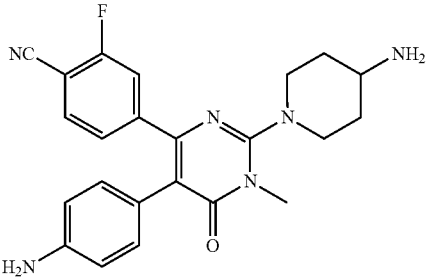 [SMILES: Cn1c(N2CCC(N)CC2)nc(-c2ccc(C#N)c(F)c2)c(-c2ccc(N)cc2)c1=O] | 4-[5-(4-aminophenyl)-2-(4-aminopiperidin-1-yl)-1-methyl-6-oxopyrimidin-4-yl]-2-fluorobenzonitrile |
| 90 | 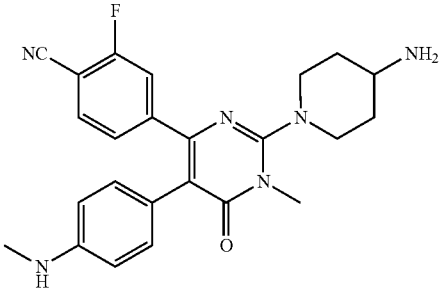 [SMILES: CNc1ccc(-c2c(-c3ccc(C#N)c(F)c3)nc(N3CCC(N)CC3)n(C)c2=O)cc1] | 4-[2-(4-aminopiperidin-1-yl)-1-methyl-5[4-(methylamino)phenyl]-6-oxopyrimidin-4-yl]-2-fluorobenzonitrile |
| 91 | 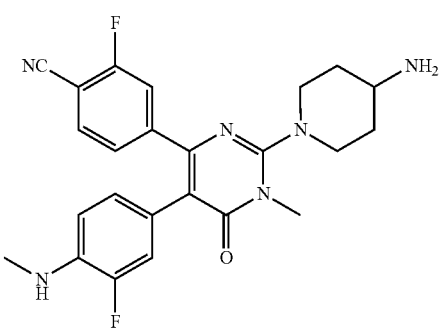 [SMILES: CNc1ccc(-c2c(-c3ccc(C#N)c(F)c3)nc(N3CCC(N)CC3)n(C)c2=O)cc1F] | 4-[2-(4-aminopiperidin-1-yl)-5-[3-fluoro-4-(methylamino)phenyl]-1-methyl-6-oxopyrimidin-4-yl]-2-fluorobenzonitrile |
| 92 | 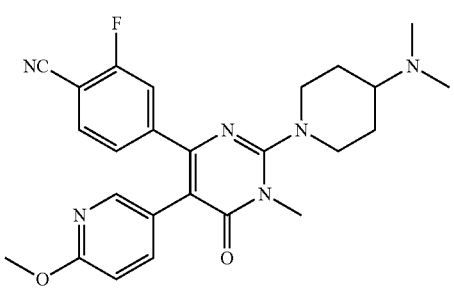 | 4-[2-[4-(dimethylamino)piperidin-1-yl]-5-(6-methoxypyridin-3-yl)-1-methyl-6-oxopyrimidin-4-yl]-2-fluorobenzonitrile |

TABLE 1-continued

| Chemical Synthesis Example | Structure | Name |
|---|---|---|
| 93 | 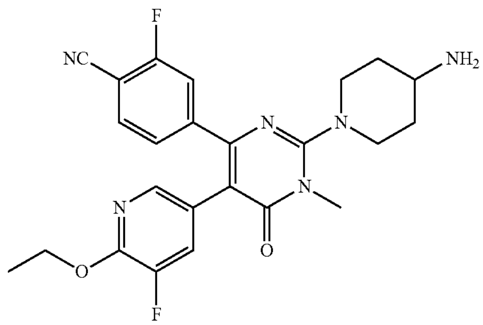 [SMILES: CCOc1ncc(-c2c(-c3ccc(C#N)c(F)c3)nc(N3CCC(N)CC3)n(C)c2=O)cc1F] | 4-[2-(4-aminopiperidin-1-yl)-5-(6-ethoxy-5-fluoropyridin-3-yl)-1-methyl-6-oxopyrimidin-4-yl]-2-fluorobenzonitrile |
| 94 | 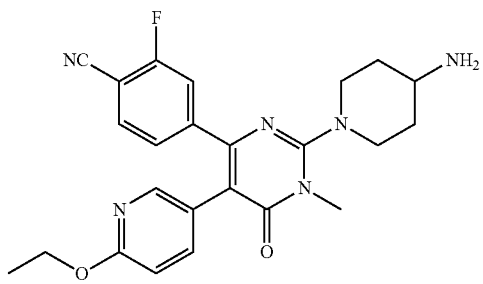 | 4-[2-(4-aminopiperidin-1-yl)-5-(6-ethoxypyridin-3-yl)-1-methyl-6-oxopyrimidin-4-yl]-2-fluorobenzonitrile |
| 95 | 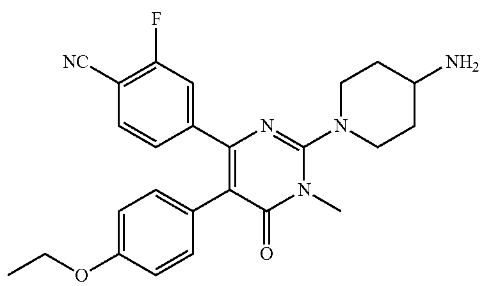 [SMILES: CCOc1ccc(-c2c(-c3ccc(C#N)c(F)c3)nc(N3CCC(N)CC3)n(C)c2=O)cc1] | 4-[2-(4-aminopiperidin-1-yl)-5-(4-ethoxyphenyl)-1-methyl-6-oxopyrimidin-4-yl]-2-fluorobenzonitrile |
| 96 | 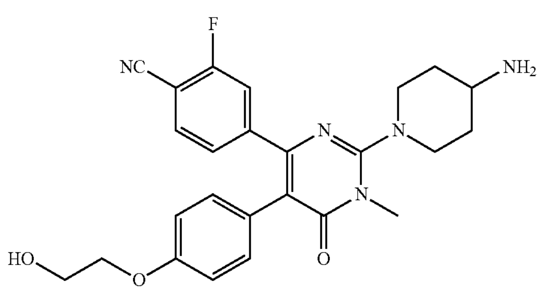 [SMILES: Cn1c(N2CCC(N)CC2)nc(-c2ccc(C#N)c(F)c2)c(-c2ccc(OCCO)cc2)c1=O] | 4-[2-(4-aminopiperidin-1-yl)-5-[4-(2-hydroxyethoxy)phenyl]-1-methyl-6-oxopyrimidin-4-yl]-2-fluorobenzonitrile |
| 97 | 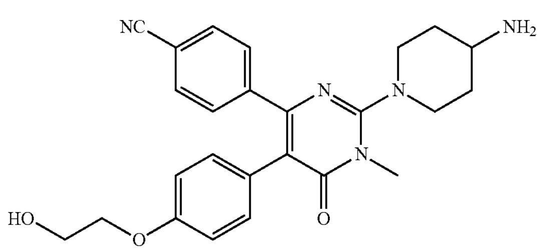 [SMILES: Cn1c(N2CCC(N)CC2)nc(-c2ccc(C#N)cc2)c(-c2ccc(OCCO)cc2)c1=O] | 4-[2-(4-aminopiperidin-1-yl)-5-[4-(2-hydroxyethoxy)phenyl]-1-methyl-6-oxopyrimidin-4-yl]benzonitrile |

TABLE 1-continued

| Chemical Synthesis Example | Structure | Name |
|---|---|---|
| 98 | 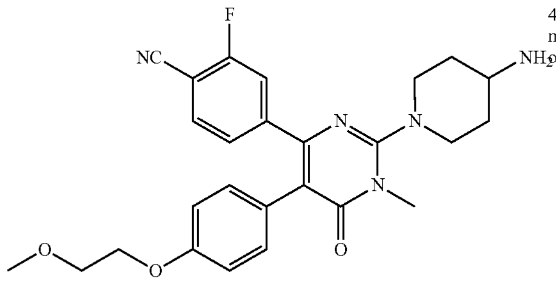 [SMILES: COCCOc1ccc(-c2c(-c3ccc(C#N)c(F)c3)nc(N3CCC(N)CC3)n(C)c2=O)cc1] | 4-[2-(4-aminopiperidin-1-yl)-5-{4-(2-methoxyethoxy)phenyl}-1-methyl-6-oxopyrimidin-4-yl]-2-fluorobenzonitrile |
| 99 | 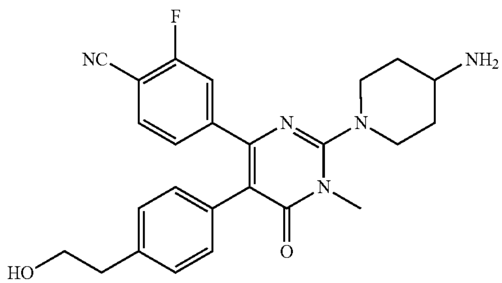 [SMILES: Cn1c(N2CCC(N)CC2)nc(-c2ccc(C#N)c(F)c2)c(-c2ccc(CCO)cc2)c1=O] | 4-[2-(4-aminopiperidin-1-yl)-5-[4-(2-hydroxyethyl)phenyl]-1-methyl-6-oxopyrimidin-4-yl]-2-fluorobenzonitrile |
| 100 | 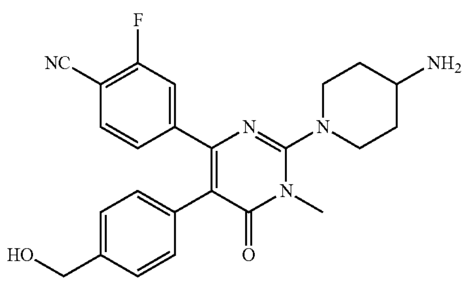 | 4-[2-(4-aminopiperidin-1-yl)-5-[4-(hydroxymethyl)phenyl]-1-methyl-6-oxopyrimidin-4-yl]-2-fluorobenzonitrile |
| 101 | 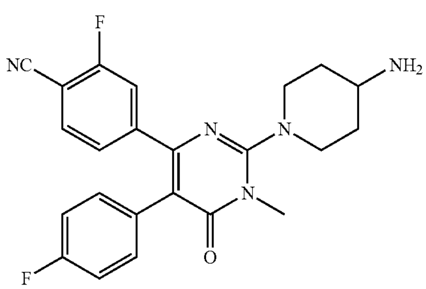 | 4-[2-(4-aminopiperidin-1-yl)-5-(4-fluorophenyl)-1-methyl-6-oxopyrimidin-4-yl]-2-fluorobenzonitrile |
| 102 | 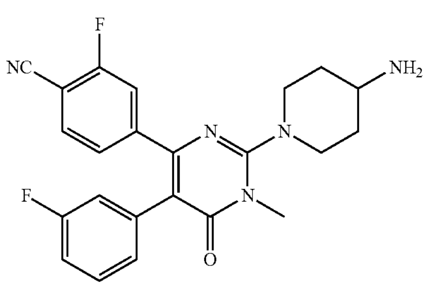 [SMILES: Cn1c(N2CCC(N)CC2)nc(-c2ccc(C#N)c(F)c2)c(-c2cccc(F)c2)c1=O] | 4-[2-(4-aminopiperidin-1-yl)-5-(3-fluorophenyl)-1-methyl-6-oxopyrimidin-4-yl]-2-fluorobenzonitrile |

TABLE 1-continued

| Chemical Synthesis Example | Structure | Name |
|---|---|---|
| 103 | 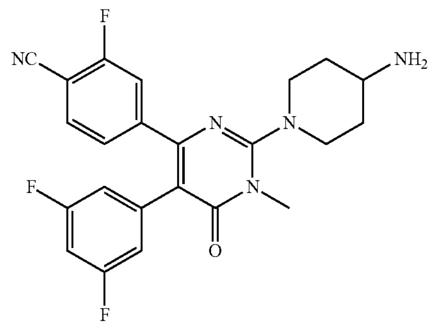 [SMILES: Cn1c(N2CCC(N)CC2)nc(-c2ccc(C#N)c(F)c2)c(-c2cc(F)cc(F)c2)c1=O] | 4-[2-(4-aminopiperidin-1-yl)-5-(3,5-difluorophenyl)-1-methyl-6-oxopyrimidin-4-yl]-2-fluorobenzonitrile |
| 104 | 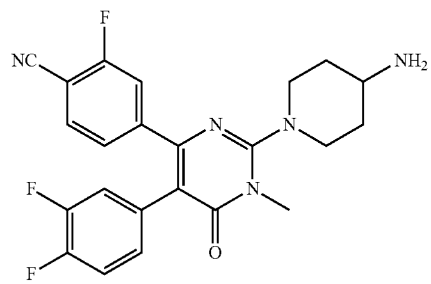 [SMILES: Cn1c(N2CCC(N)CC2)nc(-c2ccc(C#N)c(F)c2)c(-c2ccc(F)c(F)c2)c1=O] | 4-[2-(4-aminopiperidin-1-yl)-5-(3,4-difluorophenyl)-1-methyl-6-oxopyrimidin-4-yl]-2-fluorobenzonitrile |
| 105 | 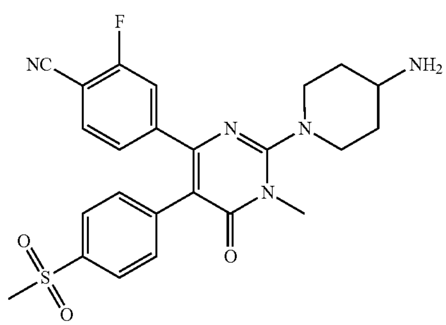 [SMILES: Cn1c(N2CCC(N)CC2)nc(-c2ccc(C#N)c(F)c2)c(-c2ccc(S(C)(=O)=O)cc2)c1=O] | 4-[2-(4-aminopiperidin-1-yl)-1-methyl-5-(4-methylsulfonylphenyl)-6-oxopyrimidin-4-yl]-2-fluorobenzonitrile |
| 106 | 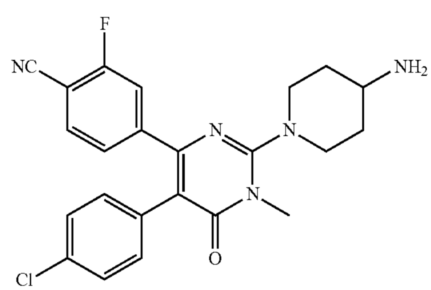 [SMILES: Cn1c(N2CCC(N)CC2)nc(-c2ccc(C#N)c(F)c2)c(-c2ccc(Cl)cc2)c1=O] | 4-[2-(4-aminopiperidin-1-yl-5-(4-chlorophenyl)-1-methyl-6-oxopyrimidin-4-yl]-2-fluorobenzonitrile |
| 107 | 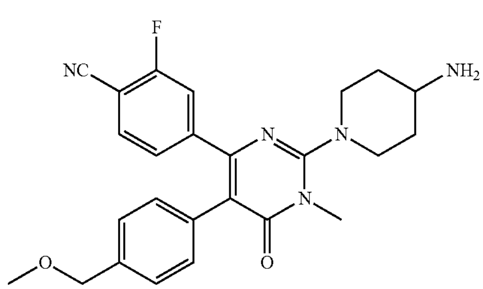 [SMILES: COCc1ccc(-c2c(-c3ccc(C#N)c(F)c3)nc(N3CCC(N)CC3)n(C)c2=O)cc1] | 4-[2-(4-aminopiperidin-1-yl)-5-[4-(methoxymethyl)phenyl]-1-methyl-6-oxopyrimidin-4-yl]-2-fluorobenzonitrile |

TABLE 1-continued

| Chemical Synthesis Example | Structure | Name |
|---|---|---|
| 108 | 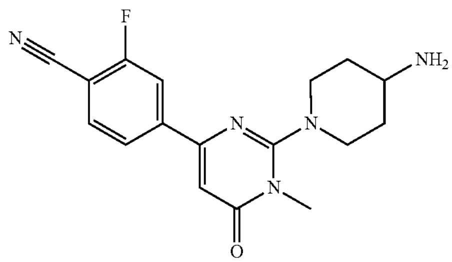 [SMILES: Cn1c(N2CCC(N)CC2)nc(-c2ccc(C#N)c(F)c2)cc1=O] | 4-[2-(4-aminopiperidin-1-yl)-1-methyl-6-oxopyrimidin-4-yl]-2-fluorobenzonitrile |
| 109 | 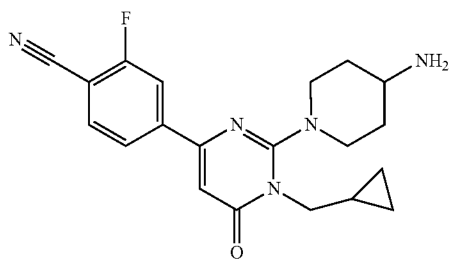 [SMILES: N#Cc1ccc(-c2cc(=O)n(CC3CC3)c(N3CCC(N)CC3)n2)cc1F] | 4-[2-(4-amino-piperidin-1-yl)-1-cyclopropylmethyl-6-oxo-1,6-dihydro-pyrimidin-4-yl]-2-fluoro-benzonitrile |
| 110 | 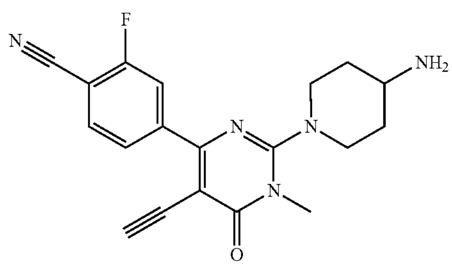 [SMILES: C#Cc1c(-c2ccc(C#N)c(F)c2)nc(N2CCC(N)CC2)n(C)c1=O] | 4-[2-(4-amino-piperidin-1-yl)-1-cyclopropylmethyl-6-oxo-1,6-dihydro-pyrimidin-4-yl]-2-fluoro-benzonitrile |
| 111 | 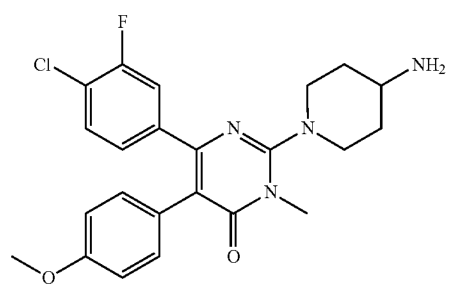 [SMILES: COc1ccc(-c2c(-c3ccc(Cl)c(F)c3)nc(N3CCC(N)CC3)n(C)c2=O)cc1] | 2-(4-amino-piperidin-1-yl)-6-(4-chloro-3-fluoro-phenyl)-5-(4-methoxy-phenyl)-3-methyl-3H-pyrimidin-4-one |
| 112 | 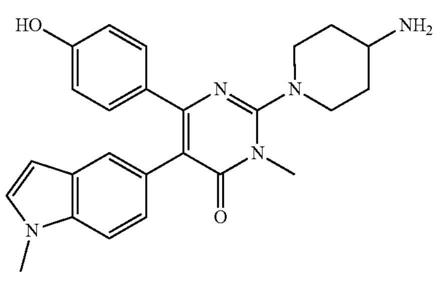 [SMILES: Cn1c(N2CCC(N)CC2)nc(-c2ccc(O)cc2)c(-c2ccc3c(ccn3C)c2)c1=O] | 2-(4-amino-piperidin-1-yl)-6-(4-hydroxy-phenyl)-3-methyl-5-(1-methyl-1H-indol-5-yl)-3H-pyrimidin-4-one |

TABLE 1-continued

| Chemical Synthesis Example | Structure | Name |
|---|---|---|
| 113 | 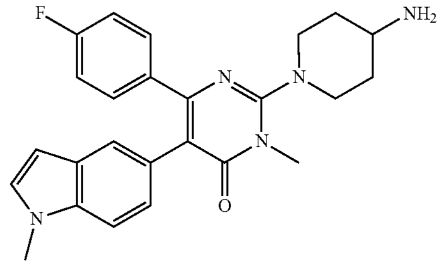 [SMILES: Cn1c(N2CCC(N)CC2)nc(-c2ccc(F)cc2)c(-c2ccc3c(ccn3C)c2)c1=O] | 2-(4-amino-piperidin-1-yl)-6-(4-fluoro-phenyl)-3-methyl-5-(1-methyl-1H-indol-5-yl)-3H-pyrimidin-4-one |
| 114 | 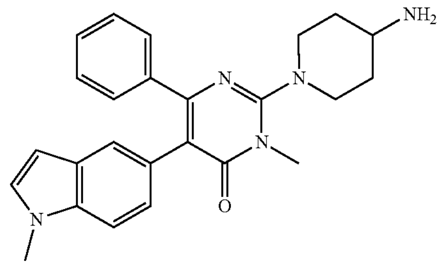 [SMILES: Cn1c(N2CCC(N)CC2)nc(-c2ccccc2)c(-c2ccc3c(ccn3C)c2)c1=O] | 2-(4-amino-piperidin-1-yl)-3-methyl-5-(1-methyl-1H-indol-5-yl)-6-phenyl-3H-pyrimidin-4-one |
| 115 | 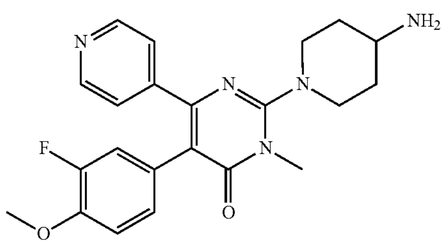 [SMILES: COc1ccc(-c2c(-c3ccncc3)nc(N3CCC(N)CC3)n(C)c2=O)cc1F] | 2-(4-amino-piperidin-1-yl)-5-(3-fluoro-4-methoxy-phenyl)-3-methyl-6-pyridin-4-yl-3H-pyrimidin-4-one |
| 116 | 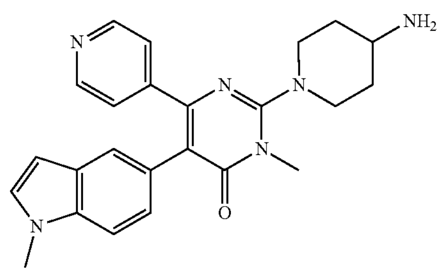 | 2-(4-amino-piperidin-1-yl)-3-methyl-5-(1-methyl-1H-indol-5-yl)-6-pyridin-4-yl-3H-pyrimidin-4-one |
| 117 | 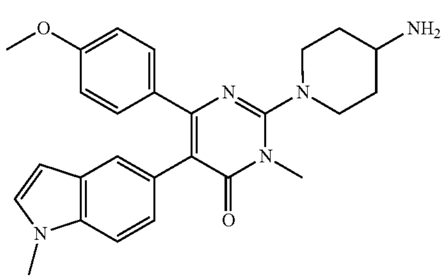 [SMILES: COc1ccc(-c2nc(N3CCC(N)CC3)n(C)c(=O)c2-c2ccc3c(ccn3C)c2)cc1] | 2-(4-amino-piperidin-1-yl)-6-(4-methoxy-phenyl)-3-methyl-5-(1-methyl-1H-indol-5-yl)-3H-pyrimidin-4-one |

TABLE 1-continued

| Chemical Synthesis Example | Structure | Name |
|---|---|---|
| 118 | 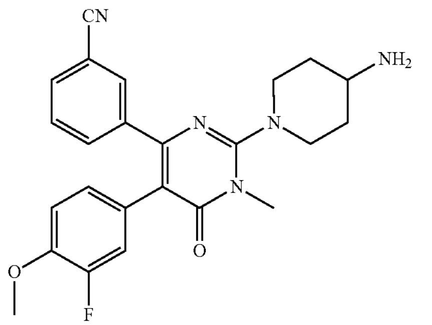 [SMILES: COc1ccc(-c2c(-c3cccc(C#N)c3)nc(N3CCC(N)CC3)n(C)c2=O)cc1F] | 3-[2-(4-aminopiperidin-1-yl)-5-(3-fluoro-4-methoxyphenyl)-1-methyl-6-oxopyrimidin-4-yl]benzonitrile |
| 119 | 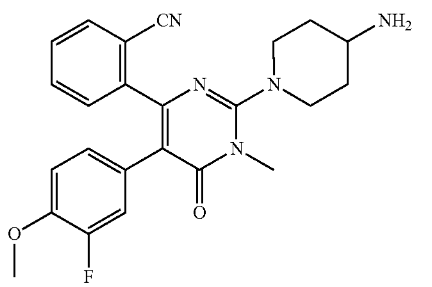 [SMILES: COc1ccc(-c2c(-c3ccccc3C#N)nc(N3CCC(N)CC3)n(C)c2=O)cc1F] | 2-[2-(4-aminopiperidin-1-yl)-5-(3-fluoro-4-methoxyphenyl)-1-methyl-6-oxopyrimidin-4-yl]benzonitrile |
| 120 | 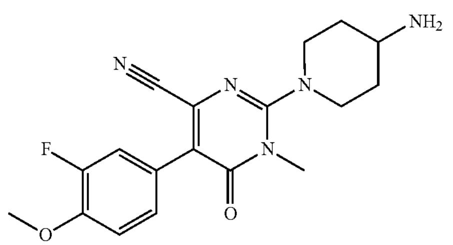 [SMILES: COc1ccc(-c2c(C#N)nc(N3CCC(N)CC3)n(C)c2=O)cc1F] | 2-(4-amino-piperidin-1-yl)-5-(3-fluoro-4-methoxy-phenyl)-1-methyl-6-oxo-1,6-dihydro-pyrimidine-4-carbonitrile |
| 121 | 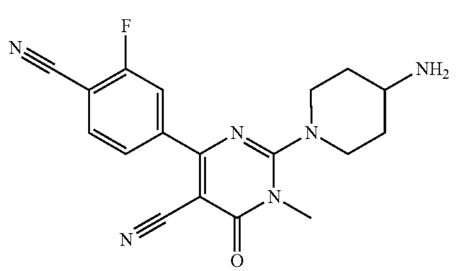 [SMILES: Cn1c(N2CCC(N)CC2)nc(-c2ccc(C#N)c(F)c2)c(C#N)c1=O] | 2-(4-amino-piperidin-1-yl)-4-(4-cyano-3-fluoro-phenyl)-1-methyl-6-oxo-1,6-dihydro-pyrimidine-5-carbonitrile |
| 122 | 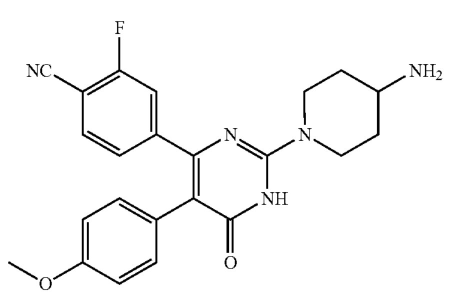 [SMILES: COc1ccc(-c2c(-c3ccc(C#N)c(F)c3)nc(N3CCC(N)CC3)[nH]c2=O)cc1] | 4-[2-(4-aminopiperidin-1-yl)-5-(4-methoxyphenyl)-6-oxo-1H-pyrimidin-4-yl]-2-fluorobenzonitrile |

In some embodiments, the substituted heterocyclic derivative compound described herein has the structure provided in Table 2.
TABLE 2
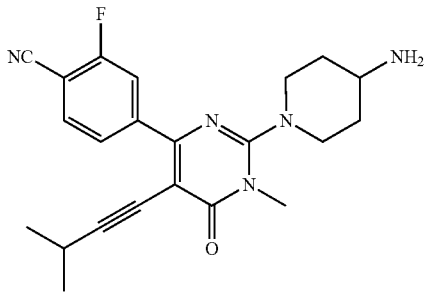 [SMILES: CC(C)C#Cc1c(-c2ccc(C#N)c(F)c2)nc(N2CCC(N)CC2)n(C)c1=O]
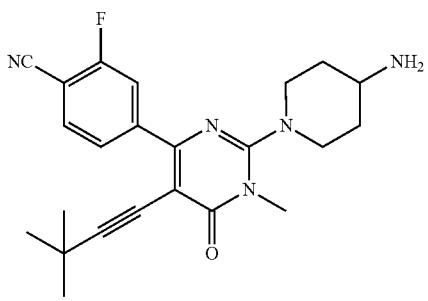 [SMILES: Cn1c(N2CCC(N)CC2)nc(-c2ccc(C#N)c(F)c2)c(C#CC(C)(C)C)c1=O]
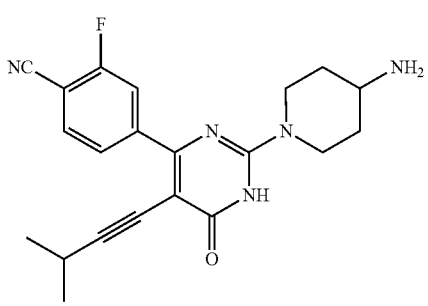
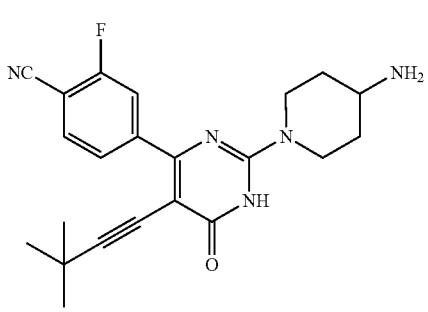 [SMILES: CC(C)C#Cc1c(-c2ccc(C#N)c(F)c2)nc(N2CCC(N)CC2)[nH]c1=O]
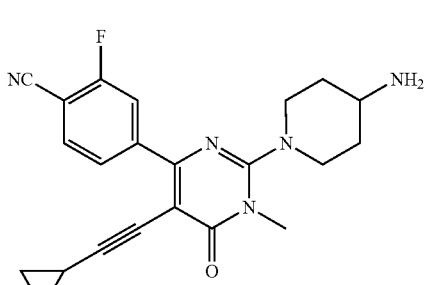
TABLE 2-continued
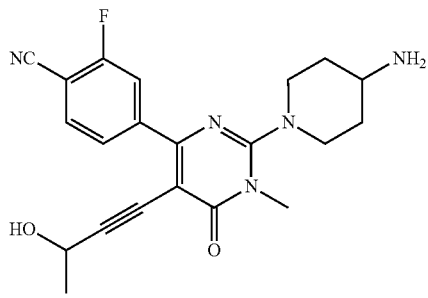
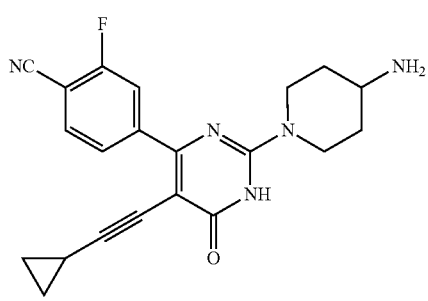 [SMILES: N#Cc1ccc(-c2nc(N3CCC(N)CC3)[nH]c(=O)c2C#CC2CC2)cc1F]
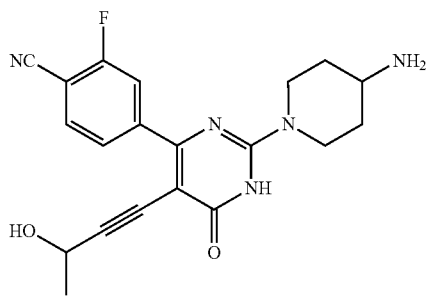
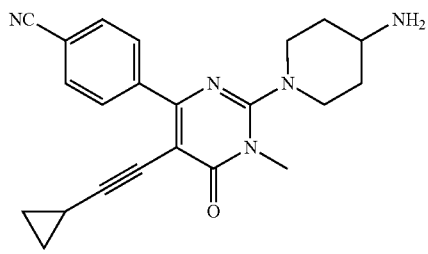 [SMILES: Cn1c(N2CCC(N)CC2)nc(-c2ccc(C#N)cc2)c(C#CC2CC2)c1=O]
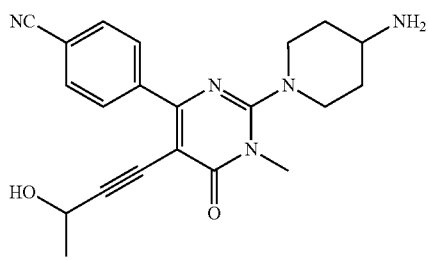

TABLE 2-continued
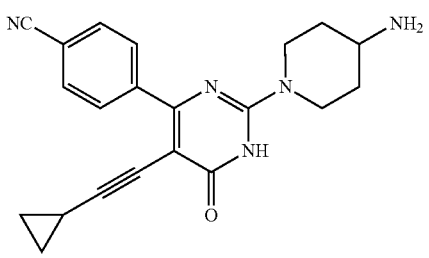 [SMILES: N#Cc1ccc(-c2nc(N3CCC(N)CC3)[nH]c(=O)c2C#CC2CC2)cc1]
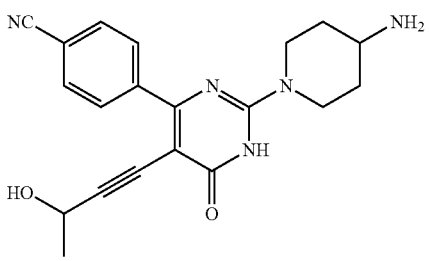
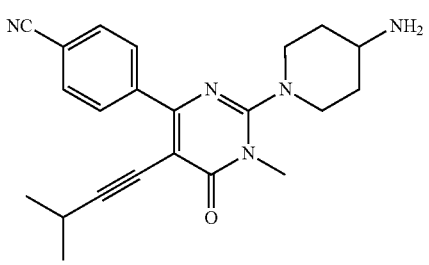 [SMILES: CC(C)C#Cc1c(-c2ccc(C#N)cc2)nc(N2CCC(N)CC2)n(C)c1=O]
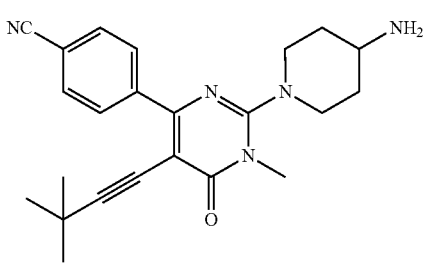 [SMILES: Cn1c(N2CCC(N)CC2)nc(-c2ccc(C#N)cc2)c(C#CC(C)(C)C)c1=O]
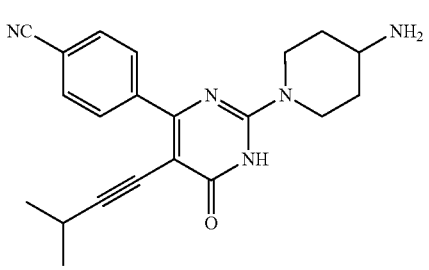
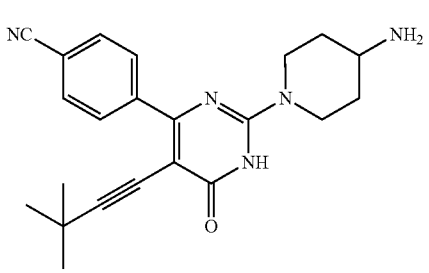 [SMILES: CC(C)(C)C#Cc1c(-c2ccc(C#N)cc2)nc(N2CCC(N)CC2)[nH]c1=O]
TABLE 2-continued
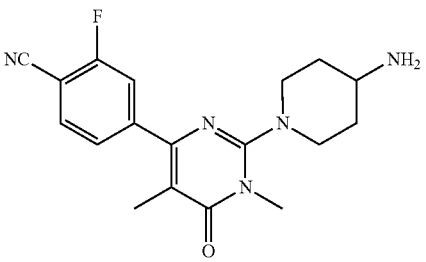 [SMILES: Cc1c(-c2ccc(C#N)c(F)c2)nc(N2CCC(N)CC2)n(C)c1=O]
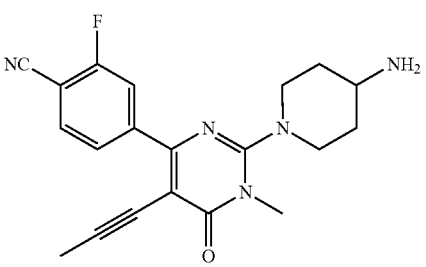 [SMILES: CC#Cc1c(-c2ccc(C#N)c(F)c2)nc(N2CCC(N)CC2)n(C)c1=O]
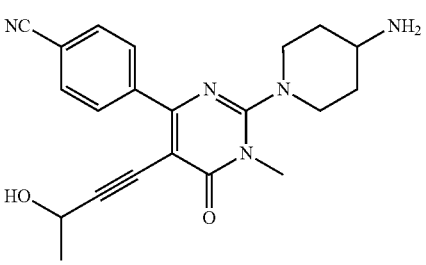
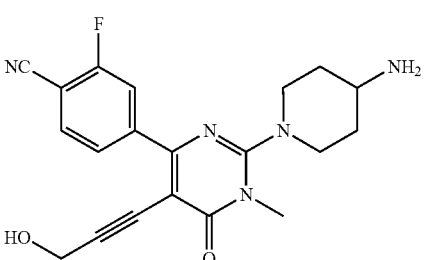
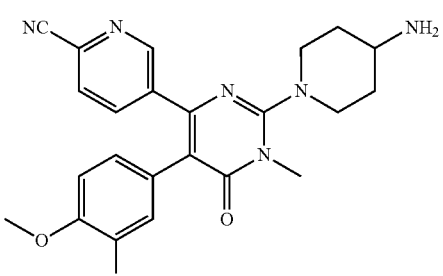
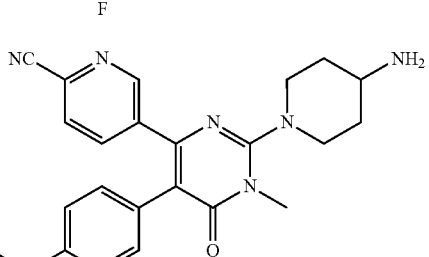

TABLE 2-continued
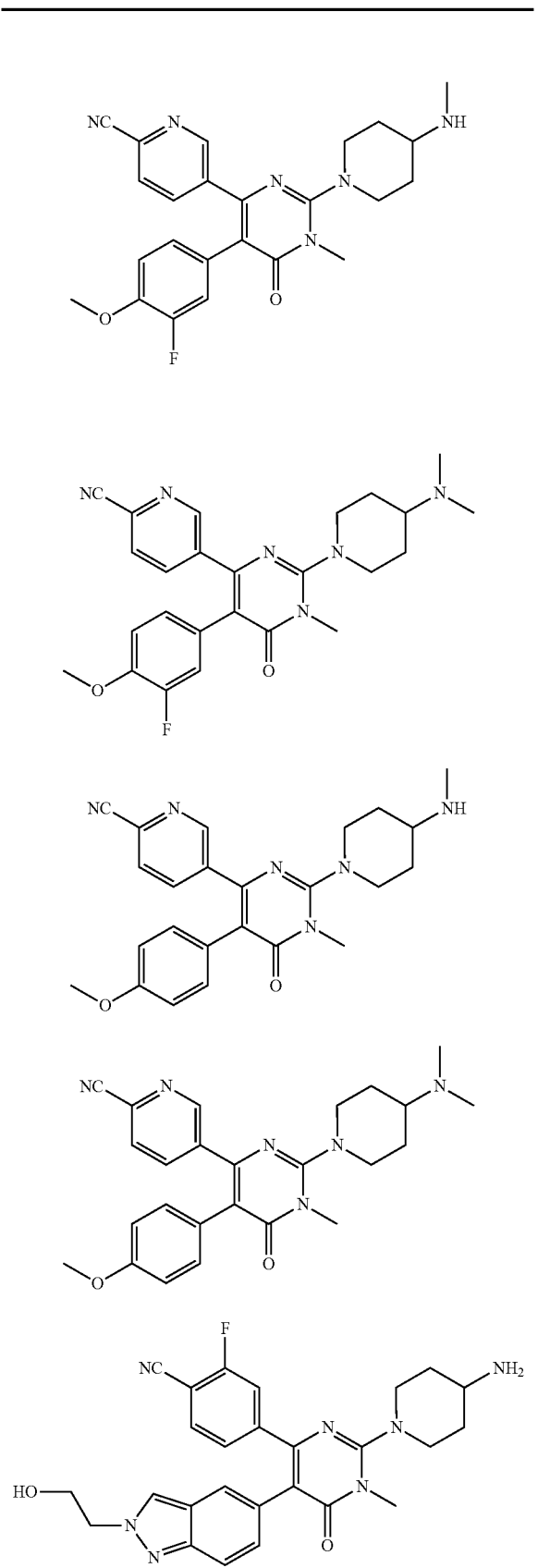
TABLE 2-continued
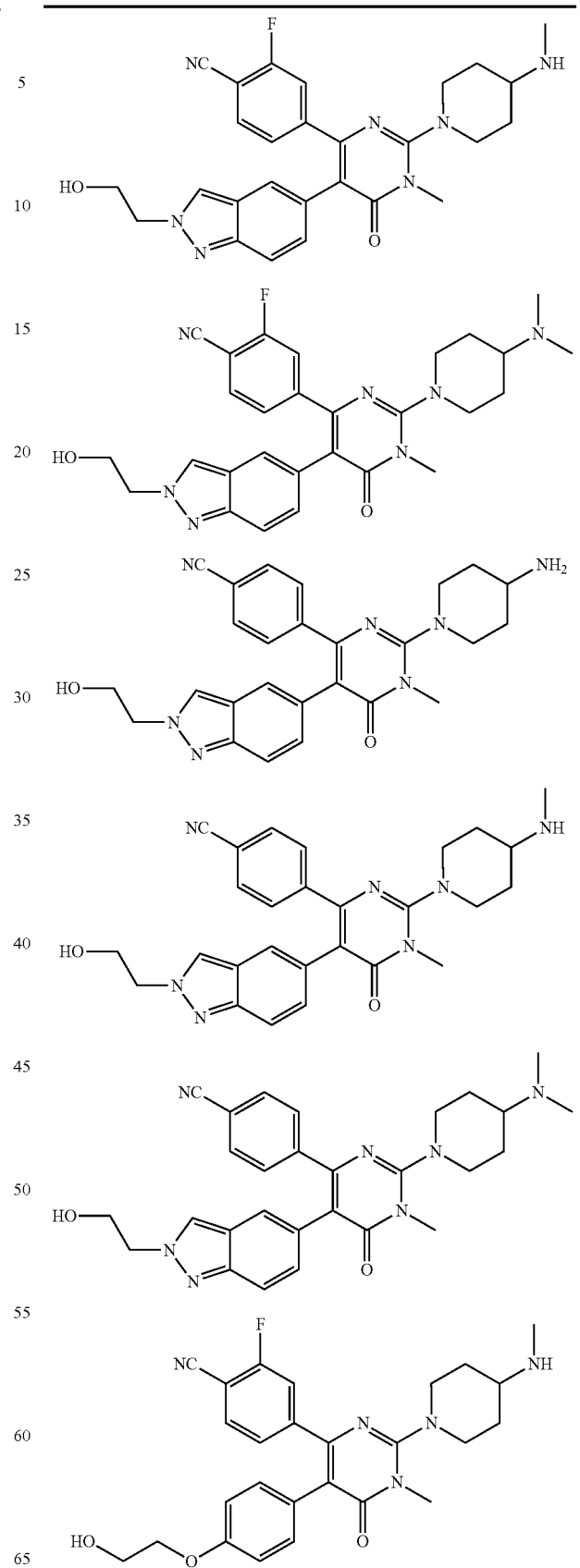

TABLE 2-continued
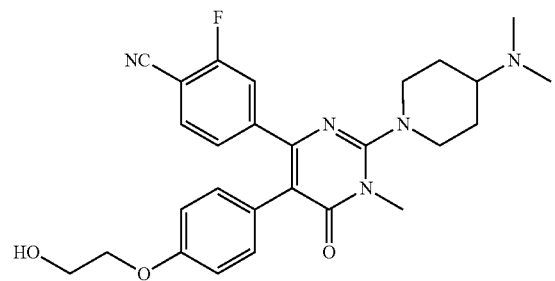 [SMILES: CN(C)C1CCN(c2nc(-c3ccc(C#N)c(F)c3)c(-c3ccc(OCCO)cc3)c(=O)n2C)CC1]
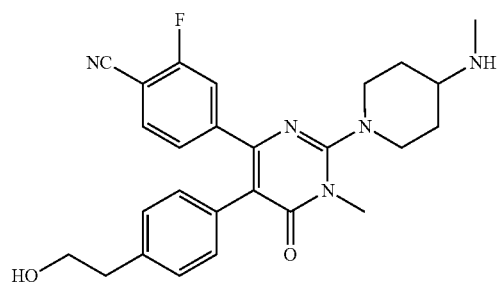 [SMILES: CNC1CCN(c2nc(-c3ccc(C#N)c(F)c3)c(-c3ccc(CCO)cc3)c(=O)n2C)CC1]
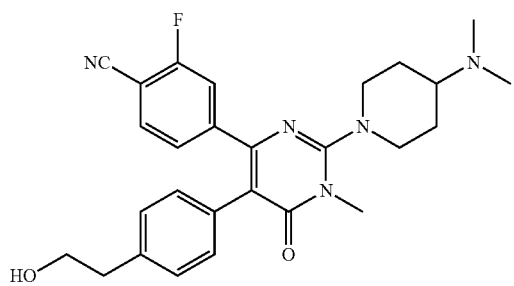 [SMILES: CN(C)C1CCN(c2nc(-c3ccc(C#N)c(F)c3)c(-c3ccc(CCO)cc3)c(=O)n2C)CC1]
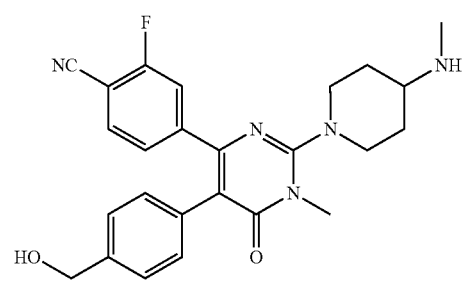 [SMILES: CNC1CCN(c2nc(-c3ccc(C#N)c(F)c3)c(-c3ccc(CO)cc3)c(=O)n2C)CC1]
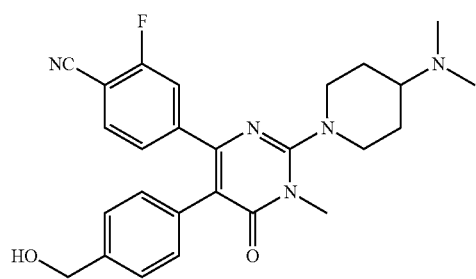 [SMILES: CN(C)C1CCN(c2nc(-c3ccc(C#N)c(F)c3)c(-c3ccc(CO)cc3)c(=O)n2C)CC1]
TABLE 2-continued
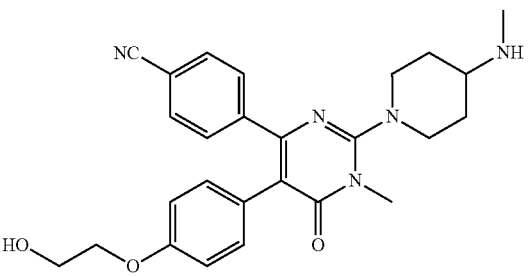 [SMILES: CNC1CCN(c2nc(-c3ccc(C#N)cc3)c(-c3ccc(OCCO)cc3)c(=O)n2C)CC1]
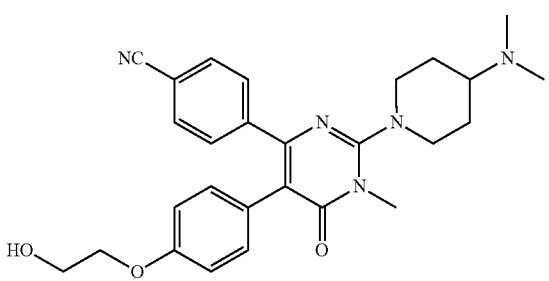 [SMILES: CN(C)C1CCN(c2nc(-c3ccc(C#N)cc3)c(-c3ccc(OCCO)cc3)c(=O)n2C)CC1]
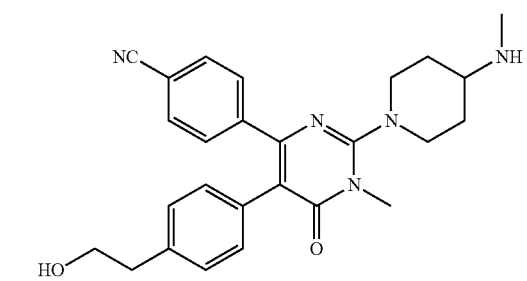 [SMILES: CNC1CCN(c2nc(-c3ccc(C#N)cc3)c(-c3ccc(CCO)cc3)c(=O)n2C)CC1]
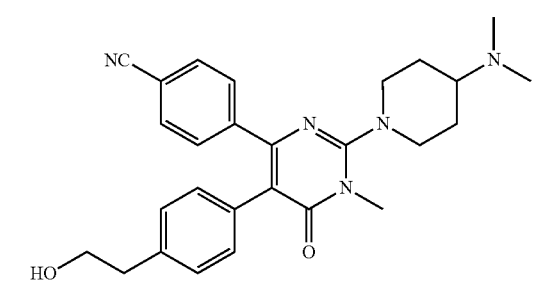
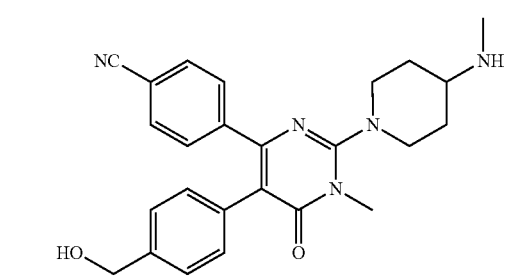 [SMILES: CNC1CCN(c2nc(-c3ccc(C#N)cc3)c(-c3ccc(CO)cc3)c(=O)n2C)CC1]

TABLE 2-continued
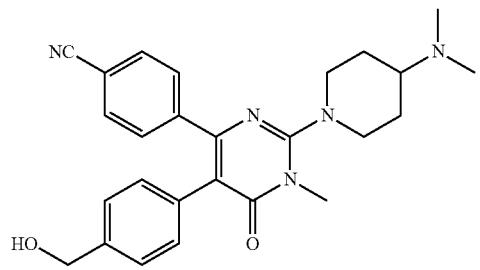 [SMILES: CN(C)C1CCN(c2nc(-c3ccc(C#N)cc3)c(-c3ccc(CO)cc3)c(=O)n2C)CC1]
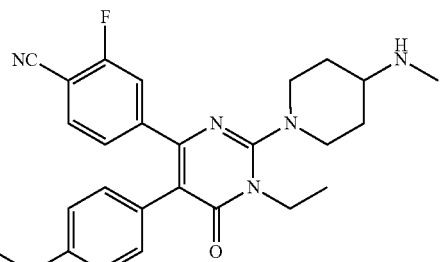
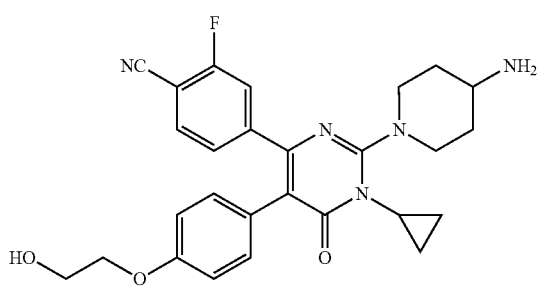 [SMILES: N#Cc1ccc(-c2nc(N3CCC(N)CC3)n(C3CC3)c(=O)c2-c2ccc(OCCO)cc2)cc1F]
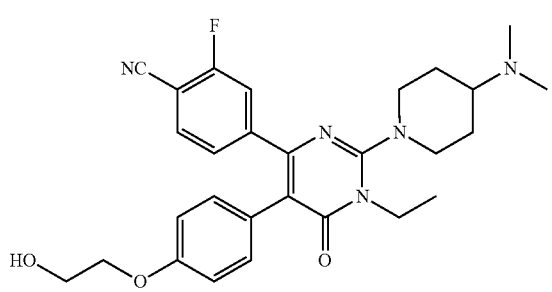
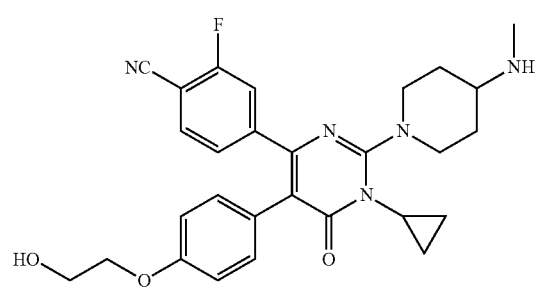 [SMILES: CNC1CCN(c2nc(-c3ccc(C#N)c(F)c3)c(-c3ccc(OCCO)cc3)c(=O)n2C2CC2)CC1]
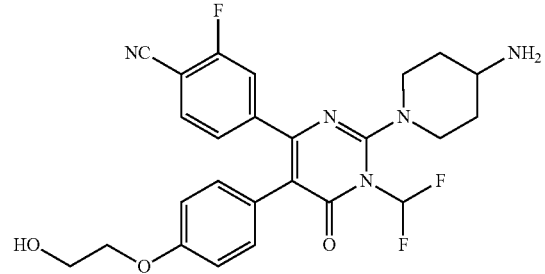
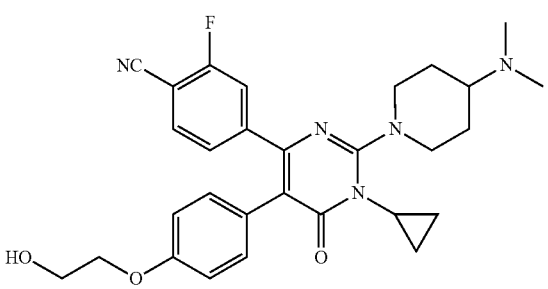 [SMILES: CN(C)C1CCN(c2nc(-c3ccc(C#N)c(F)c3)c(-c3ccc(OCCO)cc3)c(=O)n2C2CC2)CC1]
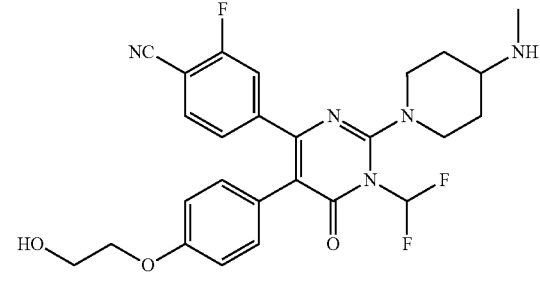
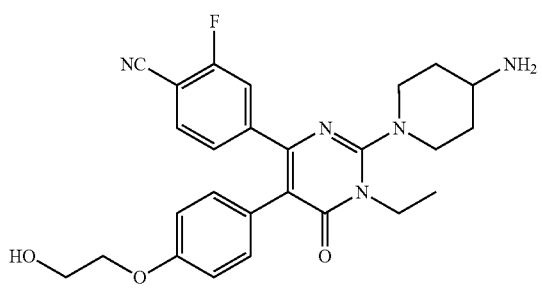 [SMILES: CCn1c(N2CCC(N)CC2)nc(-c2ccc(C#N)c(F)c2)c(-c2ccc(OCCO)cc2)c1=O]
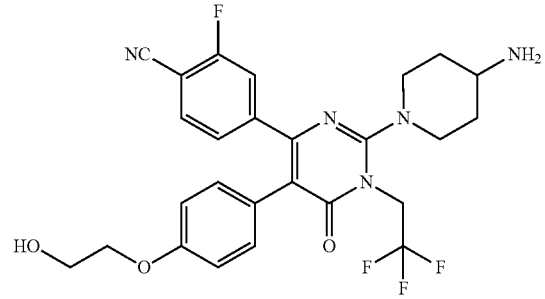 [SMILES: N#Cc1ccc(-c2nc(N3CCC(N)CC3)n(CC(F)(F)F)c(=O)c2-c2ccc(OCCO)cc2)cc1F]

TABLE 2-continued
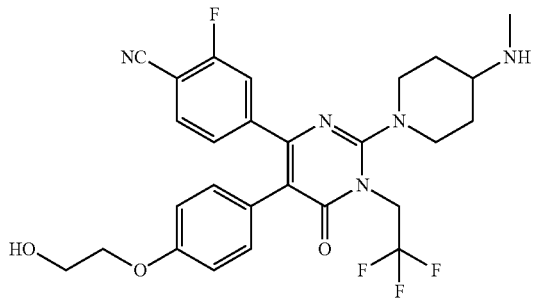 [SMILES: CNC1CCN(c2nc(-c3ccc(C#N)c(F)c3)c(-c3ccc(OCCO)cc3)c(=O)n2CC(F)(F)F)CC1]
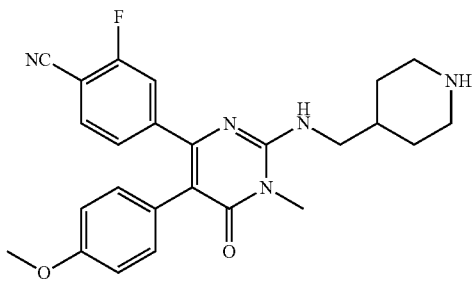
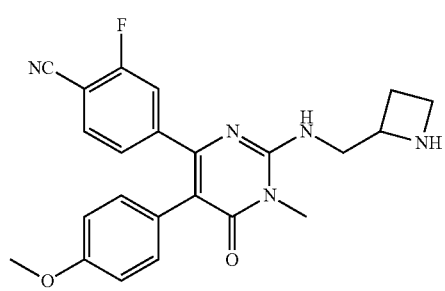 [SMILES: COc1ccc(-c2c(-c3ccc(C#N)c(F)c3)nc(NCC3CCN3)n(C)c2=O)cc1]
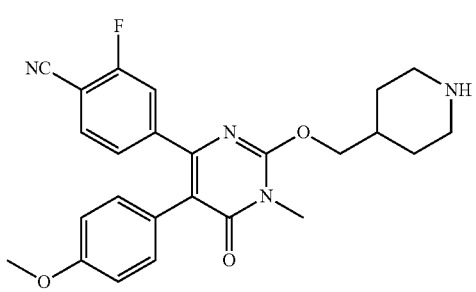
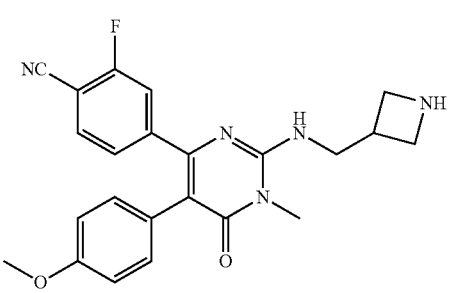 [SMILES: COc1ccc(-c2c(-c3ccc(C#N)c(F)c3)nc(NCC3CNC3)n(C)c2=O)cc1]
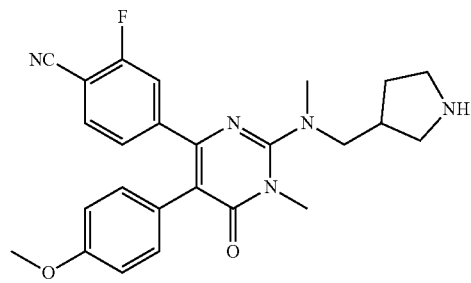
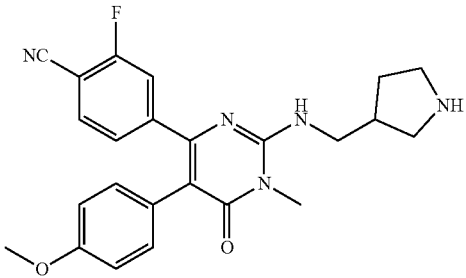 [SMILES: COc1ccc(-c2c(-c3ccc(C#N)c(F)c3)nc(NCC3CCNC3)n(C)c2=O)cc1]
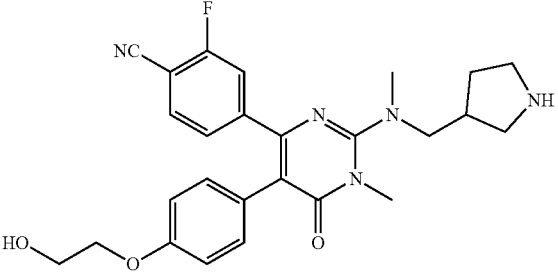 [SMILES: CN(CC1CCNC1)c1nc(-c2ccc(C#N)c(F)c2)c(-c2ccc(OCCO)cc2)c(=O)n1C]
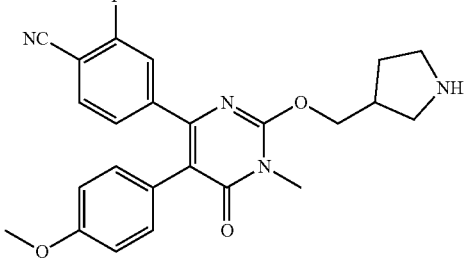
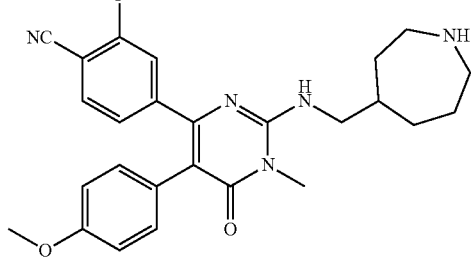

TABLE 2-continued
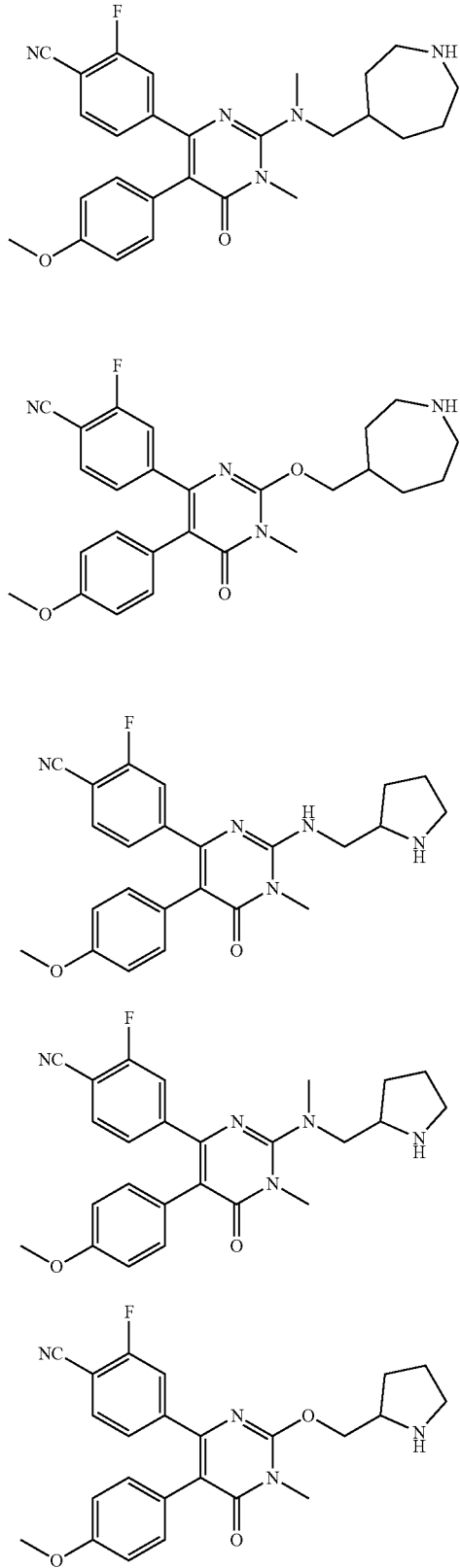
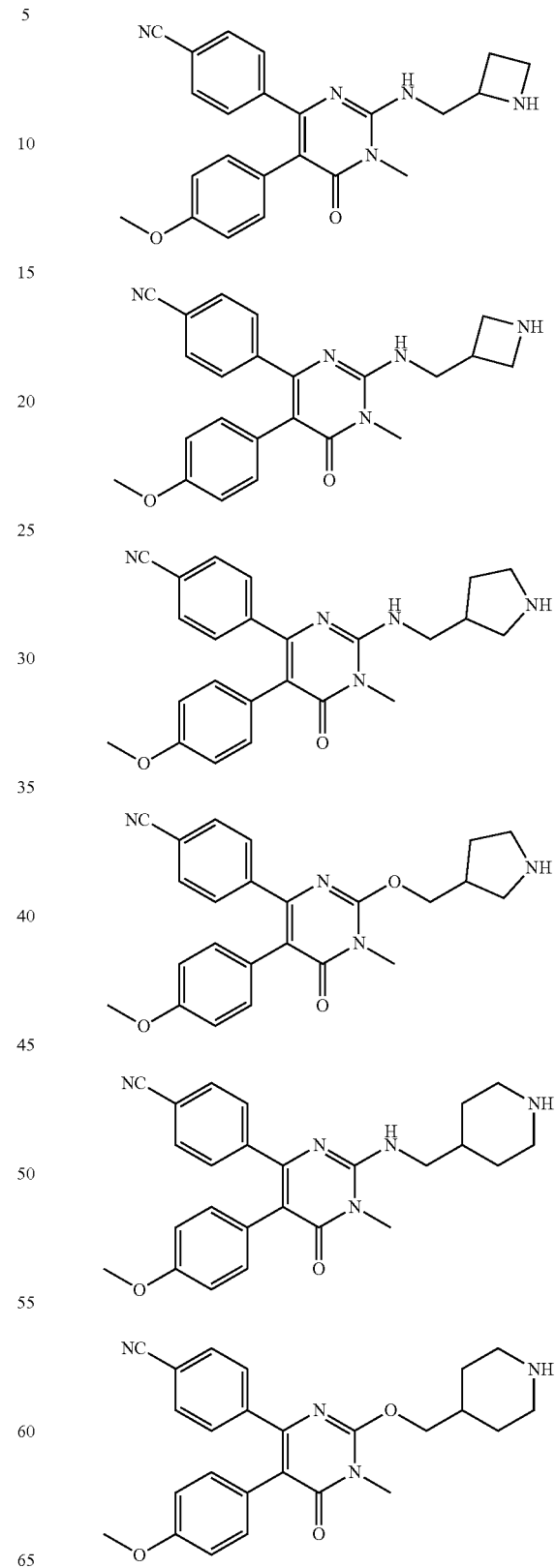

TABLE 2-continued
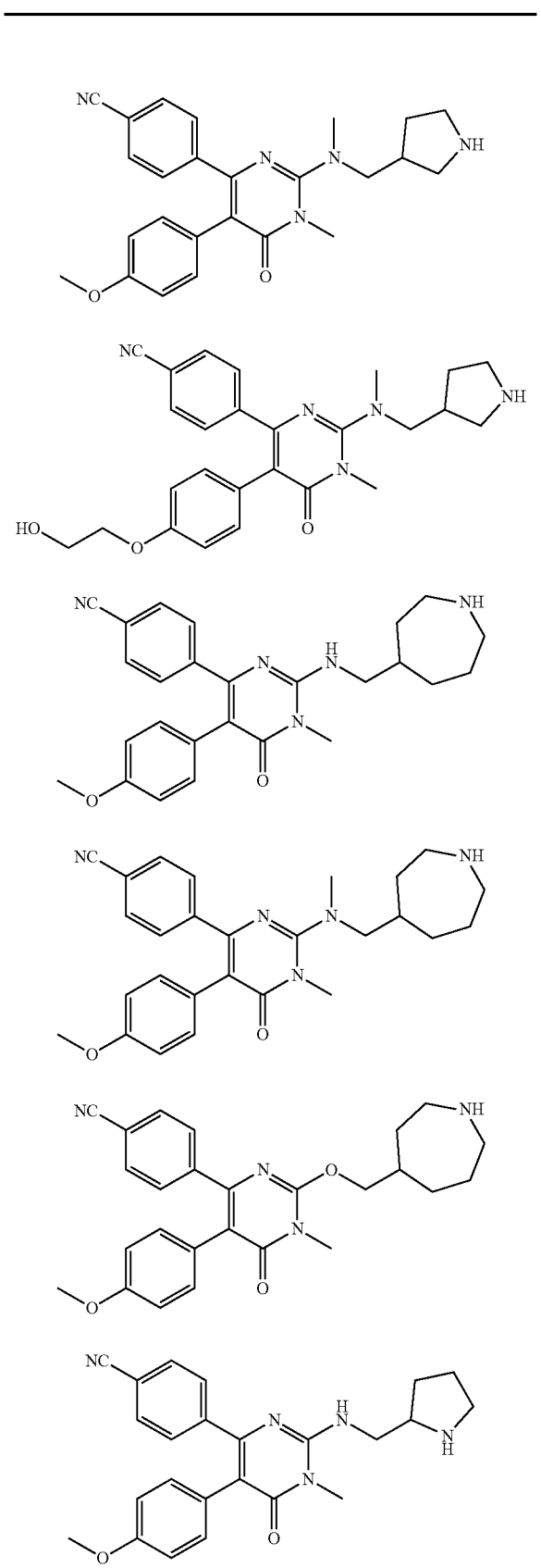
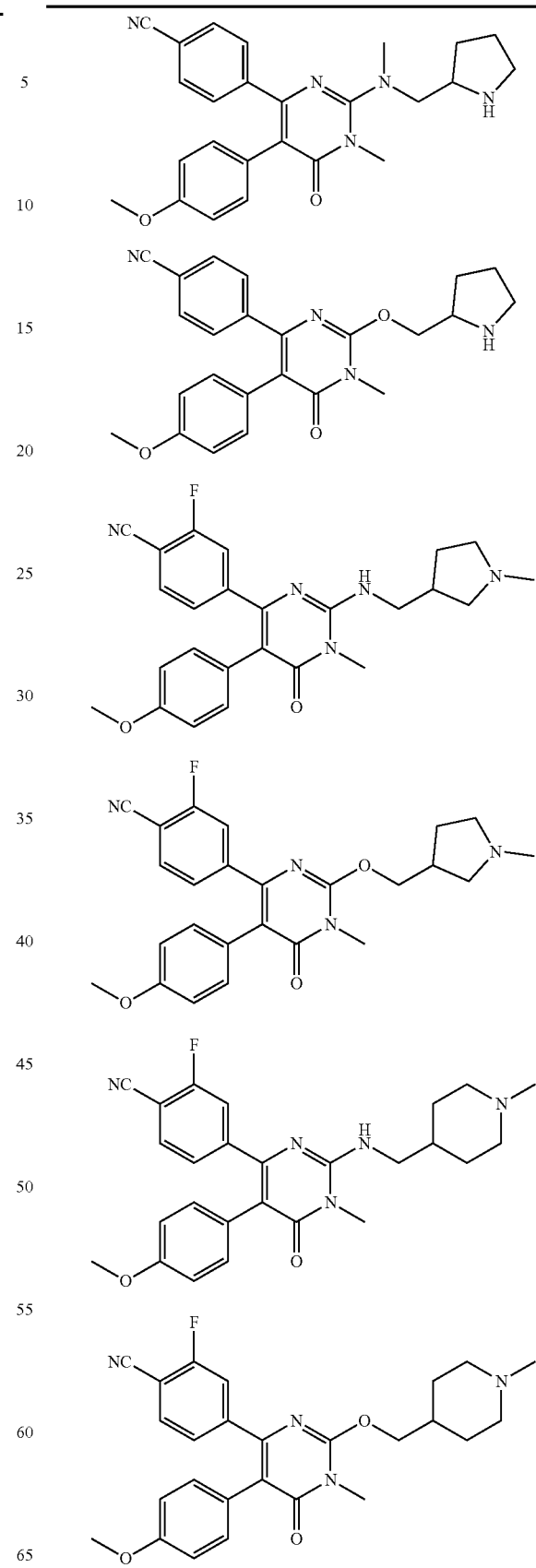

TABLE 2-continued
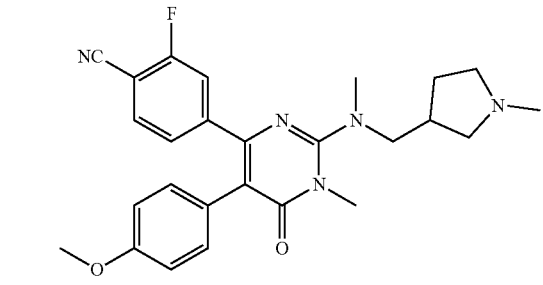
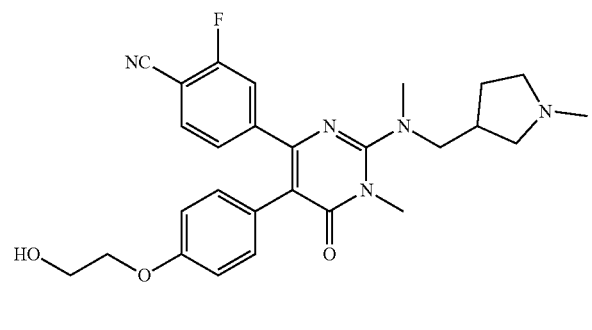 [SMILES: CN1CCC(CN(C)c2nc(-c3ccc(C#N)c(F)c3)c(-c3ccc(OCCO)cc3)c(=O)n2C)C1]
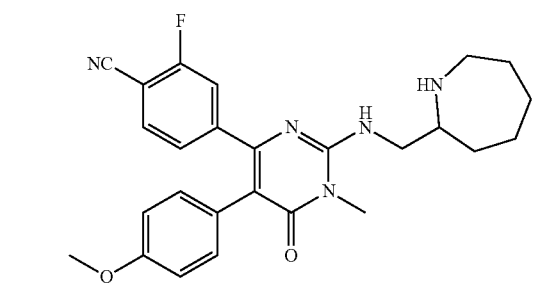 [SMILES: COc1ccc(-c2c(-c3ccc(C#N)c(F)c3)nc(NCC3CCCCCN3)n(C)c2=O)cc1]
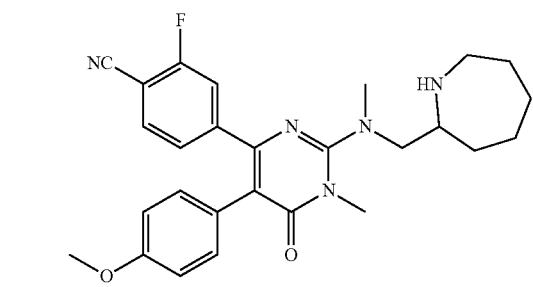 [SMILES: COc1ccc(-c2c(-c3ccc(C#N)c(F)c3)nc(N(C)CC3CCCCCN3)n(C)c2=O)cc1]
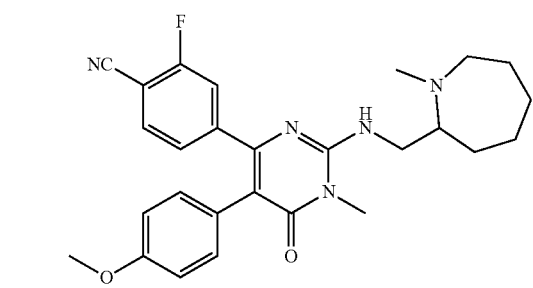 [SMILES: COc1ccc(-c2c(-c3ccc(C#N)c(F)c3)nc(NCC3CCCCCN3C)n(C)c2=O)cc1]
TABLE 2-continued
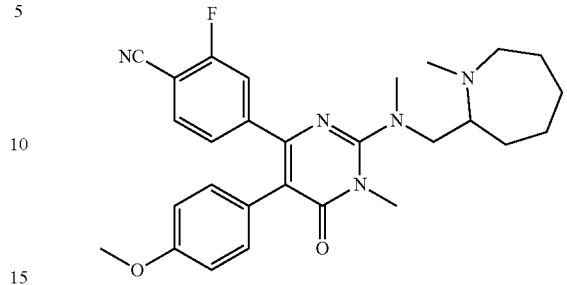
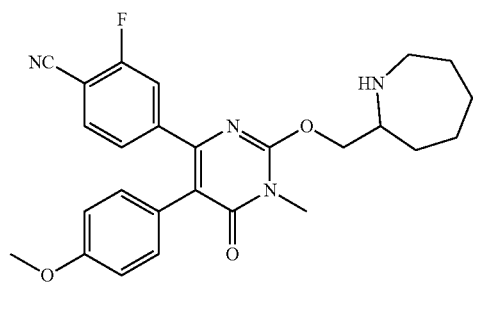 [SMILES: COc1ccc(-c2c(-c3ccc(C#N)c(F)c3)nc(OCC3CCCCCN3)n(C)c2=O)cc1]
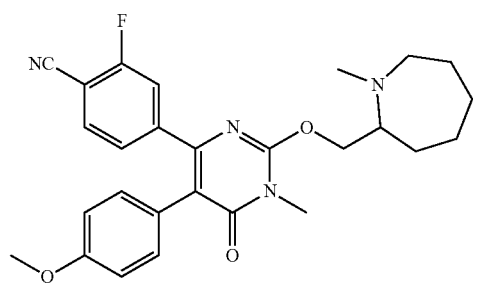 [SMILES: COc1ccc(-c2c(-c3ccc(C#N)c(F)c3)nc(OCC3CCCCCN3C)n(C)c2=O)cc1]
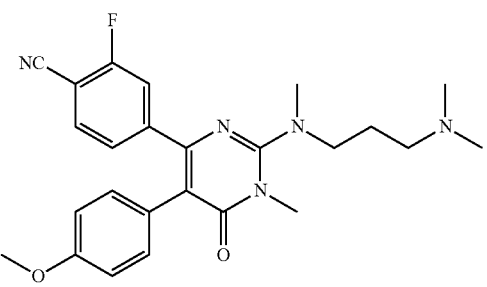
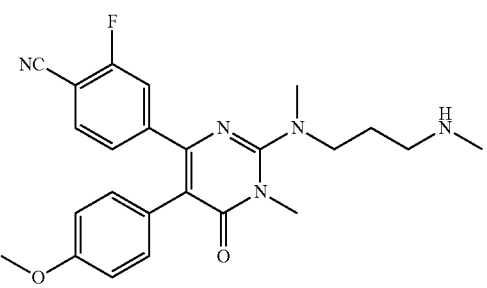

TABLE 2-continued
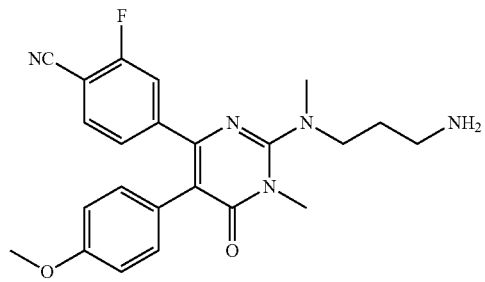 [SMILES: COc1ccc(-c2c(-c3ccc(C#N)c(F)c3)nc(N(C)CCCN)n(C)c2=O)cc1]
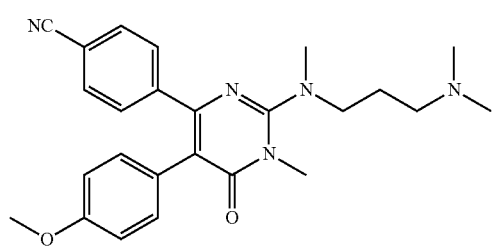
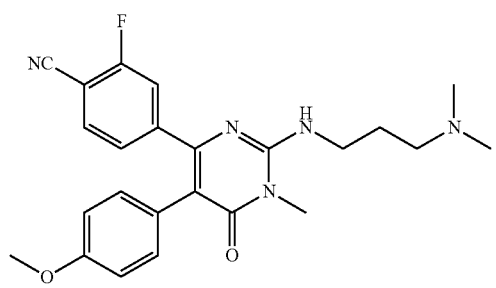
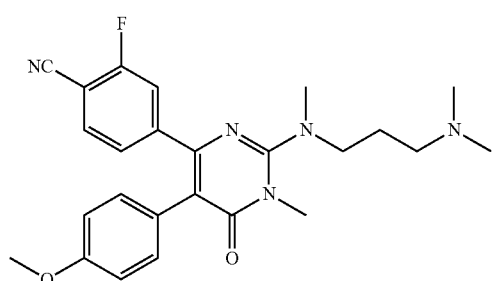
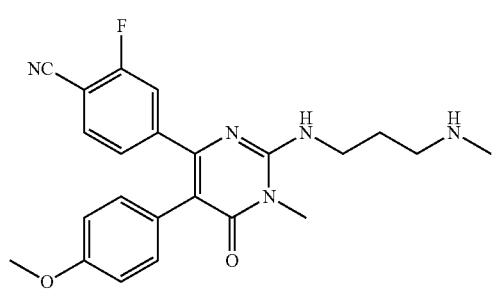
TABLE 2-continued
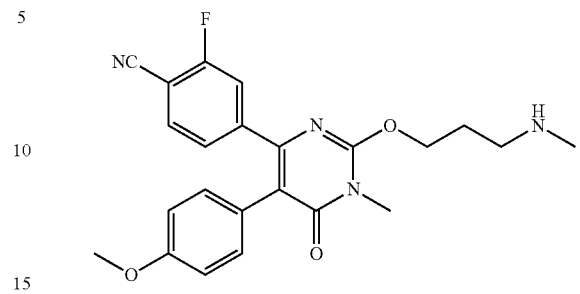
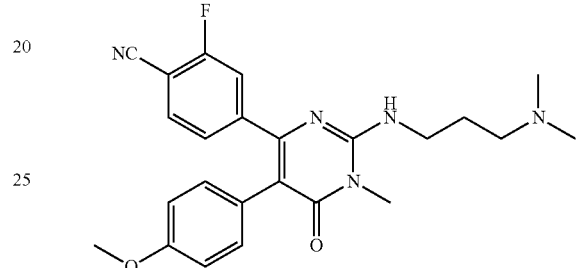
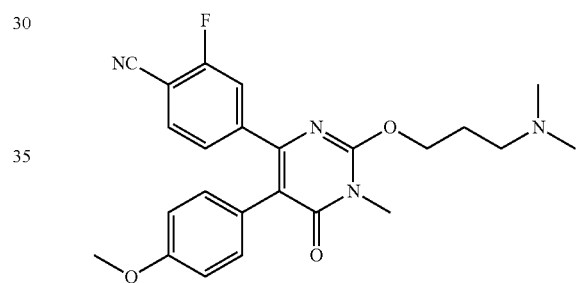
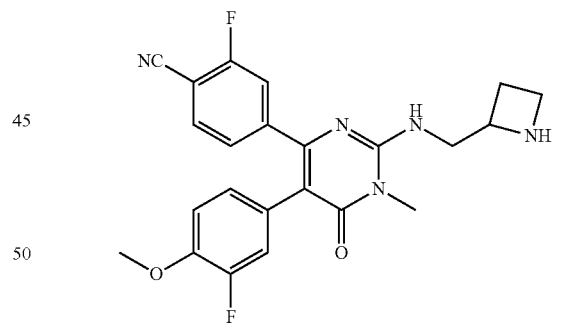
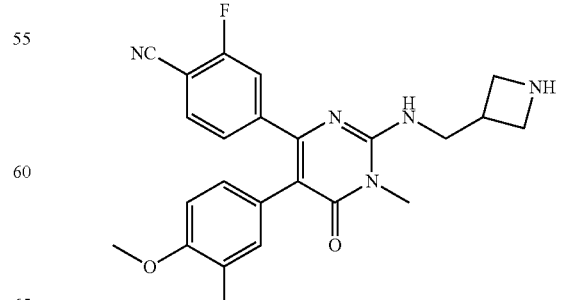

TABLE 2-continued
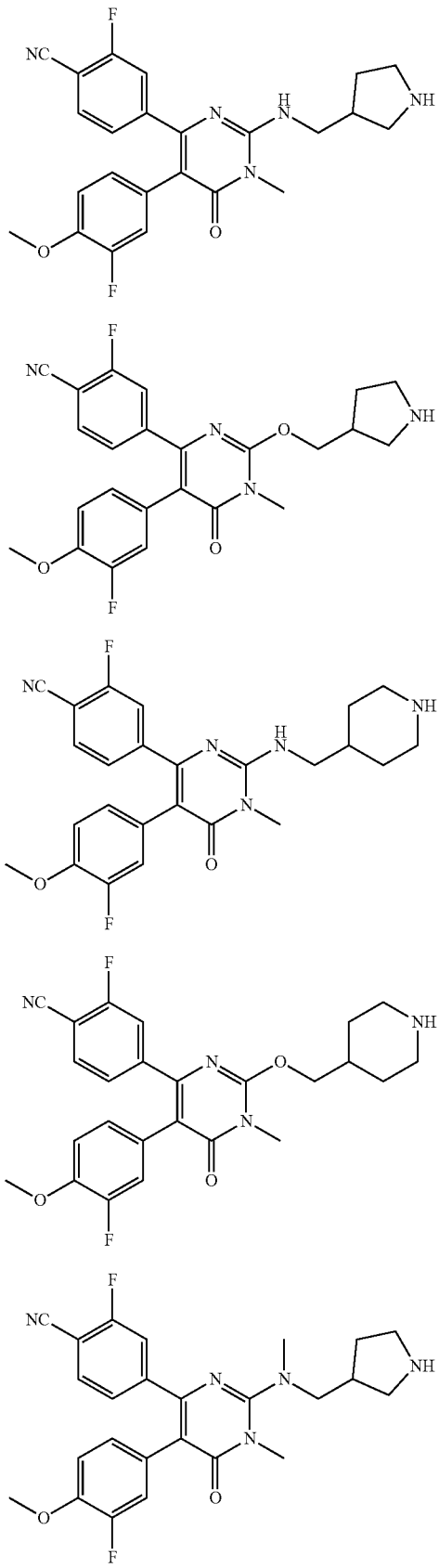
TABLE 2-continued
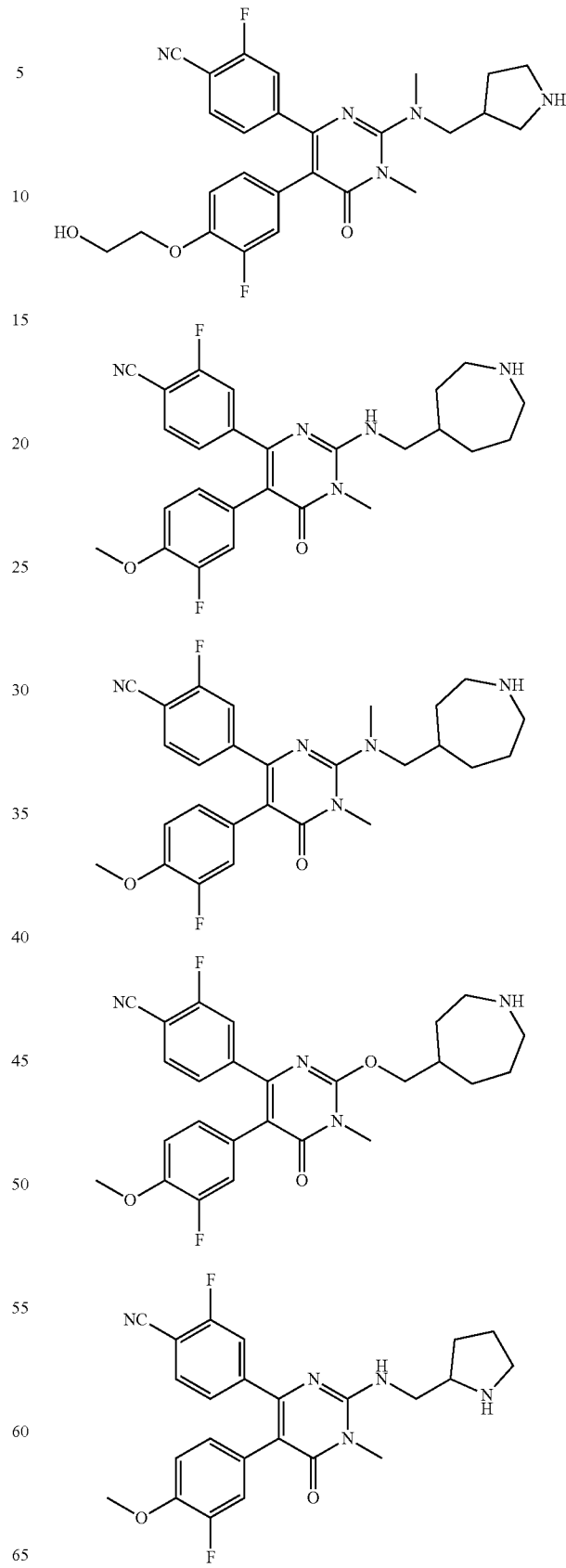

TABLE 2-continued
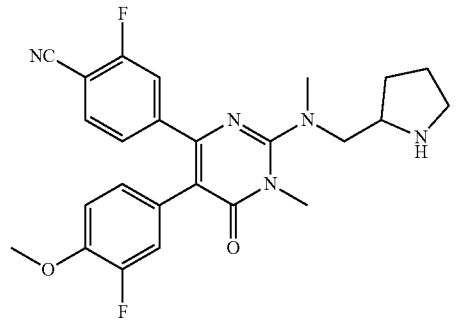 [SMILES: COc1ccc(-c2c(-c3ccc(C#N)c(F)c3)nc(N(C)CC3CCCN3)n(C)c2=O)cc1F]
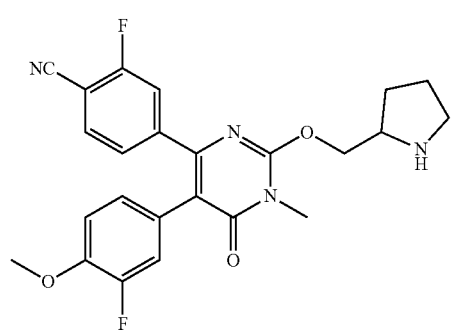 [SMILES: COc1ccc(-c2c(-c3ccc(C#N)c(F)c3)nc(OCC3CCCN3)n(C)c2=O)cc1F]
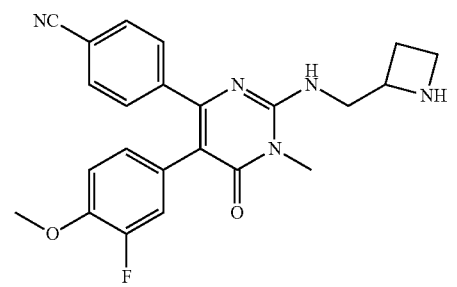 [SMILES: COc1ccc(-c2c(-c3ccc(C#N)cc3)nc(NCC3CCN3)n(C)c2=O)cc1F]
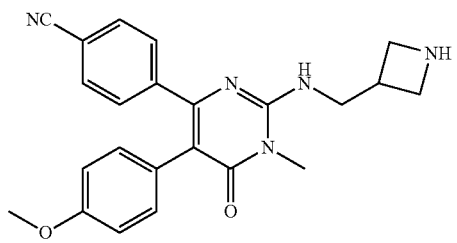 [SMILES: COc1ccc(-c2c(-c3ccc(C#N)cc3)nc(NCC3CNC3)n(C)c2=O)cc1]
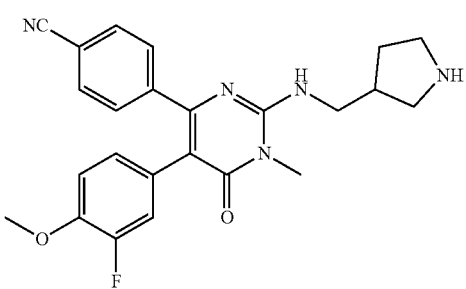 [SMILES: COc1ccc(-c2c(-c3ccc(C#N)cc3)nc(NCC3CCNC3)n(C)c2=O)cc1F]
TABLE 2-continued
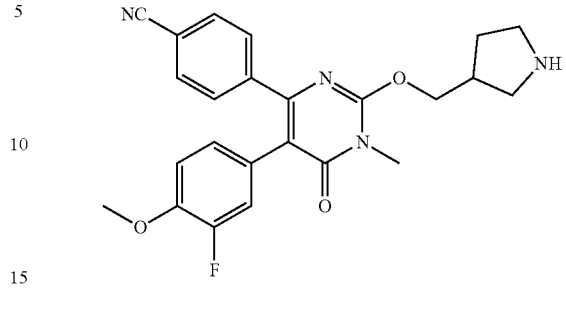
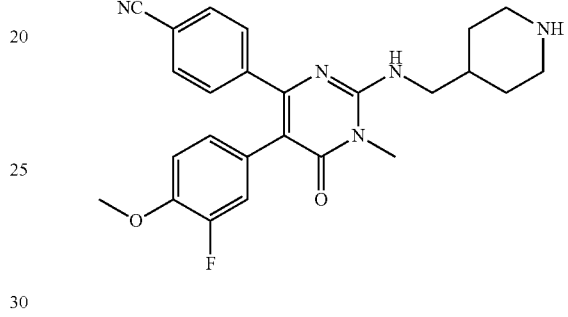
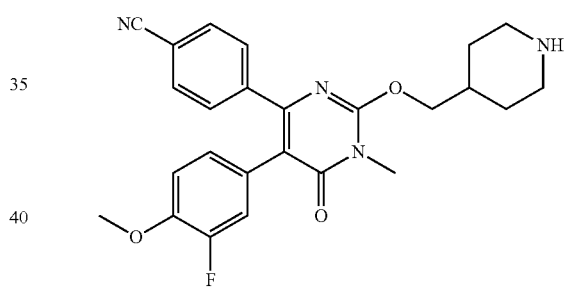
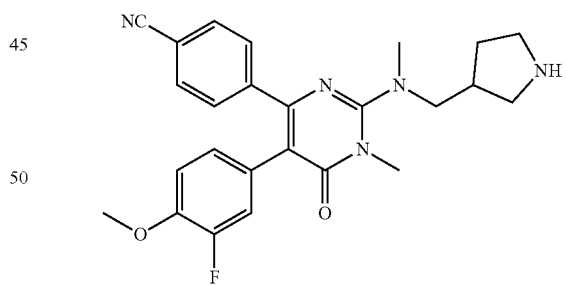 [SMILES: CN(CC1CCNC1)c1nc(-c2ccc(C#N)cc2)c(-c2ccc(OCCO)c(F)c2)c(=O)n1C]
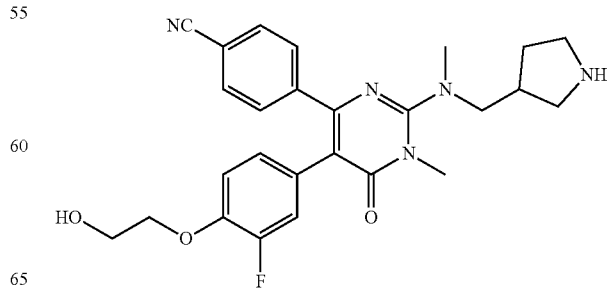

TABLE 2-continued
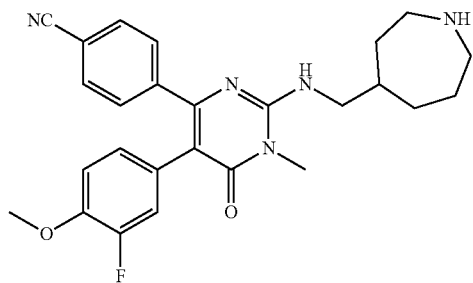
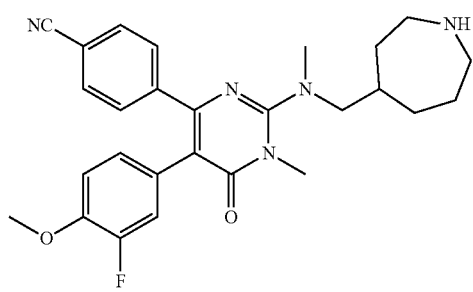 [SMILES: COc1ccc(-c2c(-c3ccc(C#N)cc3)nc(N(C)CC3CCCNCC3)n(C)c2=O)cc1F]
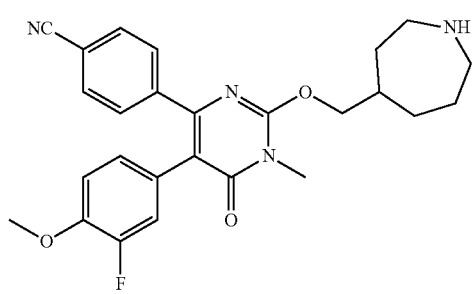
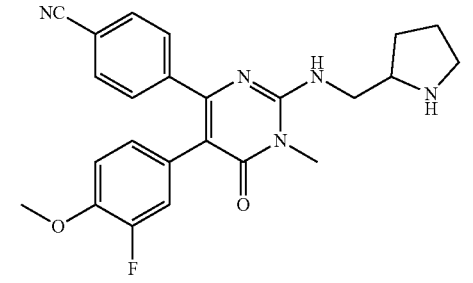 [SMILES: COc1ccc(-c2c(-c3ccc(C#N)cc3)nc(NCC3CCCN3)n(C)c2=O)cc1F]
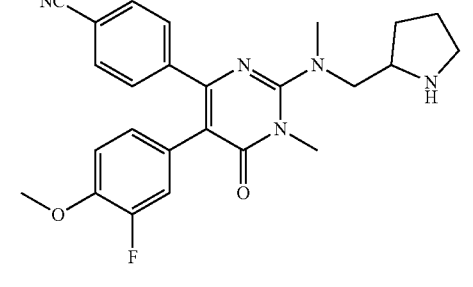
TABLE 2-continued
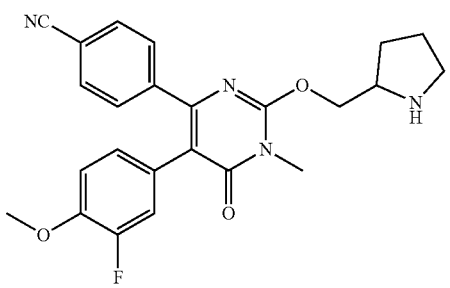 [SMILES: COc1ccc(-c2c(-c3ccc(C#N)cc3)nc(OCC3CCCN3)n(C)c2=O)cc1F]
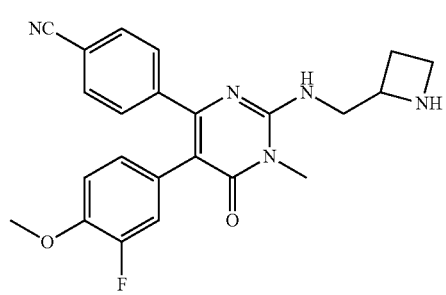 [SMILES: COc1ccc(-c2c(-c3ccc(C#N)cc3)nc(NCC3CCN3)n(C)c2=O)cc1F]
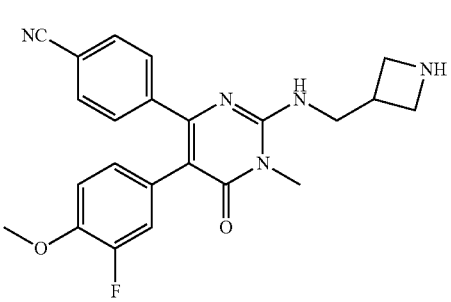 [SMILES: COc1ccc(-c2c(-c3ccc(C#N)cc3)nc(NCC3CNC3)n(C)c2=O)cc1F]
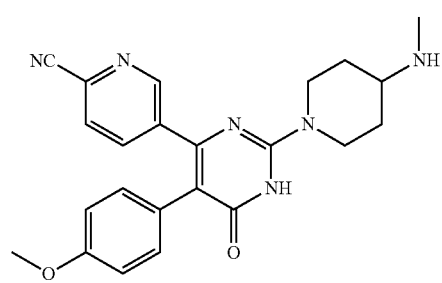
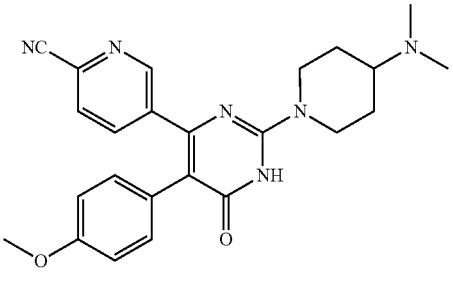

TABLE 2-continued
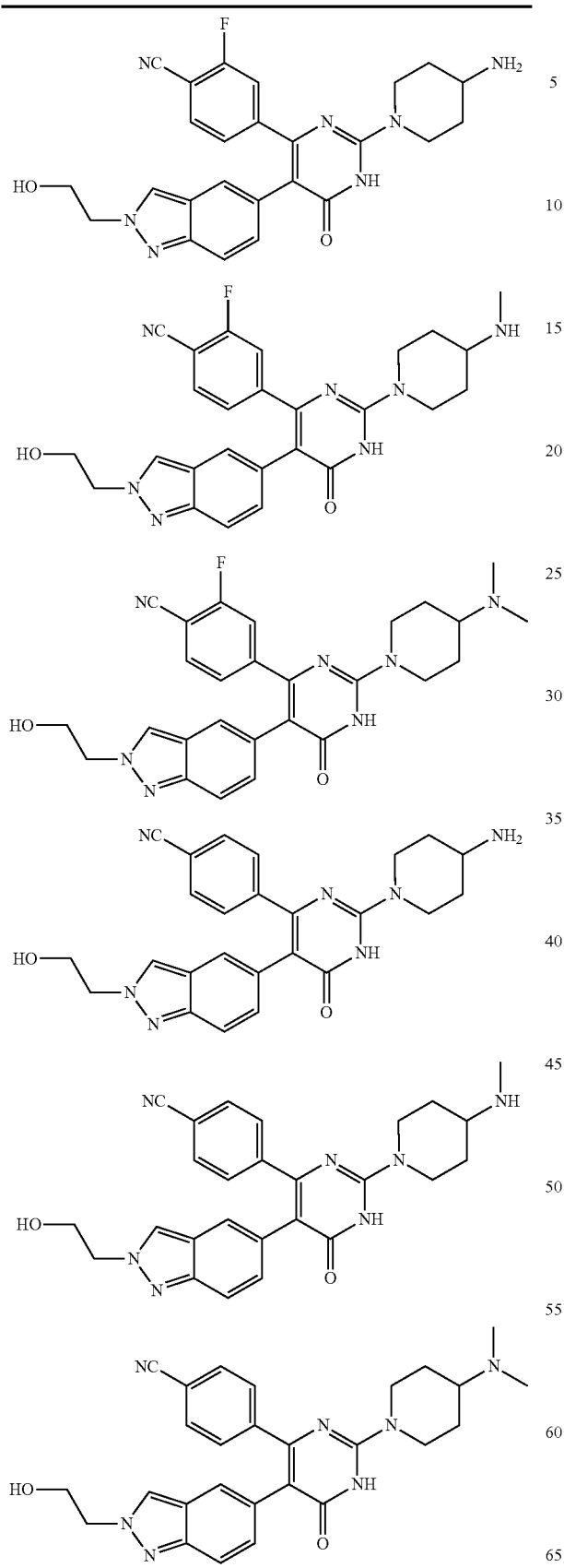
TABLE 2-continued
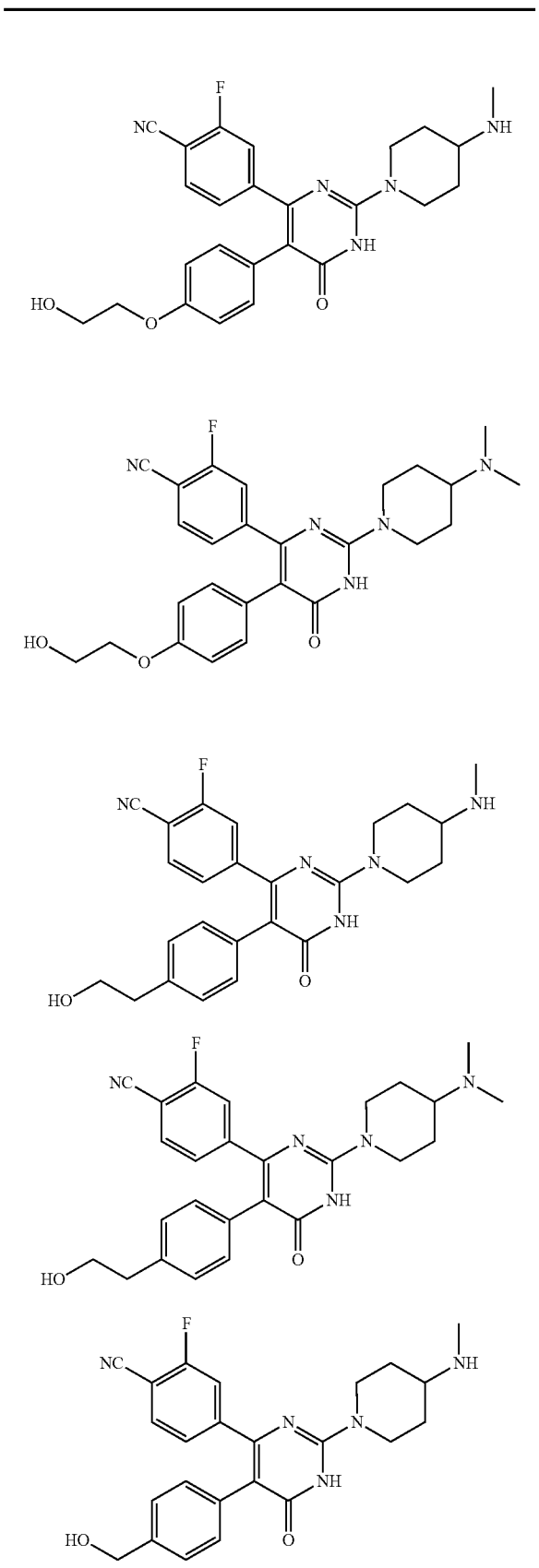

TABLE 2-continued
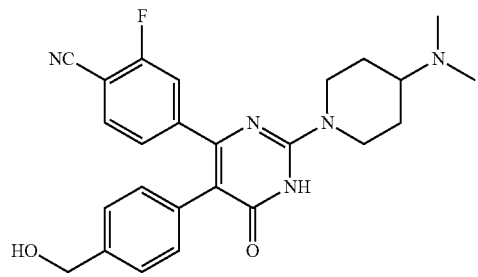 [SMILES: CN(C)C1CCN(c2nc(-c3ccc(C#N)c(F)c3)c(-c3ccc(CO)cc3)c(=O)[nH]2)CC1]
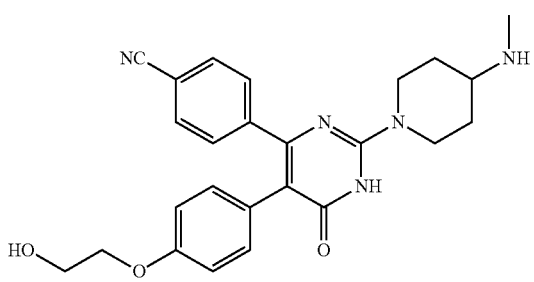 [SMILES: CNC1CCN(c2nc(-c3ccc(C#N)cc3)c(-c3ccc(OCCO)cc3)c(=O)[nH]2)CC1]
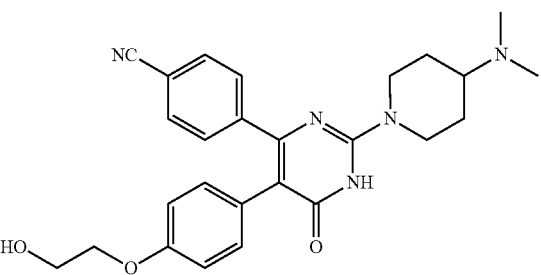 [SMILES: CN(C)C1CCN(c2nc(-c3ccc(C#N)cc3)c(-c3ccc(OCCO)cc3)c(=O)[nH]2)CC1]
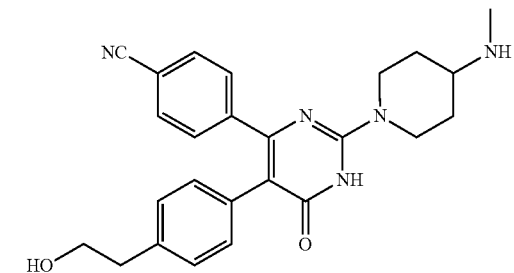 [SMILES: CNC1CCN(c2nc(-c3ccc(C#N)cc3)c(-c3ccc(CCO)cc3)c(=O)[nH]2)CC1]
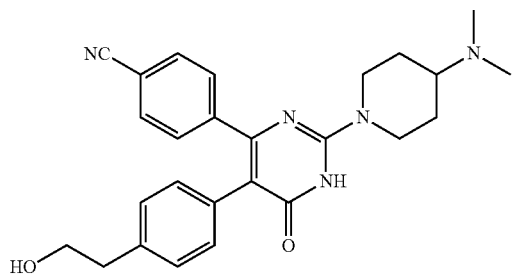 [SMILES: CN(C)C1CCN(c2nc(-c3ccc(C#N)cc3)c(-c3ccc(CCO)cc3)c(=O)[nH]2)CC1]
TABLE 2-continued
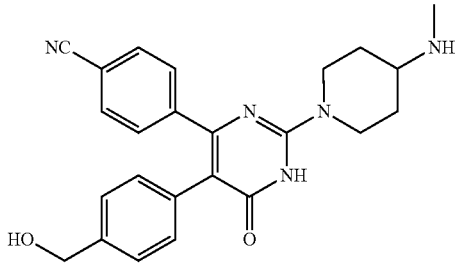 [SMILES: CNC1CCN(c2nc(-c3ccc(C#N)cc3)c(-c3ccc(CO)cc3)c(=O)[nH]2)CC1]
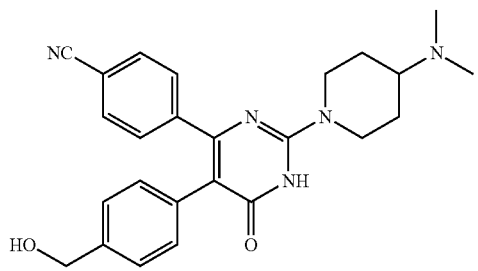 [SMILES: CN(C)C1CCN(c2nc(-c3ccc(C#N)cc3)c(-c3ccc(CO)cc3)c(=O)[nH]2)CC1]
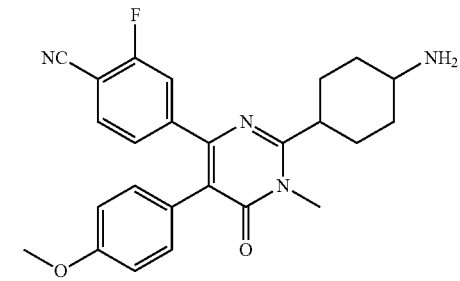 [SMILES: COc1ccc(-c2c(-c3ccc(C#N)c(F)c3)nc(C3CCC(N)CC3)n(C)c2=O)cc1]
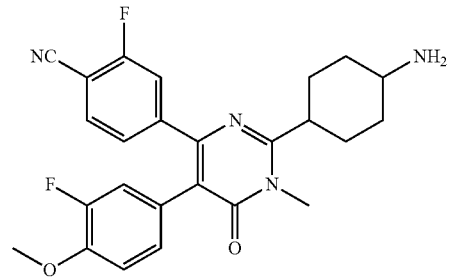 [SMILES: COc1ccc(-c2c(-c3ccc(C#N)c(F)c3)nc(C3CCC(N)CC3)n(C)c2=O)cc1F]
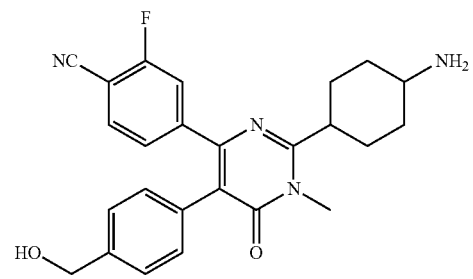 [SMILES: Cn1c(C2CCC(N)CC2)nc(-c2ccc(C#N)c(F)c2)c(-c2ccc(CO)cc2)c1=O]

TABLE 2-continued
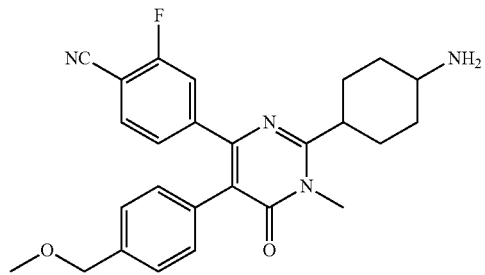 [SMILES: COCc1ccc(-c2c(-c3ccc(C#N)c(F)c3)nc(C3CCC(N)CC3)n(C)c2=O)cc1]
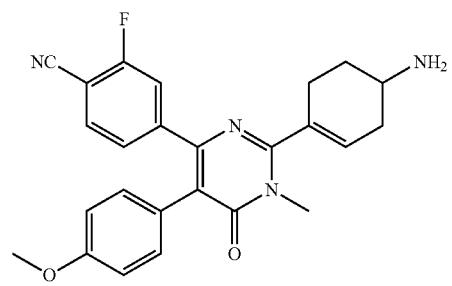 [SMILES: COc1ccc(-c2c(-c3ccc(C#N)c(F)c3)nc(C3=CCC(N)CC3)n(C)c2=O)cc1]
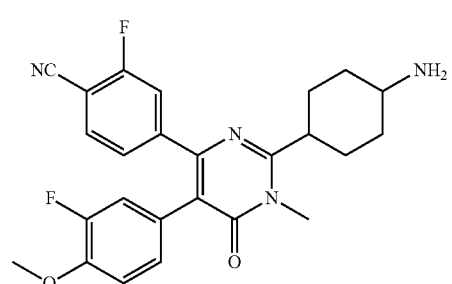
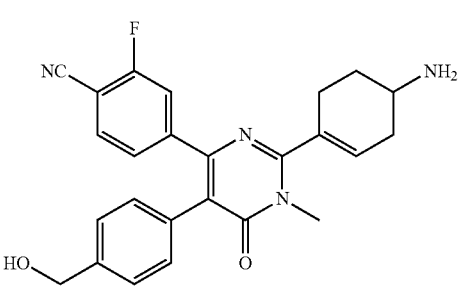 [SMILES: Cn1c(C2=CCC(N)CC2)nc(-c2ccc(C#N)c(F)c2)c(-c2ccc(CO)cc2)c1=O]
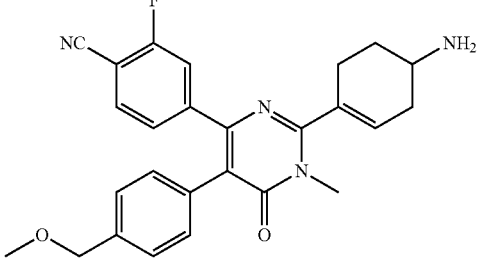
TABLE 2-continued
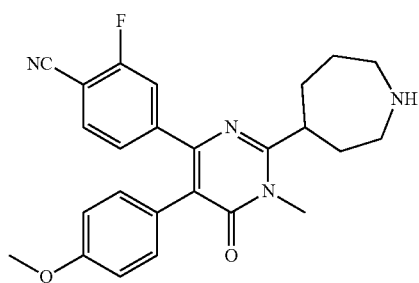 [SMILES: COc1ccc(-c2c(-c3ccc(C#N)c(F)c3)nc(C3CCCNCC3)n(C)c2=O)cc1]
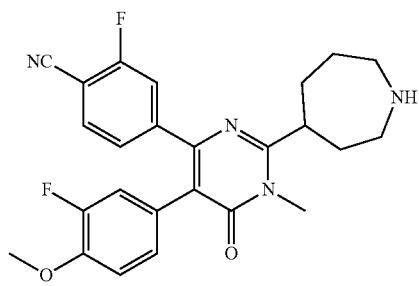 [SMILES: COc1ccc(-c2c(-c3ccc(C#N)c(F)c3)nc(C3CCCNCC3)n(C)c2=O)cc1F]
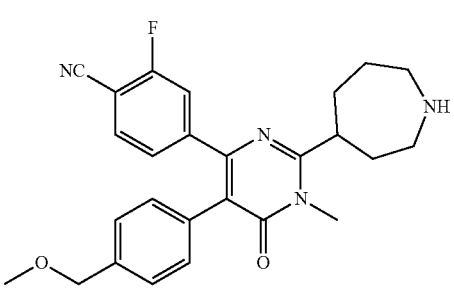 [SMILES: COCc1ccc(-c2c(-c3ccc(C#N)c(F)c3)nc(C3CCCNCC3)n(C)c2=O)cc1]
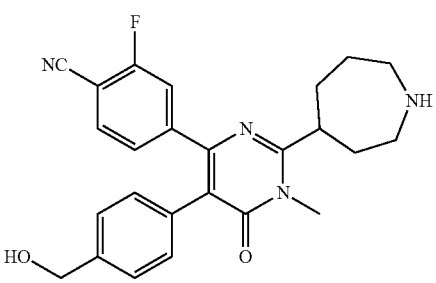 [SMILES: Cn1c(C2CCCNCC2)nc(-c2ccc(C#N)c(F)c2)c(-c2ccc(CO)cc2)c1=O]
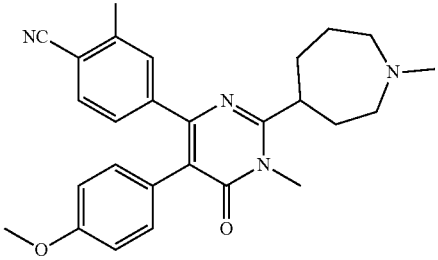

TABLE 2-continued
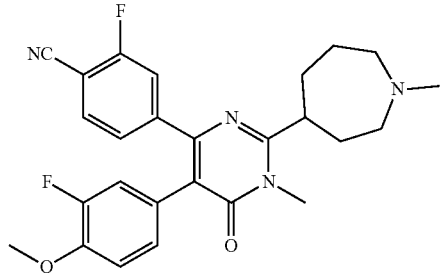
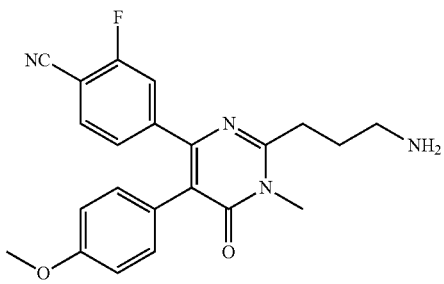 [SMILES: COc1ccc(-c2c(-c3ccc(C#N)c(F)c3)nc(CCCN)n(C)c2=O)cc1]
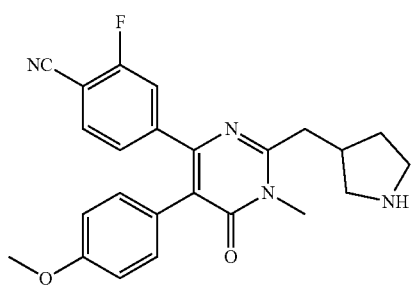 [SMILES: COc1ccc(-c2c(-c3ccc(C#N)c(F)c3)nc(CC3CCNC3)n(C)c2=O)cc1]
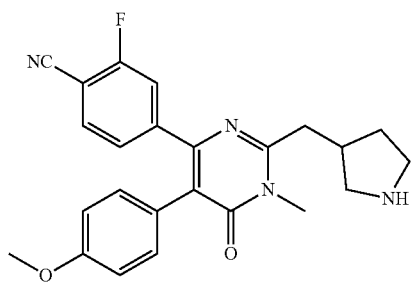 [SMILES: COc1ccc(-c2c(-c3ccc(C#N)c(F)c3)nc(CC3CCNC3)n(C)c2=O)cc1]
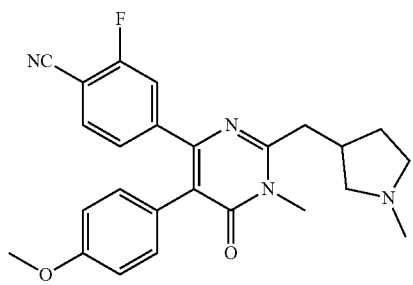 [SMILES: COc1ccc(-c2c(-c3ccc(C#N)c(F)c3)nc(CC3CCN(C)C3)n(C)c2=O)cc1]
TABLE 2-continued
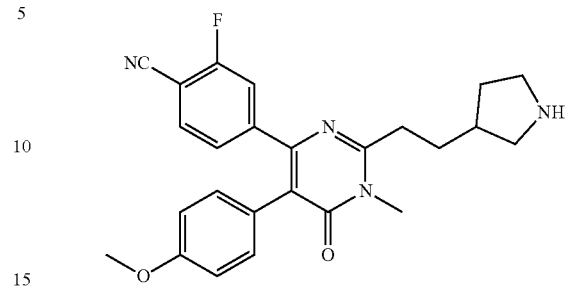
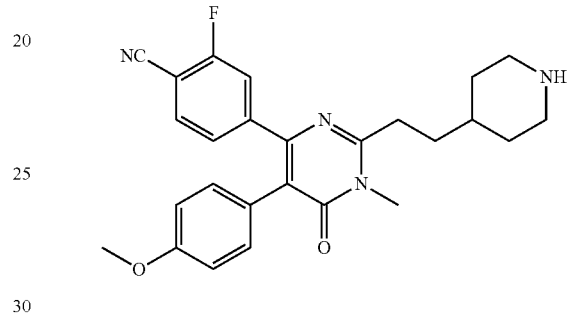
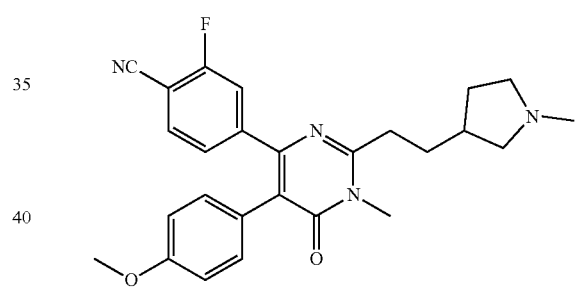
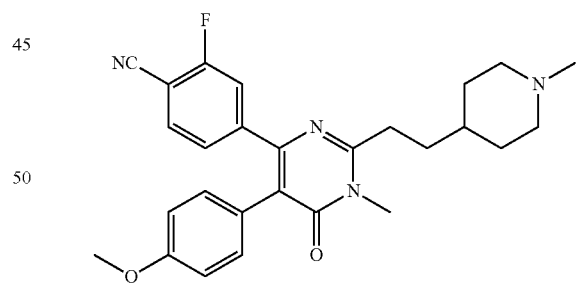
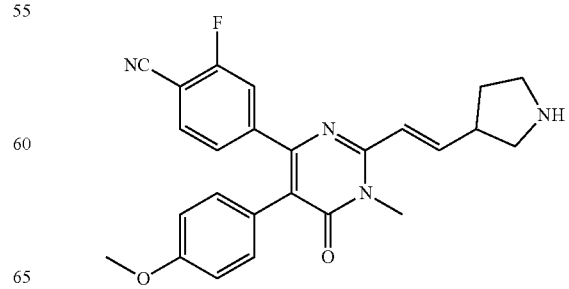

TABLE 2-continued

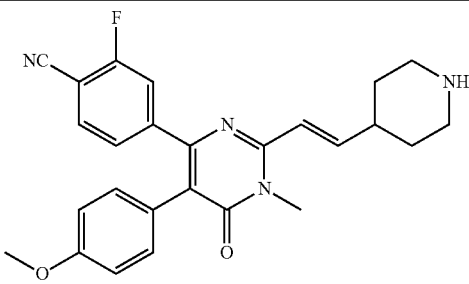

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, SYNTHETIC ORGANIC CHEMISTRY, John Wiley & Sons, Inc., New York; S. R. Sandler et al., ORGANIC FUNCTIONAL GROUP PREPARATIONS, 2nd Ed., Academic Press, New York, 1983; H. O. House, MODERN SYNTHETIC REACTIONS, 2nd Ed., W. A. Benjamin, Inc. Menlo Park, Calif. 1972; T. L. Gilchrist, HETEROCYCLIC CHEMISTRY, 2nd Ed., John Wiley & Sons, New York, 1992; J. March, ADVANCED ORGANIC CHEMISTRY: REACTIONS, MECHANISMS & STRUCTURE, 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G., ORGANIC SYNTHESIS: CONCEPTS, METHODS, STARTING MATERIALS, SECOND, REVISED & ENLARGED EDITION (1994) John Wiley & Sons ISBN: 3-527-29074-5; Hoffman, R. V., ORGANIC CHEMISTRY, AN INTERMEDIATE TEXT (1996) Oxford University Press, ISBN 0-19-509618-5; Larock, R. C. COMPREHENSIVE ORGANIC TRANSFORMATIONS: A GUIDE TO FUNCTIONAL GROUP PREPARATION, 2nd Ed. (1999) Wiley-VCH, ISBN: 0-471-19031-4; March, J. ADVANCED ORGANIC CHEMISTRY: REACTIONS, MECHANISMS, & STRUCTURE, 4th Ed. (1992) John Wiley & Sons, ISBN: 0-471-60180-2; Otera, J. (ed.), MODERN CARBONYL CHEMISTRY, (2000) Wiley-VCH, ISBN: 3-527-29871-1; Patai, S., PATAI'S 1992 GUIDE TO THE CHEMISTRY OF FUNCTIONAL GROUPS, (1992) Interscience ISBN: 0-471-93022-9; Solomons, T.W.G., ORGANIC CHEMISTRY, 7th Ed. (2000) John Wiley & Sons, ISBN: 0-471-19095-0; Stowell, J. C., INTERMEDIATE Organic Chemistry, 2nd Ed. (1993) Wiley-Interscience, ISBN: 0-471-57456-2; INDUSTRIAL ORGANIC CHEMICALS: STARTING MATERIALS & INTERMEDIATES: AN ULLMANN'S ENCYCLOPEDIA, (1999) John Wiley & Sons, ISBN: 3-527-29645-X, in 8 volumes; ORGANIC REACTIONS (1942-2000) John Wiley & Sons, in over 55 volumes; and CHEMISTRY OF FUNCTIONAL GROUPSq, John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, DC for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth, HANDBOOK OF PHARMACEUTICAL SALTS, Verlag Helvetica Chimica Acta, Zurich, 2002.

The substituted heterocyclic derivative compounds are prepared by the general synthetic route described below in Scheme 1.

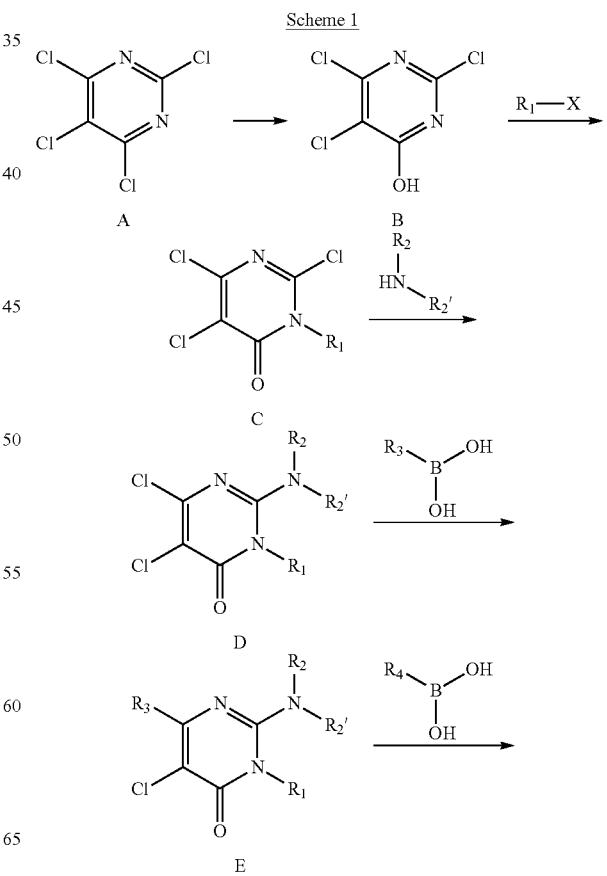

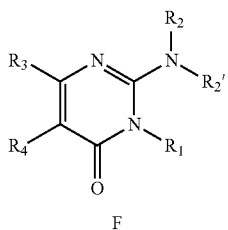

F

Referring to Scheme 1, compound A is selectively hydrolyzed to give compound B. Compound C is obtained from N-alkylation of compound B with a variety of alkyl halides $R_1$-X. Selective displacement of trichloride compound C is carried out with a variety of amines $HN(R_2)(R_2')$ under basic conditions to form compound D. Compound E is prepared from compound D under palladium-mediated cross coupling conditions with boronic acids, e.g. $R_3$—$B(OH)_2$, or boronic esters. Compound F is prepared from compound E under palladium-mediated cross coupling conditions with boronic acids, e.g., $R_3$—$B(OH)_2$, or boronic esters.

Pharmaceutical Compositions of the Substituted Heterocyclic Derivative Compounds In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: THE SCIENCE & PRACTICE OF PHARMACY (Gennaro, 21$^{st}$ Ed. Mack Pub. Co., Easton, PA (2005)).

Provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (Ia), or a pharmaceutically acceptable salt thereof, and a pharmaceutically acceptable excipient. One embodiment provides a pharmaceutical composition comprising a compound of Formula (Ib), or a pharmaceutically acceptable salt thereof, and a pharmaceutically acceptable excipient.

In certain embodiments, the substituted heterocyclic derivative compound as described by Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., REMINGTON: THE SCIENCE & PRACTICE OF PHARMACY (Gennaro, 21$^{st}$ Ed. Mack Pub. Co., Easton, PA (2005)).

The dose of the composition comprising at least one substituted heterocyclic derivative compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Use of the Substituted Heterocyclic Derivative Compounds

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications are acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

LSD-1

Lysine-specific demethylase 1 (LSD1) is a histone lysine demethylase that specifically demethylates monomethylated and dimethylated histone H3 at K4 and also demethylates dimethylated histone H3 at K9. Although the main target of LSD1 appears to be mono- and di-methylated histone lysines, specifically H3K4 and H3K9, there is evidence in the literature that LSD1 can demethylate methylated lysines on non-histone proteins like p53, E2F1, Dnmtl and STAT3.

LSD1 has a fair degree of structural similarity and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.

In some embodiments, the compounds disclosed herein are capable of inhibiting LSD1 activity in a biological sample by contacting the biological sample with a substituted heterocyclic compound as disclosed herein. In some embodiments, a substituted heterocyclic compound as disclosed herein is capable of modulating the level of histone-4 lysine-3 methylation in the biological sample. In some embodiments, a substituted heterocyclic compound as disclosed herein is capable of modulating histone-3 lysine-9 methylation levels in the biological sample.

The substituted heterocyclic compounds disclosed herein lack significant MAO-A or MAO-B inhibitory activity. In some embodiments, a substituted heterocyclic compound as disclosed herein inhibits LSD1 inhibitory activity to a greater extent than MAO-A and/or MAO-B inhibitory activity.

One embodiment provides a method of regulating gene transcription in a cell comprising inhibiting lysine-specific demethylase 1 activity by exposing the lysine-specific demethylase 1 enzyme to a compound of Formula (I). One embodiment provides a method of regulating gene transcription in a cell comprising inhibiting lysine-specific demethylase 1 activity by exposing the lysine-specific demethylase 1 enzyme to a compound of Formula (Ia). One embodiment provides a method of regulating gene transcription in a cell comprising inhibiting lysine-specific demethylase 1 activity by exposing the lysine-specific demethylase 1 enzyme to a compound of Formula (Ib).

Methods of Treatment

Disclosed herein are methods of modulating demethylation in a cell or in a subject, either generally or with respect to one or more specific target genes. Demethylation is modulated to control a variety of cellular functions, including without limitation: differentiation; proliferation; apoptosis; tumorigenesis, leukemogenesis or other oncogenic transformation events; hair loss; or sexual differentiation.

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (Ia), or a pharmaceutically acceptable salt thereof. One embodiment provides a method of treating cancer in a patient in need thereof, comprising administering to the patient a compound of Formula (Ib), or a pharmaceutically acceptable salt thereof.

In a further embodiment is the method for treating cancer in a subject wherein the cancer is selected from prostate cancer, breast cancer, bladder cancer, lung cancer or melanoma. In a further embodiment is the method for treating cancer in a subject wherein the cancer is selected from acute myeloid leukemia (AML), acute lymphoblastic leukemia (ALL), small cell lung cancer (SCLC), non-small cell lung cancer (NSCLC), neuroblastoma, small round blue cell tumors, or glioblastoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (S) and coupling constants, J are reported in Hertz. For proton spectra the solvent peak was used as the reference peak.

Preparation 1A: 2,5,6-trichloropyrimidin-4-ol

To a solution of 2,4,5,6-tetrachloropyrimidine (5 g, 22.9 mmol) in THF (50 mL) was added 1N NaOH (31 mL, 31.2 mmol) dropwise, and the mixture was stirred overnight at RT. The solution was acidified with 1N HCl and extracted with DCM (3×). The organics were combined, dried, and concentrated in vacuo. The solids were slurried in $Et_2O$ for 30 min at RT, filtered, washed with $Et_2O$, and dried to give 3.0 g (66%) of the title compound. [M+H] Calc'd for $C_4HCl_3N_2O$, 201. Found, 201.

Preparation 1B: 2,5,6-trichloro-3-methyl-3-hydropyrimidin-4-one

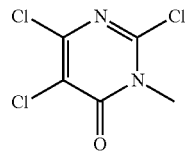

To a mixture of 2,5,6-trichloropyrimidin-4-ol (1 g, 5.0 mmol) and $K_2CO_3$ (759 mg, 5.5 mmol) in THF (50 mL) at 0° C. was added iodomethane (714 mg, 5.0 mmol) dropwise, and the reaction was stirred at RT overnight. The reaction mixture was diluted with ethyl acetate (EA). The organic phase was washed with brine, dried and concentrated in vacuo. The residue was purified by silica gel chromatography (10:1, PE:EA) to give 760 mg (71%) of the title compound. $^1$H NMR (400 MHz, $CDCl_3$): δ 3.74 (s, 3H). [M+H] Calc'd for $C_5H_3Cl_3N_2O$, 213. Found, 213.

Preparation 1C: N-[1-(5,6-dichloro-3-methyl-4-oxo (3-hydropyrimidin-2-yl)) (4-piperidyl)](tert-butoxy) carboxamide

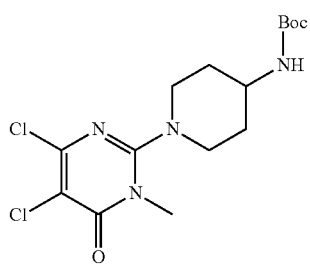 [SMILES: Cn1c(N2CCC(NC(=O)OC(C)(C)C)CC2)nc(Cl)c(Cl)c1=O]

A solution of 2,5,6-trichloro-3-methyl-3-hydropyrimidin-4-one (426 mg, 2.0 mmol), DIEA (536 mg, 4.0 mmol) and tert-butyl piperidin-4-ylcarbamate (400 mg, 2 mmol) in DMF (10 mL) was heated at 120° C. for 1 h. The solvent was removed hi vacuo and the residue was purified by silica gel chromatography (1:1, PE:EA) to give 550 mg (73%) of the title compound. $^1$H NMR (400 MHz, $CDCl_3$): δ 1.45 (s, 9H), 1.50-1.58 (m, 2H), 2.06-2.10 (m, 2H), 2.98-3.05 (m, 2H), 3.48 (s, 3H), 3.53-3.56 (m, 2H), 3.70 (s, 1H), 4.52 (s, 1H). [M+H] Calc'd for $C_{15}H_{22}Cl_2N_4O_3$, 213; Found, 213.

Preparation 1D: tert-butyl 1-(5-chloro-4-(4-cyanophenyl)-1-methyl-6-oxo-1,6-dihydropyrimidin-2-yl) piperidin-4-ylcarbamate

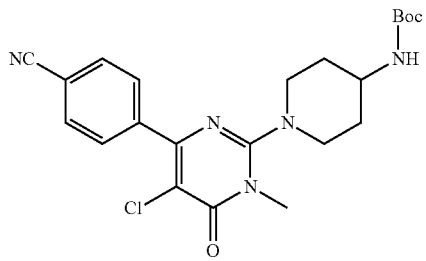 [SMILES: Cn1c(N2CCC(NC(=O)OC(C)(C)C)CC2)nc(-c2ccc(C#N)cc2)c(Cl)c1=O]

A mixture of N-[1-(5,6-dichloro-3-methyl-4-oxo(3-hydropyrimidin-2-yl))(4-piperidyl)](tert-butoxy)carboxamide (500 mg, 1.3 mmol), 4-cyanophenylboronic acid (195 ng, 1 3 mmol), [1,1'-bis(di-tert-butylphosphino)ferrocene]dichloropalladium(II) (81 mg, 0.13 mmol) and $K_2CO_3$ (359 mg, 2.6 mmol) in DMF (10 mL) was flushed with nitrogen and stirred at 85° C. for 2 h. Water was added, and the mixture was extracted with EA (3×). The organics were combined, washed with water, washed with brine, dried and concentrated in vacuo. The residue was purified purified by silica chromatography (1:1, EA:PE) to give 250 mg (40%) of the title compound. $^1$H NMR (400 MHz, $CDCl_3$): δ 1.45 (s, 9H), 1.54-1.61 (m, 2H), 2.05-2.10 (m, 2H), 2.99-3.05 (m, 2H), 3.48-3.56 (s, 5H), 3.70 (s, 1H), 4.56 (s, 1H), 7.73 (d, J=8.0 Hz, 2H), 7.93 (d, J=8.0 Hz, 2H). [M+H] Calc'd for $C_{22}H_{26}ClN_5O_3$, 444. Found, 444.

Preparation 1E: tert-butyl 1-(4-(4-cyanophenyl)-1-methyl-6-oxo-5-p-tolyl-1,6-dihydropyrimidin-2-yl) piperidin-4-ylcarbamate

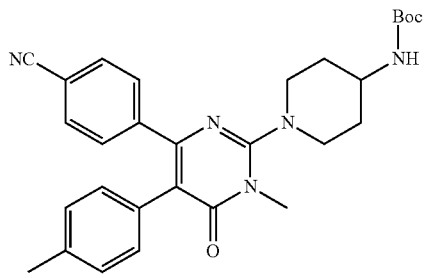 [SMILES: Cc1ccc(-c2c(-c3ccc(C#N)cc3)nc(N3CCC(NC(=O)OC(C)(C)C)CC3)n(C)c2=O)cc1]

A mixture of tert-butyl 1-(5-chloro-4-(4-cyanophenyl)-1-methyl-6-oxo-1,6-dihydropyrimidin-2-yl)piperidin-4-ylcarbamate (200 mg, 0.45 mmol), p-tolylboronic acid (123 mg, 0.90 mmol), [1,1'-bis(di-tert-butylphosphino)ferrocene]dichioropalladium(II) (28 mg, 0.045 mol) and K₂CO₃ (124 mg, 0.90 mmol) in DMF (10 mL) was flushed with nitrogen and stirred at 85° C. for 2 h. Water was added, and the mixture was extracted with EA (3×). The organics were combined, washed with water, washed with brine, dried and concentrated in vacuo. The residue was purified by silica chromatography (1:1, EA:PE) to give 50 mg (22%) of the title compound. [M+H] Calc'd for $C_{29}H_{33}N_5O_3$, 500. Found, 500.

Example 1: 4-(2-(4-aminopiperidin-1-yl)-1-methyl-6-oxo-5-p-tolyl-1,6-dihydropyrimidin-4-yl)benzonitrile, HCl Salt

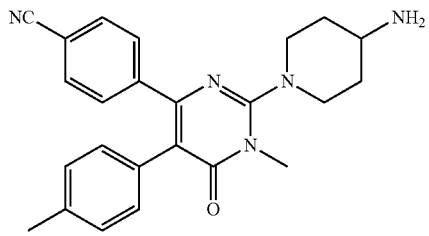

To a solution of tert-butyl 1-(4-(4-cyanophenyl)-1-methyl-6-oxo-5-p-tolyl-1,6-dihydro pyrimidin-2-yl)piperidin-4-ylcarbamate (50 mg, 0.1 mmol) in EA (10 mL) was added a 4N HCl solution in EA (5 mL) and the mixture was stirred at RT for 2 h. The solvent was concentrated in vacuo, and the residue was purified by preparative HPLC to give 20 mg (46%) of the title compound as the hydrochloride salt. ¹H NMR (400 MHz, CDCl₃): δ 1.74-1.79 (m, 2H), 2.00-2.04 (m, 2H), 2.21 (s, 3H), 2.96-3.03 (m, 2H), 3.29-3.03 (m, 1H), 3.48 (s, 3H), 3.71-3.74 (m, 2H), 6.89 (d, J=8.0 Hz, 2H), 6.99 (d, J=8.0 Hz, 2H), 7.38 (d, J=8.0 Hz, 2H), 7.44 (d, J=8.4 Hz, 2H). [M+H] Calc'd for $C_{24}H_{25}N_5O$, 400. Found, 400.

Example 2: 4-[2-(4-amino-piperidin-1-yl)-5-(4-methoxy-phenyl)-1-methyl-6-oxo-1,6-dihydro-pyrimidin-4-yl]-benzonitrile

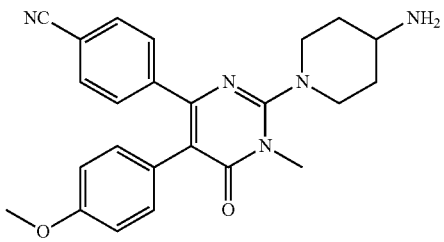 [SMILES: COc1ccc(-c2c(-c3ccc(C#N)cc3)nc(N3CCC(N)CC3)n(C)c2=O)cc1]

The title compound was prepared as the hydrochloride salt in 5% overall yield according to the general procedure for the preparation of Example 1. ¹H NMR (400 MHz, CD₃OD): δ 1.74-1.78 (m, 2H), 2.00-2.03 (m, 2H), 2.98-3.02 (m, 2H), 3.26-3.00 (m, 1H), 3.48 (s, 3H), 3.69 (s, 3H), 3.70-3.73 (m, 2H), 6.72 (d, J=8.8 Hz, 2H), 6.93 (d, J=8.4 Hz, 2H), 7.39 (d, J=8.0 Hz, 2H), 7.46 (d, J=8.0 Hz, 2H). [M+H] Calc'd for $C_{24}H_{25}N_5O_2$, 416. Found, 416.

Example 3: 4-[2-(4-amino-piperidin-1-yl)-5-(6-methoxy-pyridin-3-yl)-1-methyl-6-oxo-1,6-dihydro-pyrimidin-4-yl]-benzonitrile

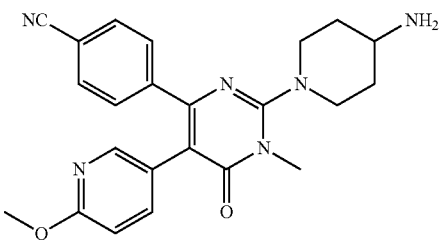 [SMILES: COc1ccc(-c2c(-c3ccc(C#N)cc3)nc(N3CCC(N)CC3)n(C)c2=O)cn1]

The title compound was prepared as the hydrochloride salt in 11% overall yield according to the general procedure for the preparation of Example 1. ¹H NMR (400 MHz, CD₃OD): δ 1.87-1.95 (m, 2H), 2.14-2.17 (m, 2H), 3.15-3.24 (m, 2H), 3.43-3.48 (m, 1H), 3.62 (s, 3H), 3.93-3.98 (m, 2H), 4.23 (s, 3H), 7.46 (d, J=9.2 Hz, 1H), 7.63 (d, J=8.0 Hz, 2H), 7.71 (d, J=8.4 Hz, 2H), 8.12 (dd, J=8.8, 1.6 Hz, 1H), 8.28 (d, J=2.0 Hz, 1H). [M+H] Calc'd for $C_{23}H_{24}N_6O_2$, 417; Found, 417.

Example 4: 4-[2-(4-amino-piperidin-1-yl)-1-methyl-5-(6-methyl-pyridin-3-yl)-6-oxo-1,6-dihydro-pyrimidin-4-yl]-benzonitrile

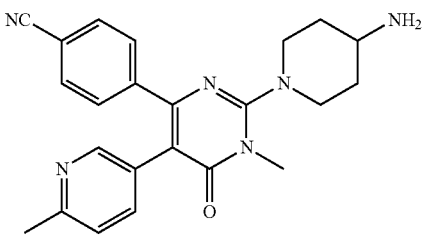

The title compound was prepared as the hydrochloride salt in 4% overall yield according to the general procedure for the preparation of Example 1. ¹H NMR (400 MHz, CD₃OD): δ 1.79-1.80 (m, 2H), 2.03-2.05 (m, 2H), 2.66 (s, 3H), 3.04-3.09 (m, 2H), 3.30-3.34 (m, 1H), 3.50 (s, 3H), 3.83-3.88 (m, 2H), 7.48 (d, J=8.4 Hz, 2H), 7.58 (d, J=8.4 Hz, 2H), 7.64 (d, J=8.4 Hz, 1H), 8.00 (dd, J=8.4, 2.0 Hz, 1H), 8.54 (d, J=8.0 Hz, 1H). [M+H] Calc'd for $C_{23}H_{24}N_6O$, 401; Found, 401.

Example 5: 4-[2-(4-amino-piperidin-1-yl)-5-(4-methoxy-phenyl)-1-methyl-6-oxo-1,6-dihydro-pyrimidin-4-yl]-benzonitrile

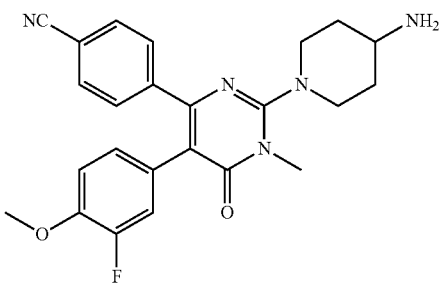 [SMILES: COc1ccc(-c2c(-c3ccc(C#N)cc3)nc(N3CCC(N)CC3)n(C)c2=O)cc1F]

The title compound was prepared as the hydrochloride salt in 7% overall yield according to the general procedure for the preparation of Example 1. $^1$H NMR (400 MHz, CD$_3$OD): δ 1.89-1.95 (m, 2H), 2.15-2.18 (m, 2H), 3.14-3.18 (m, 2H), 3.44-3.46 (m, 11H), 3.60 (s, 3H), 3.88-3.90 (m, 5H), 6.79 (d, J=8.4 Hz, 1H), 6.96-7.02 (m, 2H), 7.54 (d, J=8.0 Hz, 2H), 7.64 (d, J=8.0 Hz, 2H). [M+H] Calc'd for C$_{24}$H$_{24}$FN$_5$O$_2$, 434. Found, 434.

Example 6: 4-[2-(4-amino-piperidin-1-yl)-5-(4-methoxy-phenyl)-1-methyl-6-oxo-1,6-dihydro-pyrimidin-4-yl]-2-fluoro-benzonitrile

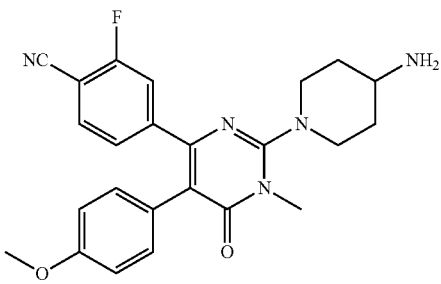 [SMILES: COc1ccc(-c2c(-c3ccc(C#N)c(F)c3)nc(N3CCC(N)CC3)n(C)c2=O)cc1]

The title compound was prepared as the hydrochloride salt in 5% overall yield according to the general procedure for the preparation of Example 1. $^1$H NMR (400 MHz, CD$_3$OD): δ 1.83-1.89 (m, 2H), 2.10-2.13 (m, 2H), 3.05-3.11 (m, 2H), 3.35-3.38 (m, 1H), 3.55 (s, 3H), 3.76 (s, 3H), 3.77-3.82 (m, 2H), 6.84 (d, J=8.8 Hz, 2H), 7.04 (d, J=8.8 Hz, 2H), 7.21 (d, J=8.0 Hz, 1H), 7.35 (d, J=8.0 Hz, 1H), 7.53-7.56 (m, 1H). [M+H] Calc'd for C$_{24}$H$_{24}$FN$_5$O$_2$, 434. Found, 434.

Preparation 7A: tert-butyl 1-(5-chloro-4-(3-fluoro-4-cyanophenyl)-1-methyl-6-oxo-1,6-dihydropyrimidin-2-yl)piperidin-4-yl carbamate

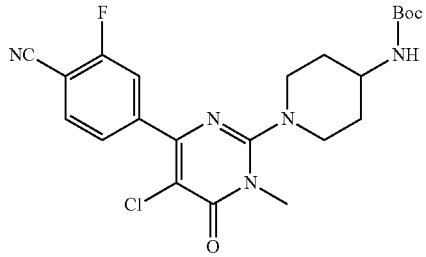 [SMILES: Cn1c(N2CCC(NC(=O)OC(C)(C)C)CC2)nc(-c2ccc(C#N)c(F)c2)c(Cl)c1=O]

A mixture of N-[1-(5,6-dichloro-3-methyl-4-oxo(3-hydropyrimidin-2-yl))(4-piperidyl)](tert-butoxy)carboxamide (150 g, 0.40 mol), 3-fluoro-4-cyanophenylboronic acid (65.8 g, 0.40 mol), Pd(Ph$_3$P)$_4$ (9.3 g, 8 mmol) and 0.4 N Na$_2$CO$_3$ (2 L, 0.80 mol) in ACN (4 L) was flushed with nitrogen and stirred at 85° C. for 2 h. Water was added and the mixture was extracted with EA (3×). The organics were combined, washed with water, washed with brine, dried and concentrated in vacuo. The residue was purified by silica chromatography (1:1, EA:PE) to give 95 g (57%) of the title compound. $^1$H NMR (400 MHz, CDCl$_3$): δ 1.45 (s, 9H), 1.54-1.61 (m, 2H), 2.05-2.13 (m, 2H), 2.99-3.08 (m, 2H), 3.53-3.58 (s, 5H), 3.70 (s, 1H), 4.54 (d, J=6.0 Hz, 1H), 7.68-7.80 (m, 3H).

Preparation 7B: tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate

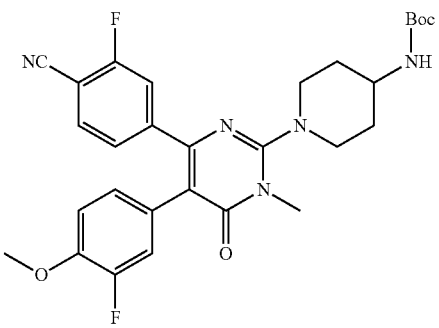 [SMILES: COc1ccc(-c2c(-c3ccc(C#N)c(F)c3)nc(N3CCC(NC(=O)OC(C)(C)C)CC3)n(C)c2=O)cc1F]

A mixture of (tert-butoxy)-N-{1-[5-chloro-6-(4-cyano-3-fluorophenyl)-3-methyl-4-oxo(3-hydropyrimidin-2-yl)](4-piperidyl)}carboxamide (1 g, 2.169 mmol), 3-fluoro-4-methoxy benzeneboronic acid (740 mg, 4.338 mmol), Pd(dppf)Cl$_2$ (480 mg, 0.651 mmol) and Na$_2$CO$_3$ (690 mg, 6.51 mmol) in dioxane:H$_2$O (3:1, 15 mL) was flushed with nitrogen, capped and stirred at 145° C. for 2 h in the microwave. The reaction mixture was concentrated and the residue was purified by FC (1:1, EA:PE) to give 800 mg (71%) of the title compound. [M+H] Calc'd for C$_{29}$H$_{31}$F$_2$N$_5$O$_4$, 552. Found, 552. $^1$H NMR (400 MHz, CDCl$_3$): δ ppm 1.46 (s, 9H), 1.60 (d, J=10.11 Hz, 2H), 2.11 (d, J=11.62 Hz, 2H), 3.06 (t, J=12.00 Hz, 2H), 3.54 (s, 3H), 3.60 (d, J=13.64 Hz, 2H), 3.72 (br. s., 1H), 3.88 (s, 3H), 4.52

(br. s., 1H), 6.79-6.89 (m, 2H), 6.97 (d, J=12.38 Hz, 1H), 7.13 (d, J=8.34 Hz, 1 H), 7.31 (d, J=9.85 Hz, 1H), 7.42 (br. s., 1H).

Example 7: 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile

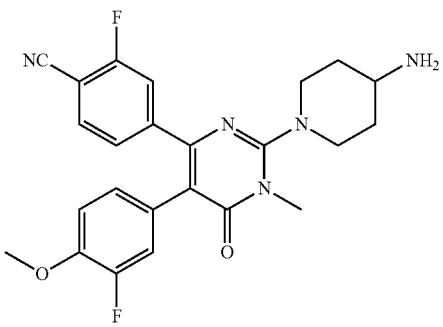 [SMILES: COc1ccc(-c2c(-c3ccc(C#N)c(F)c3)nc(N3CCC(N)CC3)n(C)c2=O)cc1F]

To a solution of tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate (5.2 g, 9.44 mmol) in EA (20 mL) was added a 1N HCl in EA (30 mL). The mixture was stirred at RT for 2 h. The solvent was concentrated in vacuo to give the title product as the HCl salt (4.05 g, 88%). $^1$H NMR (400 MHz, CD$_3$OD): δ 1.77-1.79 (m, 2H), 2.02-2.04 (m, 2H), 2.99-3.04 (m, 2H), 3.26-3.00 (m, 1H), 3.38 (s, 3H), 3.73 (s, 3H), 3.73-3.75 (m, 2H), 6.67-6.68 (m, 1H), 6.84-6.95 (m, 2H), 7.12-7.14 (m, 1H), 7.24-7.36 (m, 1H), 7.46-7.50 (m, 1H). [M+H] Calc'd for C$_{24}$H$_{23}$F$_2$N$_5$O$_2$, 452. Found, 452.

Example 8: 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile

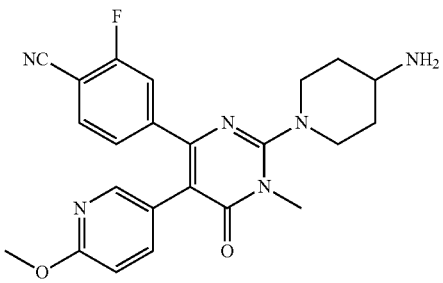

The title compound was prepared as the hydrochloride salt in 6% overall yield according to the general procedure for the preparation of Example 1. $^1$H NMR (400 MHz, CD$_3$OD): δ 1.79-1.83 (m, 2H), 2.02-2.06 (m, 2H), 3.04-3.11 (m, 2H), 3.21-3.22 (m, 1H), 3.49 (s, 3H), 3.81-3.85 (m, 2H), 4.12 (s, 3H), 7.22-7.24 (m, 1H), 7.38 (d, J=9.2 Hz, 1H), 7.49 (d, J=9.2 Hz, 1H), 7.57-7.61 (m, 1H), 8.04-8.07 (m, 1H), 8.21 (s, 1H). [M+H] Calc'd for C$_{23}$H$_{23}$FN$_6$O$_2$, 435; Found, 435.

Example 9: 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile

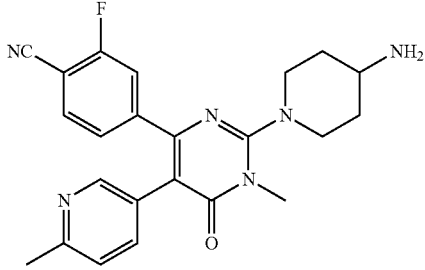

The title compound was prepared as the hydrochloride salt in 8% overall yield according to the general procedure for the preparation of Example 1. $^1$H NMR (400 MHz, CD$_3$OD): δ 1.92-1.96 (m, 2H), 2.16-2.19 (m, 2H), 2.80 (s, 3H), 3.19-3.25 (m, 2H), 3.45-3.49 (m, 1H), 3.62 (s, 3H), 3.96-3.99 (m, 2H), 7.34 (d, 1=8.0 Hz, 1H), 7.60 (d, 1=7.2 Hz, 1H), 7.71 (t, 1=7.6 Hz, 1H), 7.80 (d, J=8.4 Hz, 1H), 8.18 (d, J=8.4 Hz, 1H), 8.71 (s, 1H). [M+H] Calc'd for C$_{23}$H$_{23}$FN$_6$O, 419, Found, 419.

Example 10: 4-[2-(4-amino-piperidin-1-yl)-5-(6-ethyl-pyridin-3-yl)-1-methyl-6-oxo-1,6-dihydro-pyrimidin-4-yl]-benzonitrile

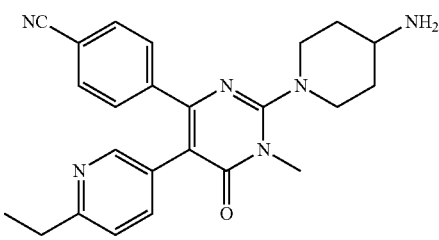 [SMILES: CCc1ccc(-c2c(-c3ccc(C#N)cc3)nc(N3CCC(N)CC3)n(C)c2=O)cn1]

The title compound was prepared as the hydrochloride salt in 7% overall yield according to the general procedure for the preparation of Example 1. $^1$H NMR (400 MHz, CD$_3$OD): δ 1.30 (t, J=4.0 Hz, 3H), 1.83-1.88 (m, 2H), 2.06-2.09 (m, 2H), 2.96-2.99 (m, 2H), 3.09-3.16 (m, 2H), 3.26-3.31 (m, 1H), 3.51 (s, 3H), 3.86-3.89 (m, 2H), 7.35 (d, J=8.0 Hz, 2H), 7.61 (d, J=8.0 Hz, 2H), 7.71 (d, J=8.4 Hz, 1H), 8.08 (d, 1=8.4 Hz, 1H), 8.57 (s, 1H). [M+H] Calc'd for C$_{24}$H$_{26}$N$_6$O, 415. Found, 415.

Example 11: 2-fluoro-4-[5-(4-methoxy-phenyl)-1-methyl-2-(4-methylamino-piperidin-1-yl)-6-oxo-1,6-dihydro-pyrimidin-4-yl]-benzonitrile

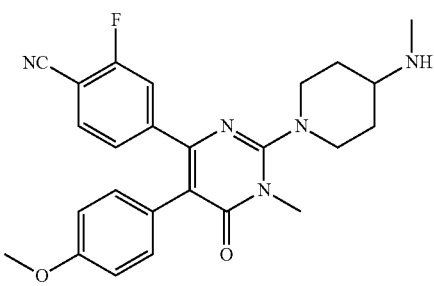

The title compound was prepared as the hydrochloride salt in 7% overall yield according to the general procedure for the preparation of Example 1. $^1$H NMR (400 MHz, CD$_3$OD): δ 1.80-1.90 (m, 2H), 2.19-2.23 (m, 2H), 2.75 (s, 3H), 3.06-3.12 (m, 2H), 3.32-3.36 (m, 1H), 3.56 (s, 3H), 3.76 (s, 3H), 3.84-3.87 (m, 2H), 6.84 (d, J=8.4 Hz, 2H), 7.04 (d, J=8.4 Hz, 2H), 7.22 (d, J=8.0 Hz, 1H), 7.36 (d, J=10.8 Hz, 1H), 8.54-7.58 (m, 11H). [M+H] Calc'd for C$_{25}$H$_{26}$FN$_5$O$_2$, 448; Found, 448.

Example 12: 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile

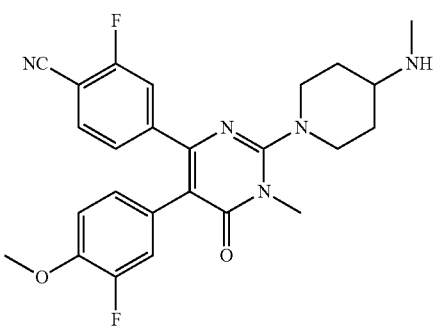

The title compound was prepared as the hydrochoride salt in 7% overall yield according to the general procedure for the preparation of Example 1. $^1$H NMR (400 MHz, CD$_3$OD): δ 1.78-1.88 (m, 2H), 2.17-2.20 (m, 2H), 2.73 (s, 3H), 3.05-3.11 (m, 2H), 3.30-3.35 (m, 1H), 3.54 (s, 3H), 3.82 (s, 3H), 3.83-3.86 (m, 2H), 6.76 (d, J=8.4 Hz, 1H), 6.93-6.99 (m, 2H), 7.20 (d, J=8.4 Hz, 1H), 7.38 (d, J=10.4 Hz, 1H), 8.55-7.589 (m, 1H). [M+H] Calc'd for C$_{25}$H$_{25}$F$_2$N$_5$O$_2$, 466. Found, 466.

Preparation 13A: 2,6-dichloro-3-ethyl-3H-pyrimidin-4-one

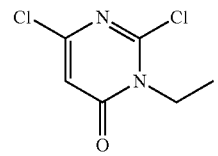

A solution of 2,6-dichloro-pyrimidin-4-ol (1.0 g, 6.1 mmol) and K$_2$CO$_3$ (1.1 g, 7.9 mmol) in DMF (10 mL) was stirred at RT for 15 min. The reaction mixture was cooled to 0° C., and iodoethane (1.1 mL, 6.7 mmol) was added dropwise. After stirring overnight at RT, the reaction mixture was diluted with EA, washed with brine, dried (Na$_2$SO$_4$) and concentrated in vacuo. The residue was purified by silica chromatography (20:1, EA:PE) to give 330 mg (28%) of the title compound. $^1$H NMR (400 MHz, CDCl$_3$): δ 1.37 (t, J=7.6 Hz, 3H), 4.76 (q, J=6.8 Hz, 2H), 6.67 (s, 1H). [M+H] Calc'd for C$_6$H$_6$Cl$_2$N$_2$O, 193, 195, 197. Found, 193, 195, 197.

Preparation 13B: [1-(4-chloro-1-ethyl-6-oxo-1,6-dihydro-pyrimidin-2-yl)-piperidin-4-yl]-carbamic Acid Tert-Butyl Ester

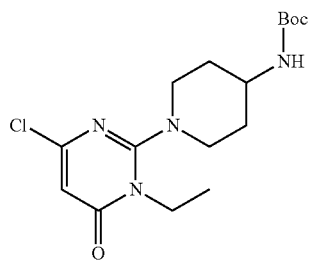 [SMILES: CCn1c(N2CCC(NC(=O)OC(C)(C)C)CC2)nc(Cl)cc1=O]

A solution of 2,6-dichloro-3-ethyl-3H-pyrimidin-4-one (320 mg, 1.64 mmol), DIEA (423 mg, 3.28 mmol) and (tert-butoxy)-N-(4-piperidyl)carboxamide (328 mg, 1.64 mmol) in DMF (10 mL) was heated to 120° C. for 1 h. The solvent was concentrated in vacuo and the residue was purified by silica chromatography (1:5, EA:PE) to give 210 mg (36%) of the title compound as a yellow solid. $^1$H NMR (400 MHz, CDCl$_3$): δ 1.25-1.32 (m 2H), 1.35 (t, J=7.2 Hz, 3H), 1.96-2.02 (m, 2H), 2.98-3.06 (m, 2H), 3.70 (br, 1H), 4.30 (q, J=5.2 Hz, 2H), 4.44 (br, 1H), 4.57-4.61 (m, 2H), 5.95 (s, 1H). [M+H] Calc'd for C$_{16}$H$_{25}$ClN$_4$O$_3$, 357, 359. Found, 357, 359.

Preparation 13C: {1-[4-(4-cyano-3-fluoro-phenyl)-1-ethyl-6-oxo-1,6-dihydro-pyrimidin-2-yl]-piperidin-4-yl}-carbamic Acid Tert-Butyl Ester

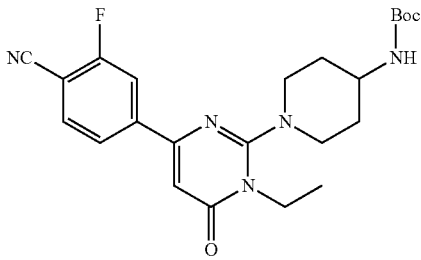 [SMILES: CCn1c(N2CCC(NC(=O)OC(C)(C)C)CC2)nc(-c2ccc(C#N)c(F)c2)cc1=O]

A mixture of [1-(4-chloro-1-ethyl-6-oxo-1,6-dihydro-pyrimidin-2-yl)-piperidin-4-yl]-carbamic acid tert-butyl ester (210 mg, 0.59 mmol) in $CH_3CN$ (10 mL), 3-fluoro-4-cyanophenylboronic acid (126 mg, 0.77 mmol), $Pd(PPh)_3$ (14 mg, 0.012 mmol) and 0.4 M $Na_2CO_3$ (4.5 mL, 1.77 mmol) was stirred at 90° C. overnight under $N_2$ atmosphere. The organic was concentrated in vacuo, and the aqueous extracted with DCM (2×). The combined organics were washed with brine, dried ($Na_2SO_4$) and concentrated. The residue was purified by silica chromatography (1:2, EA:PE) to give 185 mg (64%) of the title compound as a yellow solid. [M+H] Calc'd for $C_{23}H_{28}FN_5O_3$, 442. Found, 442.

Example 13: 4-[2-(4-amino-piperidin-1-yl)-1-ethyl-6-oxo-1,6-dihydro-pyrimidin-4-yl]-2-fluoro-benzonitrile

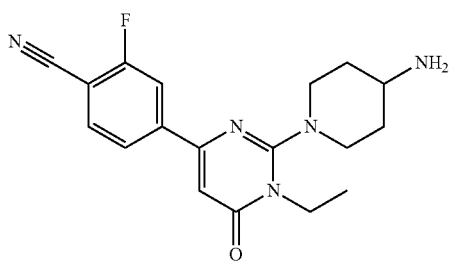 [SMILES: CCn1c(N2CCC(N)CC2)nc(-c2ccc(C#N)c(F)c2)cc1=O]

To a mixture of {1-[4-(4-cyano-3-fluoro-phenyl)-1-ethyl-6-oxo-1,6-dihydro-pyrimidin-2-yl]-piperidin-4-yl}-carbamic acid tert-butyl ester (180 mg, 0.41 mmol) in EA (5 mL) was added a 4 M solution of HCl in EA (3 mL). The reaction mixture was stirred for 30 min. The solvent was evaporated in vacuo to give 150 mg of the titled compound (97%) as a yellow solid (HCl salt). $^1H$ NMR (400 MHz, $CD_3OD$): δ 1.28 (t, J=7.2 Hz, 1H), 1.48-1.52 (m, 2H), 1.99-2.02 (m, 2H), 2.94-3.01 (m, 2H), 3.33-3.38 (m, 1H), 6.81 (q, J=6.8 Hz, 2H), 4.85-4.88 (m, 2H), 6.95 (s, 1H), 7.73 (t, J=8.0 Hz, 1H), 7.90-7.95 (m, 2H). [M+H] Calc'd for $C_{18}H_{20}FN_5O$, 342. Found, 342.

Preparation 14A: {1-[4-(4-cyano-3-fluoro-phenyl)-5-cyclopentylethynyl-1-methyl-6-oxo-1,6-dihydro-pyrimidin-2-yl]-piperidin-4-yl}-carbamic Acid Tert-Butyl Ester

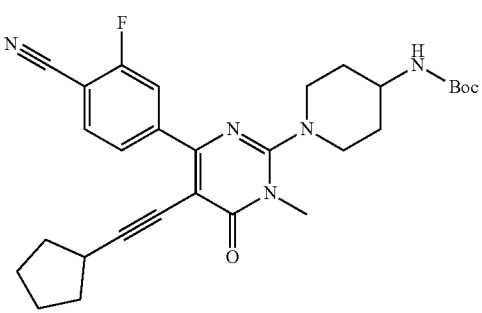 [SMILES: Cn1c(N2CCC(NC(=O)OC(C)(C)C)CC2)nc(-c2ccc(C#N)c(F)c2)c(C#CC2CCCC2)c1=O]

A mixture of tert-butyl 1-(5-chloro-4-(3-fluoro-4-cyanophenyl)-1-methyl-6-oxo-1,6-dihydropyrimidin-2-yl)piperidin-4-ylcarbamate (200 mg, 0.43 mmol), ethynyl-cyclopentane (82 mg, 0.87 mmol), $Pd(MeCN)_2Cl_2$ (4.5 mg, 0.017 mmol), X-Phos (10 mg, 0.022 mmol) and $K_2CO_3$ (120 mg, 0.87 mmol) in ACN (15 mL) was stirred overnight at 95° C. in a sealed tube. The reaction mixture was cooled to RT and the solvent was concentrated in vacuo. The residue was purified by silica chromatography (1:2, EA:PE) to give 100 mg (45%) of the title compound. [M+H] Calc'd for $C_{29}H_{34}FN_5O_3$, 519. Found, 519.

Example 14: 4-[2-(4-amino-piperidin-1-yl)-5-cyclopentylethynyl-1-methyl-6-oxo-1,6-dihydro-pyrimidin-4-yl]-2-fluoro-benzonitrile

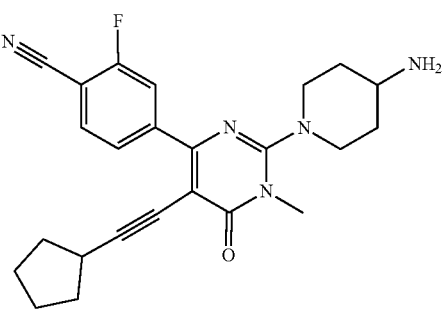 [SMILES: Cn1c(N2CCC(N)CC2)nc(-c2ccc(C#N)c(F)c2)c(C#CC2CCCC2)c1=O]

The title compound was prepare as the hydrochloride salt in 70% overall yield according to the general procedure for the preparation of Example 1. $^1H$ NMR (400 MHz, $CDCl_3$): δ 1.50-1.74 (m, 8H), 1.94-1.99 (m, 4H), 2.88-3.01 (m, 4H), 3.51 (s, 3H), 3.60 (d, J=13.2 Hz, 2H), 7.63-7.67 (m, 1H), 8.07-8.11 (m, 2H). [M+H] Calc'd for $C_{24}H_{26}FN_5O$, 419. Found, 419.

Preparation 15A: (2,4,5-trichloro-6-oxo-6H-pyrimidin-1-yl)-acetic Acid Methyl Ester

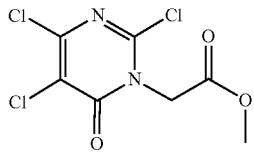

To a solution of 2,5,6-trichloro-3H-pyrimidin-4-one (20.0 g, 0.1 mol) in DMF (150 mL) was added NaH (60% in mineral oil, 6.0 g, 0.12 mol) in portions at 0° C. and the mixture was stirred for 30 min. Bromoacetic acid methyl ester (18.3 g, 0.12 mol) was then added, and the reaction mixture was stirred at RT overnight. The solution was diluted with water (800 mL) and extracted with EA (200 mL, 3×). The combined organics were washed with water (800 mL, 3×), washed with brine (500 mL), dried (Na$_2$SO$_4$) and concentrated. The residue was purified by silica chromatography (1:50, EA:PE) to give 6.0 g of the title product (22%). $^1$H NMR (400 MHz, CDCl$_3$): δ 3.80 (s, 3H), 5.04 (s, 2H). [M+H] Calc'd for C$_7$H$_5$Cl$_3$N$_2$O$_3$, 271. Found, 271.

Preparation 15B: [2-(4-tert-butoxycarbonylamino-piperidin-1-yl)-4,5-dichloro-6-oxo-6H-pyrimidin-1-yl]-acetic Acid Methyl Ester

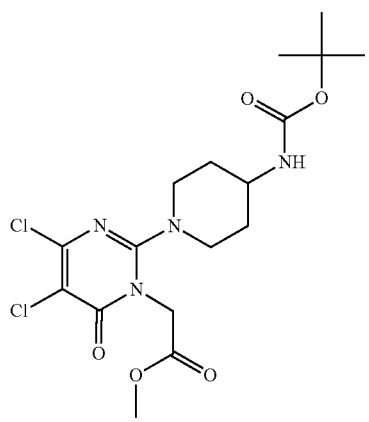 [SMILES: COC(=O)Cn1c(N2CCC(NC(=O)OC(C)(C)C)CC2)nc(Cl)c(Cl)c1=O]

To a solution of (2,4,5-trichloro-6-oxo-6H-pyrimidin-1-yl)-acetic acid methyl ester (6.0 g, 22.4 mmol) and piperidin-4-yl-carbamic acid tert-butyl ester (4.9 g, 24.4 mmol) in DMF (50 mL) was added DIPEA (5.7 g, 44.3 mmol) dropwise at RT, and the mixture was stirred overnight. The reaction mixture was diluted with water (500 mL), and the solids were collected by filtration. The solids were then dissolved in DCM (100 mL), washed with water (100 mL, 3×), washed with brine (100 mL), dried (Na$_2$SO$_4$) and concentrated. The residue was purified by silica chromatography (1:2 to 1:1, DCM:PE) to give 6.3 g of the title product (64%). $^1$H NMR (400 MHz, CDCl$_3$): δ 1.22-1.34 (m, 2H), 1.45 (s, 9H), 1.97-2.03 (m, 2H), 2.96-3.09 (m, 2H), 3.68-3.69 (m, 1H), 3.75 (s, 3H), 4.42-4.44 (m, 3H), 4.84 (s, 2H). [M+H] Calc'd for C$_{17}$H24C$_{12}$N$_4$O$_5$, 435; Found, 435.

Preparation 15C: [2-(4-tert-butoxycarbonylamino-piperidin-1-yl)-5-chloro-4-(4-cyano-3-fluoro-phenyl)-6-oxo-6H-pyrimidin-1-yl]-acetic Acid Methyl Ester

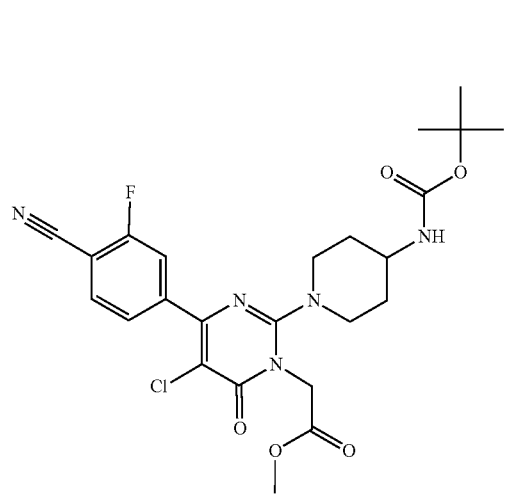 [SMILES: COC(=O)Cn1c(N2CCC(NC(=O)OC(C)(C)C)CC2)nc(-c2ccc(C#N)c(F)c2)c(Cl)c1=O]

A mixture of [2-(4-tert-butoxycarbonylamino-piperidin-1-yl)-4,5-dichloro-6-oxo-6H-pyrimidin-1-yl]-acetic acid methyl ester (5.76 g, 13.2 mmol), 4-cyano-3-fluoro benzeneboronic acid (2.24 g, 16.1 mmol), Pd(PPh$_3$)$_4$ (306 mmol, 0.26 mmol) and Na$_2$CO$_3$ (2.8 g, 26.5 mmol) in DMF:H$_2$O (50 mL:10 mL) was stirred at 65° C. overnight under nitrogen atmosphere. The reaction mixture was concentrated, and the residue was purified by silica chromatography (1:20 to 1:0, EA:PE) to give 2.4 g of the title product (43%). $^1$H NMR (400 MHz, CDCl$_3$): δ 1.27-1.37 (m, 2H), 1.45 (s, 9H), 1.99-2.02 (m, 2H), 2.99-3.06 (m, 2H), 3.68-3.76 (m, 1H), 3.78 (s, 3H), 4.42-4.52 (m, 3H), 4.90 (s, 2H), 7.63-7.66 (m, 1H), 7.67-7.71 (m, 2H). [M+H] Calc'd for C$_{24}$H$_{27}$ClFN$_5$O$_5$, 520. Found, 520.

Preparation 15D: [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic Acid Methyl Ester

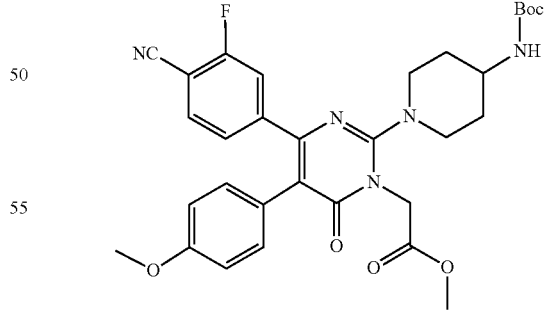

A solution of [2-(4-tert-butoxycarbonylamino-piperidin-1-yl)-5-chloro-4-(4-cyano-3-fluoro-phenyl)-6-oxo-6H-pyrimidin-1-yl]-acetic acid methyl ester (2.2 g, 4.2 mmol), p-methoxyboronic acid (1.9 g, 12.7 mmol), Pd-118 (274 mg, 0.42 mmol) and K$_2$CO$_3$ (1.2 g, 8.4 mmol) in DMF (50 mL) was stirred at 145° C. for 6 h under nitrogen atmosphere. The reaction mixture was diluted with water and extracted with EA (3×). The combined organics were washed with water, washed brine, dried (Na$_2$SO$_4$) and concentrated. The residue was purified by preparative HPLC to give 600 mg of the title product (24%). [M+H] Calc'd for C$_{31}$H$_{34}$FN$_5$O$_6$, 592. Found, 592.

Preparation 15E: 4-[2-(4-amino-piperidin-1-yl)-1-cyclopropylmethyl-6-oxo-1,6-dihydro-pyrimidin-4-yl]-2-fluoro-benzonitrile

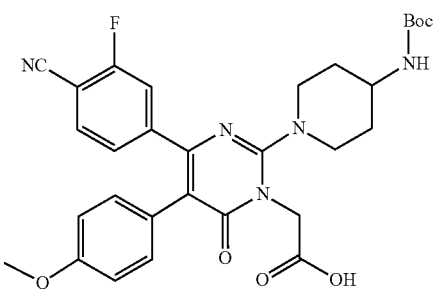 [SMILES: COc1ccc(-c2c(-c3ccc(C#N)c(F)c3)nc(N3CCC(NC(=O)OC(C)(C)C)CC3)n(CC(=O)O)c2=O)cc1]

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid methyl ester (600 mg, 1.02 mmol) in MeOH (10 mL) was added a 2N NaOH solution (5 mL). After completion of the reaction, the solution was acidified with 1N HCl and extracted with EA (3×). The combined organics were washed with brine, dried (Na$_2$SO$_4$) and concentrated. The residue was purified by preparative HPLC to give 240 mg of the title product as a yellow solid (41%). [M+H] Calc'd for C$_{30}$H$_{32}$FN$_5$O$_6$, 578. Found, 578.

Example 15: [2-(4-amino-piperidin-1-yl)-4-(4-cyano-3-fluoro-phenyl)-5-(4-methoxy-phenyl)-6-oxo-6H-pyrimidin-1-yl]-acetic Acid

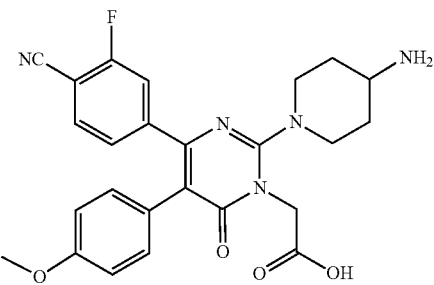 [SMILES: COc1ccc(-c2c(-c3ccc(C#N)c(F)c3)nc(N3CCC(N)CC3)n(CC(=O)O)c2=O)cc1]

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid (100 mg, 0.15 mmol) in EA (10 mL) was added a 5N HCl solution in EA (5 mL). The reaction mixture was stirred at RT for 2 h, and the solvent was concentrated in vacuo. The residue was purified by preparative HPLC to give 25 mg of the title product as HCl salt (32%). $^1$H NMR (400 MHz, CD$_3$OD): δ 1.53-1.56 (m, 2H), 2.00-2.03 (m, 2H), 3.00-3.07 (m, 2H), 3.35-3.39 (m, 1H), 3.67 (s, 3H), 4.70 (s, 2H), 4.76-4.77 (m, 2H), 6.74 (d, J=8.4 Hz, 2H), 6.96 (d, J=8.8 Hz, 2H), 7.17 (d, J=8.4 Hz, 1H), 7.26 (d, J=10.0 Hz, 1H), 7.50 (dd, J=7.2, 8.0 Hz, 1H). [M+H] Calc'd for C$_{25}$H$_{24}$FN$_5$O$_4$, 478; Found, 478.

Preparation 16A: {1-[1-carbamoylmethyl-4-(4-cyano-3-fluoro-phenyl)-5-(4-methoxy-phenyl)-6-oxo-1,6-dihydro-pyrimidin-2yl]-piperidin-4-yl}-carbamic Acid Tert-Butyl Ester

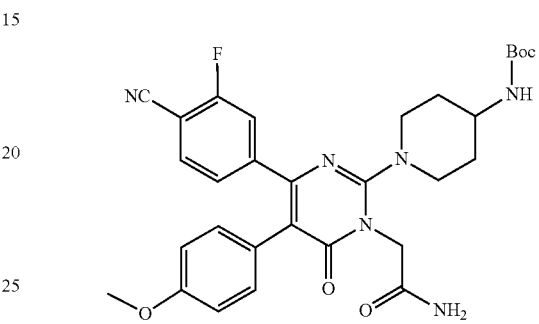

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid (120 mg, 0.2 mmol) in DMF (5 mL) was added NH$_4$Cl (17 mg, 0.3 mmol), HATU (95 mg, 0.25 mmol) and DIEA (25 mg, 0.4 mmol). After completion of the reaction, the solution was diluted with H$_2$O and extracted with DCM for (3×). The combined organics were dried (Na$_2$SO$_4$) and concentrated. The residue was purified by preparative HPLC to give 50 mg of the title product as a yellow solid (43%). [M+H] Calc'd for C$_{30}$H$_{33}$FN$_6$O$_5$, 577. Found, 577.

Example 16: 2-[2-(4-amino-piperidin-1-yl)-4-(4-cyano-3-fluoro-phenyl)-5-(4-methoxy-phenyl)-6-oxo-6H-pyrimidin-1-yl]-acetamide

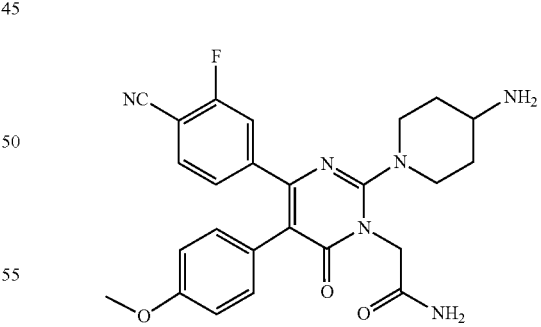

The title compound was prepared as the hydrochloride salt in 96% yield according to the procedure for the preparation of Example 15. $^1$H NMR (400 MHz, CD$_3$OD): δ 1.49-1.53 (m, 2H), 1.98-2.01 (m, 2H), 2.97-3.04 (m, 2H), 3.33-3.36 (m, 1H), 3.68 (s, 3H), 4.69 (s, 2H), 4.75-4.78 (m, 2H), 6.75 (d, J=8.4 Hz, 2H), 6.99 (d, J=8.8 Hz, 2H), 7.16 (dd, J=1.2, 8.0 Hz, 1H), 7.25 (dd, J=0.8, 10.4 Hz, 1H), 7.49 (dd, J=7.2, 8.0 Hz, 1H). [M+H] Calc'd for C$_{25}$H$_{25}$FN$_6$O$_3$, 477. Found, 477.

Preparation 17A: 2,6-dichloro-3-(3-methoxy-propyl)-3H-pyrimidin-4-one

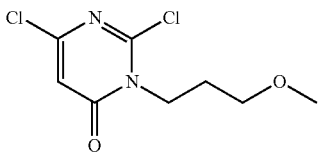

To a solution of 2,6-dichloro-3H-pyrimidin-4-one (600 mg, 3.65 mmol) in DMF (10 mL) was added $K_2CO_3$ (1.0 g, 7.3 mmol) and the mixture was stirred at RT for 10 min. 1-Bromo-3-methoxy-propane (101 mg, 7.3 mmol) was then added dropwise at 0° C., and the mixture was stirred at RT overnight. DMF was concentrated in vacuo, and the residue was purified by silica chromatography to give 400 mg of the title compound (47%). [M+H] Calc'd for; Calc'd for $C_8H_{10}Cl_2N_2O_2$, 237. Found, 237.

Preparation 17B: {1-[4-chloro-1-(3-methoxy-propyl)-6-oxo-1,6-dihydro-pyrimidin-2-yl]-piperidin-4-yl}-carbamic Acid Tert-Butyl Ester

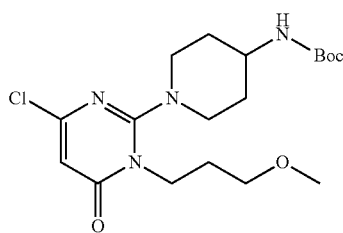 [SMILES: COCCCn1c(N2CCC(NC(=O)OC(C)(C)C)CC2)nc(Cl)cc1=O]

A solution of 2,6-dichloro-3-(3-methoxy-propyl)-3H-pyrimidin-4-one (400 mg, 1.68 mmol), piperidin-4-yl-carbamic acid tert-butyl ester (405 mg, 2 mmol) and DIEA (260 mg, 2.0 mmol) in DMF (20 mL) was stirred at 85° C. for 2 h. The solvent was concentrated, and the residue was purified by silica chromatography to give 500 mg of the title compound (75%). [M+H] Calc'd for $C_{18}H_{29}ClN_4O_4$, 400. Found, 400.

Preparation 17C: {1-[4-(4-cyano-3-fluoro-phenyl)-1-(3-methoxy-propyl)-6-oxo-1,6-dihydro-pyrimidin-2-yl]-piperidin-4-yl}-carbamic Acid Tert-Butyl Ester

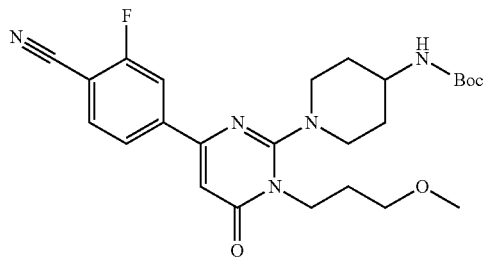 [SMILES: COCCCn1c(N2CCC(NC(=O)OC(C)(C)C)CC2)nc(-c2ccc(C#N)c(F)c2)cc1=O]

A mixture of {1-[4-chloro-1-(3-hydroxy-propyl)-6-oxo-1,6-dihydro-pyrimidin-2-yl]-piperidin-4-yl}-carbamic acid tert-butyl ester (200 mg, 0.5 mmol), 4-cyano-3-fluorophenyl boric acid (107 mg, 0.65 mmol), $Pd(PPh_3)_4$ (12 mg, 0.01 mmol) and 0.4M $Na_2CO_3$ solution (4 mL) in ACN was stirred at 85° C. overnight. The reaction mixture was diluted with water and extracted with EA (3×). The reaction mixture was stirred at RT for 2 h and the solvent was concentrated in vacuo. The residue was purified by silica chromatography to give 240 mg of the title product (99%). [M+H] Calc'd for $C_{25}H_3FN_5O_4$, 485. Found, 485.

Example 17: 4-[2-(4-amino-piperidin-1-yl)-1-(3-hydroxy-propyl)-6-oxo-1,6-dihydro-pyrimidin-4-yl]-2-fluoro-benzonitrile

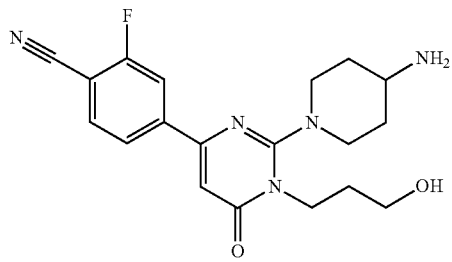 [SMILES: N#Cc1ccc(-c2cc(=O)n(CCCO)c(N3CCC(N)CC3)n2)cc1F]

To a solution of {1-[4-(4-cyano-3-fluoro-phenyl)-1-(3-methoxy-propyl)-6-oxo-1,6-dihydro-pyrimidin-2-yl]-piperidin-4-yl}-carbamic acid tert-butyl ester (200 mg, 0.41 mmol) in DCM was added 1M $BBr_3$ (4 mL) at −78° C. The mixture was stirred at RT for 2 h and quenched at 0° C. with MeOH. The solution was washed with aqueous saturated $NaHCO_3$. The organic layer was dried and concentrated. The residue was purified by preparative HPLC to give 35 mg of the title product as the hydrochloride salt (23%). $^1$H NMR (400 MHz, $CD_3OD$): 1.65-1.69 (m, 2H), 1.97-2.19 (m, 4H), 3.13-3.22 (m, 2H), 3.48-3.55 (m, 1H), 3.73 (t, J=8.0 Hz, 2H), 4.55 (t, J=8.0 Hz, 2H), 4.94-4.95 (m, 2H), 6.71 (s, 1H), 7.88-8.05 (m, 3H). [M+H] Calc'd for $C_{19}H_{22}FN_5O_2$, 371. Found, 371.

Preparation 18A: {1-[5-benzofuran-5-yl-4-(4-cyano-3-fluoro-phenyl)-1-methyl-6-oxo-1,6dihydro-pyrimidin-2-yl]-piperidin-4-yl}-carbamic Acid Tert-Butyl Ester

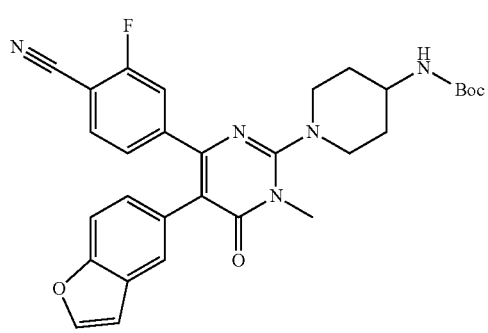 [SMILES: Cn1c(N2CCC(NC(=O)OC(C)(C)C)CC2)nc(-c2ccc(C#N)c(F)c2)c(-c2ccc3occc3c2)c1=O]

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (200 mg, 0.45 mmol), benzofuran-5-boronic acid (120 mg, 0.68 mmol), $Pd(PPh_3)_4$ (26 mg, 0.05 mmol) and 2M Na$_2$CO$_3$ (0.9 mL) in 1,4-dioxane (200 mL) was refluxed overnight under N$_2$ atmosphere. The reaction mixture was diluted with water and extracted with EA (3×). The combined organics were washed with brine, dried (Na$_2$SO$_4$) and concentrated. The residue was purified by silica chromatography to give 100 mg of the title product (42%). [M+H] Calc'd for C$_{30}$H$_{30}$FN$_5$O$_4$, 543. Found, 543.

Example 18: 4-[2-(4-amino-piperidin-1-yl)-5-benzofuran-5-yl-1-methyl-6-oxo-1,6-dihydro-pyrimidin-4-yl]-2-fluoro-benzonitrile

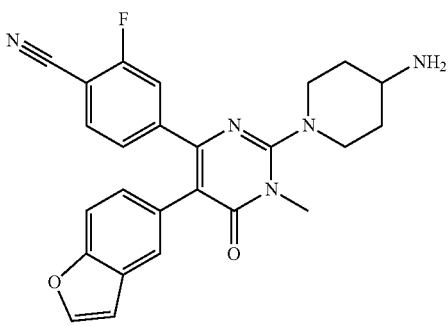 [SMILES: Cn1c(N2CCC(N)CC2)nc(-c2ccc(C#N)c(F)c2)c(-c2ccc3occc3c2)c1=O]

To a solution of Preparation 18A (60 mg, 0.11 mmol) in EA (20 mL) was added a 4M HCl solution in EA (10 mL). The mixture was stirred at RT for 2 h. The solvent was concentrated in vacuo to give 43 mg of the title product as the hydrochloride salt (53%). $^1$H NMR (400 MHz, CD$_3$OD): 1.85-1.92 (m, 2H), 2.13-2.18 (m, 2H), 3.10 (t, J=4.0 Hz, 2H), 3.31-3.33 (m, 1H), 3.61 (s, 3H), 3.87 (d, J=13.2 Hz, 2H), 6.65-7.21 (m, 3H), 7.38-7.76 (m, 4H), 7.76 (s, 1H). [M+H] Calc'd for C$_{25}$H$_{22}$FN$_5$O$_2$, 443. Found, 443.

Preparation 19A: {1-[5-cyano-4-(4-cyano-3-fluorophenyl)-1-methyl-6-oxo-1,6-dihydro-pyrimidin-2-yl]-piperidin-4-yl}-carbamic Acid Tert-Butyl Ester

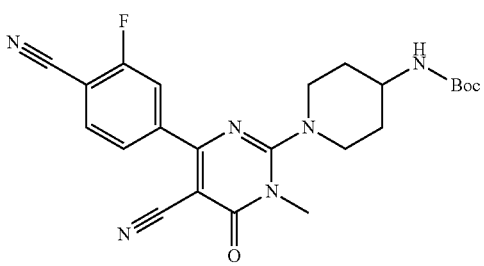 [SMILES: Cn1c(N2CCC(NC(=O)OC(C)(C)C)CC2)nc(-c2ccc(C#N)c(F)c2)c(C#N)c1=O]

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (460 mg, 1 mmol), Zn(CN)$_2$ (175 mg, 1.5 mmol) and Pd(PPh$_3$)$_4$(116 mg, 0.0.1 mmol) in DMF (5 mL) was stirred for 4 h at 150° C. under N$_2$ atmosphere. The reaction mixture was cooled to RT and filtered. The filtrate was concentrated in vacuo, and the residue was purified by preparative HPLC to give 150 mg of the title product as a yellow solid (33%). [M+H] Calc'd for C$_{23}$H$_{25}$FN$_6$O$_3$, 453. Found, 453.

Example 19: 2-(4-amino-piperidin-1-yl)-4-(4-cyano-3-fluoro-phenyl)-1-methyl-6-oxo-1,6-dihydro-pyrimidine-5-carbonitrile

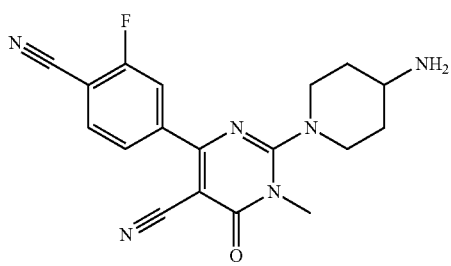 [SMILES: Cn1c(N2CCC(N)CC2)nc(-c2ccc(C#N)c(F)c2)c(C#N)c1=O]

To a solution of {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5N HCl solution in EA (5 mL). The reaction mixture was stirred at RT for 2 h, and the solvent was concentrated in vacuo to give 120 mg of the title product as HCl salt (94%). $^1$H NMR (400 MHz, CD$_3$OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C$_{18}$H$_{17}$FN$_6$O, 353; Found, 353.

Example 20: 4-[2-(4-aminopiperidin-1-yl)-5-chloro-1-methyl-6-oxopyrimidin-4-yl]-2-fluorobenzonitrile

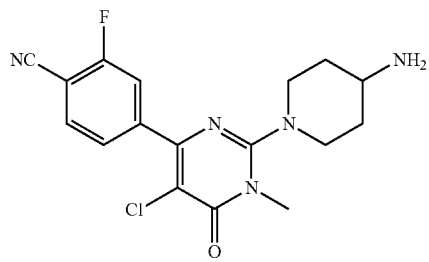 [SMILES: Cn1c(N2CCC(N)CC2)nc(-c2ccc(C#N)c(F)c2)c(Cl)c1=O]

To a solution of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5N HCl solution in EA (5 mL). The reaction mixture was stirred at RT for 2 h, and the solvent was concentrated in vacuo to give 120 mg of the title product as HCl salt (94%). $^1$H NMR (400 MHz, CD$_3$OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C$_{18}$H$_{17}$FN$_6$O, 353; Found, 353. $^1$H NMR (400 MHz, METHANOL-d$_4$): δ ppm 1.73-1.91 (m, 2H), 2.18 (d, J=12.13 Hz, 2H), 3.06 (t, J=12.76 Hz, 2H), 3.33-3.40 (m, 1H), 3.57 (s, 3H), 3.83 (d, J=13.14 Hz, 2H), 7.75-7.93 (m, 3H).

TABLE 3

| Chemical Synthesis Example | Structure (prepared by procedure of cited Example) | MS (ESI) m/z | NMR spectrum data |
|---|---|---|---|
| 21 | Prepared by the procedure of Example 1 | 433 | ¹H NMR (400 MHz, CD₃OD): δ 1.89-1.93 (m, 2H), 2.18-2.21 (m, 2H), 2.73 (s, 3H), 2.74 (s, 3H), 3.11-3.17 (m, 2H), 3.33-3.39 (m, 1H), 3.57 (s, 3H), 3.4-3.97 (m, 2H), 7.28 (d, J = 8.0 Hz, 1H), 7.55 (d, J = 10.0 Hz, 1H), 7.63-7.67 (m, 1H), 7.74 (d, J = 8.4 Hz, 1H), 8.12 (d, J = 8.4 Hz, 1H), 8.65 (s, 1H). |
| 22 | Prepared by the procedure of Example 1 | 492 | ¹H NMR (400 MHz, CDCl₃): δ 1.74-1.80 (m, 4H), 1.93-1.97 (m, 2H), 3.11 (s, 2H), 3.26-3.35 (m, 6H), 3.47 (s, 3H), 3.75 (s, 3H), 6.68 (dd, J = 1.2, 8.4 Hz, 1H), 6.86-6.72 (m, 2H), 7.11 (dd, J = 1.2, 8.0 Hz, 1H), 7.30 (dd J = 1.2, 10.8 Hz, 1H), 7.46 (dd J = 6.8, 7.6 Hz, 1H). |
| 23 | Prepared by the procedure of Example 1 | 472 | ¹H NMR (400 MHz, CD₃OD): 1.75-1.82 (m, 2H), 2.03-2.06 (m, 2H), 3.06-3.12 (m, 2H), 3.22-3.34 (m, 1H), 3.49 (s, 3H), 3.1 (d, J = 13.6 Hz, 2H), 7.07-7.09 (m, 1H), 7.36-7.38 (m, 1H), 7.51-7.55 (m, 1H), 7.66 (d, J = 8.0 Hz, 1H), 7.79-7.82 (m, 1H), 8.33 (s, 1H). |
| 24 | Prepared by the procedure of Example 1 | 439 | ¹H NMR (400 MHz, CD₃OD): 1.96-2.01 (m, 2H), 2.20-2.22 (m, 2H), 3.23-3.32 (m, 2H), 3.46-3.49 (m, 1H), 3.65 (s, 3H), 3.94-3.97 (m, 2H), 4.39 (s, 3H), 7.55-7.77 (m, 7H), 8.76 (s, 1H). |

TABLE 3-continued

| Chemical Synthesis Example | Structure (prepared by procedure of cited Example) | MS (ESI) m/z | NMR spectrum data |
|---|---|---|---|
| 25 | *[structure]*<br>Prepared by the procedure of Example 1 | 452 | ¹H NMR (300 MHz, CD₃OD): δ 1.72-1.93 (m, 3H), 1.97-2.23 (m, 1H), 3.16-3.30 (m, 2H), 3.50-3.55 (m, 2H), 3.60 (s, 3H), 3.83-3.84 (m, 1H), 3.86 (s, 3H), 6.82 (d, J = 8.1 Hz, 1H), 6.97-7.05 (m, 2H), 7.25 (d, J = 8.1 Hz, 1H), 7.44 (d, J = 10.8 Hz, 1H), 7.62 (t, J = 7.5 Hz, 1H). |
| 26 | *[structure]*<br>Prepared by the procedure of Example 1 | 453 | ¹H NMR (400 MHz, CD₃OD): 1.64-1.69 (m, 2H), 1.89-1.92 (m, 2H), 2.85-2.91 (m, 2H), 3.15-3.20 (m, 1H), 3.34 (s, 3H), 3.62 (d, J = 8.4 Hz, 2H), 3.71 (s, 3H), 6.99 (d, J = 8.4 Hz, 1H), 7.20-7.40 (m, 4H). |
| 27 | *[structure]*<br>Prepared by the procedure of Example 1 | 438 | ¹H NMR (400 MHz, CD₃OD): δ 2.19-2.22 (m, 1H), 2.49-2.51 (m, 1H), 3.63 (s, 3H), 3.75-3.81 (m, 2H), 3.87 (s, 3H), 3.87-3.93 (m, 1H), 4.02-4.06 (m, 2H), 6.80 (d, J = 8.4 Hz, 1H), 7.00 (t, J = 10.8 Hz, 2H), 7.25 (d, J = 9.6 Hz, 1H), 7.44 (d, J = 10.8 Hz, 1H), 7.61 (t, J = 7.4 Hz, 1H). |
| 28 | *[structure]*<br>Prepared by the procedure of Example 1 | 452 | ¹H NMR (400 MHz, CD₃OD): δ 1.69-1.99 (m, 3H), 2.14-2.19 (m, 1H), 3.09-3.24 (m, 2H), 3.43-3.46 (m, 1H), 3.56-3.60 (m, 4H), 3.77-3.80 (m, 1H), 3.82 (s, 3H), 6.77 (d, J = 8.0 Hz, 1H), 6.94-7.00 (m, 2H), 7.21 (d, J = 8.0 Hz, 1H), 7.39 (d, J = 10.4 Hz, 1H), 8.56-7.60 (m, 1H). |

TABLE 3-continued

| Chemical Synthesis Example | Structure (prepared by procedure of cited Example) | MS (ESI) m/z | NMR spectrum data |
|---|---|---|---|
| 29 | Prepared by the procedure of Example 1 | 438 | ¹H NMR (400 MHz, CD₃OD): δ 2.25-2.29 (m, 1H), 2.50-2.55 (m, 1H), 3.69 (s, 3H), 3.89-3.84 (m, 5H), 3.99-4.03 (m, 1H), 5.05-4.16 (m, 2H), 6.80 (d, J = 8.4 Hz, 1H), 6.97-7.03 (m, 2H), 7.29 (dd, J = 2.4, 8.0 Hz, 1H), 7.47 (d, J = 10.4 Hz, 1H), 7.64 (dd, J = 6.8, 8.0 Hz, 1H). |
| 30 | Prepared by the procedure of Example 1 | 434 | ¹H NMR (400 MHz, CD₃OD): δ 1.73-2.02 (m, 3H), 2.19-2.23 (m, 1H), 3.13-3.26 (m, 2H), 3.49-3.52 (m, 2H), 3.60 (s, 3H), 3.77-3.85 (m, 1H), 3.85 (s, 3H), 6.89 (d, J = 11.6 Hz, 2H), 7.08-7.10 (d, J = 11.6 Hz, 2H), 7.24 (d, J = 8.0 Hz, 1H), 7.41 (d, J = 10.8 Hz, 1H), 7.57-7.61 (m, 1H). |
| 31 | Prepared by the procedure of Example 1 | 434 | ¹H NMR (400 MHz, CD₃OD): δ 1.69-1.99 (m, 3H), 2.07-2.10 (m, 1H), 3.09-3.24 (m, 2H), 3.43-3.46 (m, 1H), 3.56-3.60 (m, 4H), 3.68 (s, 3H), 3.76-3.79 (m, 1H), 6.75 (d, J = 8.8 Hz, 2H), 6.96 (d, J = 9.2 Hz, 2H), 7.13 (dd, J = 2.0, 8.0 Hz, 1H), 7.27 (dd, J = 0.8, 10.4 Hz, 1H), 7.47 (dd, J = 6.8, 8.0 Hz, 1H). |
| 32 | Prepared by the procedure of Example 1 | 466 | ¹H NMR (400 MHz, CD₃OD): δ 1.41 (s, 3H), 1.82-1.85 (m, 2H), 1.91-1.99 (m, 2H), 3.22-3.25 (m, 2H), 3.47 (s, 3H), 3.50-3.57 (m, 2H), 3.75 (s, 3H) 6.69 (d, J = 8.4 Hz, 1H), 6.86-6.92 (m, 2H), 7.14 (d, J = 8.4 Hz, 1H), 7.32 (d, J = 10.8 Hz, 1H), 7.47-7.51 (m, 1H). |

TABLE 3-continued

| Chemical Synthesis Example | Structure (prepared by procedure of cited Example) | MS (ESI) m/z | NMR spectrum data |
|---|---|---|---|
| 33 | Prepared by the procedure of Example 1 | 439 | ¹H NMR (400 MHz, CD3OD): δ 1.95-1.99 (m, 2H), 2.19-2.22 (m, 2H), 3.20-3.26 (m, 2H), 3.45-3.50 (m, 1H), 3.63 (s, 3H), 3.90 (d, J = 12.8 Hz, 2H), 4.06 (s, 3H), 7.21 (d, J = 8.4 Hz, 1H), 7.48-7.57 (m, 6H), 7.96 (s, 1H). |
| 34 | Prepared by the procedure of Example 1 | 476 | ¹H NMR (400 MHz, CD₃OD): δ 1.75-1.79 (m, 2H), 2.02-2.05 (m, 2H), 3.00-3.06 (m, 2H), 3.21-3.31 (m, 1H), 3.48 (s, 3H), 3.72-3.75 (m, 2H), 4.77-4.81 (m, 2H), 7.22 (s, 1H), 7.31 (d, J = 8.0 Hz, 1H), 7.39 (d, J = 2.0 Hz, 1H), 7.60-7.64 (m, 2H). |
| 35 | Prepared by the procedure of Example 1 | 457 | ¹H NMR (400 MHz, CD₃OD): 1.85-1.99 (m, 2H), 2.18-2.20 (m, 2H), 3.19-3.24 (m, 2H), 3.46-3.50 (m, 1H), 3.86 (s, 3H), 3.86-3.92 (m, 2H), 4.10 (s, 3H), 7.21-7.25 (m, 2H), 7.40-7.53 (m, 4H), 8.01 (s, 1H). |
| 36 | Prepared by the procedure of Example 1 | 458 | ¹H NMR (400 MHz, CD₃OD): δ 1.79-1.82 (m, 2H), 2.04-2.07 (m, 2H), 3.09-3.15 (m, 2H), 3.32-3.38 (m, 1H), 3.50 (s, 3H), 3.76-3.79 (m, 2H), 4.74-4.78 (m, 2H), 7.12 (s, 1H), 7.55 (d, J = 8.4 Hz, 2H), 7.62 (s, 1H), 7.67 (d, J = 8.0 Hz, 2H). |

TABLE 3-continued

| Chemical Synthesis Example | Structure (prepared by procedure of cited Example) | MS (ESI) m/z | NMR spectrum data |
|---|---|---|---|
| 37 | Prepared by the procedure of Example 1 | 458 | ¹H NMR (400 MHz, CD₃OD): δ 1.98-2.04 (m, 2H), 2.21-2.24 (m, 2H), 3.27-3.30 (m, 2H), 3.50-3.52 (m, 1H), 3.65 (s, 3H), 3.98 (d, J = 12.8 Hz, 2H), 4.42 (s, 3H), 7.33 (d, J = 8.0 Hz, 1H), 7.49 (d, J = 10.0 Hz, 1H), 7.60-7.73 (m, 3H), 7.84 (s, 1H), 8.85 (s, 1H). |
| 38 | Prepared by the procedure of Example 1 | 452 | ¹H NMR (400 MHz, CD₃OD): 1.87-1.94 (m, 2H), 2.15 (d, J = 12.0 Hz, 2H), 3.13 (t, J = 8.4 Hz, 2H), 3.39-3.43 (m, 1H), 3.59 (s, 3H), 3.87 (d, J = 12.8 Hz, 2H), 3.97 (s, 3H), 6.79 (d, J = 8.8 Hz, 2H), 7.55 (d, J = 8.4 Hz, 2H), 7.70 (d, J = 8.4 Hz, 2H). |
| 39 | Prepared by the procedure of Example 1 | 448 | ¹H NMR (400 MHz, CD₃OD): δ 1.91-1.94 (m, 2H), 2.16-2.19 (m, 2H), 3.15-3.21 (m, 2H), 3.50-3.52 (m, 1H), 3.61 (s, 3H), 3.90 (d, J = 12.4 Hz, 2H), 7.22 (d, J = 8.0 Hz, 1H), 7.30 (d, J = 8.0 Hz, 2H), 7.43 (d, J = 10.8 Hz, 1H), 7.59 (t, J = 7.2 Hz, 1H), 7.86 (d, J = 8.0 Hz, 2H). |
| 40 | Prepared by the procedure of Example 1 | 461 | ¹H NMR (400 MHz, CD₃OD): δ 1.88-1.91 (m, 2H), 2.12-2.13 (m, 2H), 2.94 (s, 3H), 3.13-3.15 (m, 2H), 3.30-3.34 (m, 1H), 3.61 (s, 3H), 3.89 (d, J = 14.4 Hz, 2H), 7.00 (d, J = 8.0 Hz, 1H), 7.11 (d, J = 12.0 Hz, 1H), 7.53 (d, J = 12.0 Hz, 2H), 7.61-7.64 (m, 3H). |

TABLE 3-continued

| Chemical Synthesis Example | Structure (prepared by procedure of cited Example) | MS (ESI) m/z | NMR spectrum data |
|---|---|---|---|
| 41 | Prepared by the procedure of Example 1 | 447 | ¹H NMR (400 MHz, CD₃OD): δ 1.87-1.91 (m, 2H), 2.14-2.16 (m, 2H), 3.15 (t, J = 12.0 Hz, 2H), 3.30-3.40 (m, 1H), 3.61 (s, 3H), 3.89 (d, J = 14.0 Hz, 2H), 7.01 (d, J = 8.0 Hz, 1H), 7.13 (d, J = 12.0 Hz, 1H) 7.52-7.77 (m, 5H). |
| 42 | Prepared by the procedure of Example 1 | 459 | ¹H NMR (400 MHz, CD₃OD): δ 1.78-1.79 (m, 2H), 2.03-2.05 (m, 2H), 3.00-3.06 (m, 2H), 3.21-3.31 (m, 1H), 3.49 (s, 3H), 3.75-3.78 (m, 2H), 4.32 (s, 2H), 7.06 (dd, J = 1.2, 8.0 Hz, 1H), 7.12 (dd, J = 1.2, 8.0 Hz, 1H), 7.31-7.36 (m, 1H), 7.42 (dd, J = 6.4, 7.6 Hz, 1H), 7.58 (d, J = 7.6 Hz, 1H). |
| 43 | Prepared by the procedure of Example 1 | 448 | ¹H NMR (400 MHz, CD₃OD): δ 1.77-1.80 (m, 2H), 2.02-2.05 (m, 2H), 3.01-3.05 (m, 2H), 3.35-3.36 (m, 1H), 3.49 (s, 3H), 3.74-3.98 (m, 2H), 7.07 (dd, J = 1.6, 8.4 Hz, 1H), 7.27-7.32 (m, 3H), 7.44 (dd, J = 6.8, 8.0 Hz, 1H), 7.73 (d, J = 1.2 Hz, 1H), 7.84 (d, J = 7.2 Hz, 1H). |
| 44 | Prepared by the procedure of Example 1 | 434 | ¹H NMR (400 MHz, CD₃OD): δ 1.87-1.91 (m, 1H), 2.25-2.28 (m, 1H), 2.87-2.92 (m, 1H), 3.11-3.17 (m, 1H), 3.30-3.32 (m, 1H), 3.41-3.56 (m, 5H), 3.69-3.71 (m, 2H), 3.84 (s, 3H), 6.75 (d, J = 8.4 Hz, 1H), 6.92-6.96 (m, 2H), 7.53 (d, J = 8.0 Hz, 2H), 7.66 (d, J = 8.4 Hz, 2H). |

TABLE 3-continued

| Chemical Synthesis Example | Structure (prepared by procedure of cited Example) | MS (ESI) m/z | NMR spectrum data |
|---|---|---|---|
| 45 | *[structure]* Prepared by the procedure of Example 1 | 434 | $^1$H NMR (400 MHz, CD$_3$OD): δ 1.74-1.80 (m, 1H), 2.14-2.19 (m, 1H), 2.77-2.81 (m, 1H), 3.01-3.06 (m, 1H), 3.31-3.34 (m, 1H), 3.36-3.45 (m, 5H), 3.59-3.60 (m, 2H) 3.71 (s, 3H), 6.63 (d, J = 8.4 Hz, 1H), 6.80-6.84 (m, 2H), 7.44 (d, J = 8.0 Hz, 2H), 7.60 (d, J = 8.4 Hz, 2H). |
| 46 | *[structure]* Prepared by the procedure of Example 1 | 452 | $^1$H NMR (400 MHz, CD$_3$OD): δ 2.15-2.18 (m, 2H), 3.31-3.34 (m, 2H), 3.46-3.51 (m, 5H), 3.56-3.59 (m, 2H), 3.74 (s, 3H), 3.78-3.81 (m, 2H), 6.68 (dd, J = 1.2, 8.4 Hz, 1H), 6.85-6.89 (m, 2H), 7.12 (dd, J = 1.2, 7.6 Hz, 1H), 7.28 (dd, J = 1.6, 10.8 Hz, 1H), 7.47 (dd, J = 6.8, 8.0 Hz, 1H). |
| 47 | *[structure]* Prepared by the procedure of Example 1 | 438 | $^1$H NMR (400 MHz, DMSO-d$_6$): δ 3.27-3.34 (m, 4H), 3.45 (s, 3H), 3.51-3.53 (m, 4H), 3.81 (s, 3H), 6.78 (d, J = 8.4 Hz, 1H), 7.02-7.08 (m, 2H), 7.18 (dd, J = 1.6, 8.4 Hz, 1H), 7.45 (dd, J = 1.6, 10.8 Hz, 1H), 7.80 (dd, J = 7.2, 8.0 Hz, 1H), 9.41 (br, 1H). |
| 48 | *[structure]* Prepared by the procedure of Example 1 | 434 | $^1$H NMR (400 MHz, CD$_3$OD): δ 1.84-1.94 (m, 2H), 2.20-2.23 (m, 2H), 3.00-3.07 (m, 2H), 3.38-3.42 (m, 5H), 3.72 (s, 3H), 4.22-4.27 (m, 1H), 6.61 (d, J = 8.8 Hz, 1H), 6.79-6.83 (m, 2H), 7.39 (d, J = 8.0 Hz, 2H), 7.51 (d, J = 8.0 Hz, 2H). |

TABLE 3-continued

| Chemical Synthesis Example | Structure (prepared by procedure of cited Example) | MS (ESI) m/z | NMR spectrum data |
|---|---|---|---|
| 49 | Prepared by the procedure of Example 1 | 449 | ¹H NMR (400 MHz, CD₃OD): δ 1.82-1.87 (m, 2H), 2.04-2.07 (m, 2H), 3.06-3.12 (m, 2H), 3.25 (s, 6H), 3.28-3.39 (m, 1H), 3.49 (s, 3H), 3.81-3.84 (m, 2H), 7.37 (d, J = 8.0 Hz, 1H), 7.56 (d, J = 9.6 Hz, 1H), 7.42 (t, J = 6.8 Hz, 1H), 8.31 (s, 2H). |
| 50 | Prepared by the procedure of Example 1 | 462 | ¹H NMR (400 MHz, CD₃OD): δ 1.93-1.97 (m, 2H), 2.17-2.20 (m, 2H), 3.03 (s, 3H), 3.20-3.26 (m, 2H), 3.47-3.53 (m, 1H), 3.62 (s, 3H), 3.98-4.02 (m, 2H), 7.32 (d, J = 8.0 Hz, 1H), 7.60 (d, J = 10.0 Hz, 1H), 7.67 (t, J = 6.4 Hz, 1H), 8.32 (s, 2H), 8.83 (s, 1H). |
| 51 | Prepared by the procedure of Example 1 | 434 | ¹H NMR (400 MHz, CD₃OD): δ 1.89-1.91 (m, 1H), 2.26-2.28 (m, 1H), 2.91-2.93 (m, 1H), 3.12-3.15 (m, 1H), 3.30-3.32 (m, 1H), 3.42-3.55 (m, 5H), 3.70-3.72 (m, 2H) 3.84 (s, 3H), 6.84 (d, J = 8.4 Hz, 2H), 7.03 (d, J = 8.4 Hz, 2H), 7.29 (d, J = 8.0 Hz, 1H), 7.39 (d, J = 10.0 Hz, 1H), 7.64 (t, J = 7.2 Hz, 1H). |
| 52 | Prepared by the procedure of Example 1 | 434 | ¹H NMR (400 MHz, CD₃OD): δ 1.86-1.91 (m, 1H), 2.22-2.28 (m, 1H), 2.97-2.91 (m, 1H), 3.10-3.13 (m, 1H), 3.29-3.32 (m, 1H), 3.40-3.51 (m, 5H), 3.67-3.69 (m, 2H) 3.82 (s, 3H), 6.84 (d, J = 8.0 Hz, 2H), 7.02 (d, J = 8.4 Hz, 2H), 7.27 (d, J = 8.0 Hz, 1H), 7.35 (d, J = 10.4 Hz, 1H), 7.64 (t, J = 7.2 Hz, 1H). |

TABLE 3-continued

| Chemical Synthesis Example | Structure (prepared by procedure of cited Example) | MS (ESI) m/z | NMR spectrum data |
|---|---|---|---|
| 53 | Prepared by the procedure of Example 1 | 434 | ¹H NMR (400 MHz, CD₃OD): δ 2.03-2.06 (m, 2H), 2.32-2.35 (m, 2H), 3.14-3.21 (m, 2H), 3.51-3.56 (m, 5H), 3.78 (s, 3H), 4.37-4.39 (m, 1H), 6.84 (d, J = 7.2 Hz, 2H), 7.02 (d, J = 8.0 Hz, 2H), 7.27 (d, J = 8.0 Hz, 1H), 7.38 (d, J = 10.4 Hz, 1H), 7.62 (t, J = 7.2 Hz, 1H). |
| 54 | Prepared by the procedure of Example 1 | 448 | ¹H NMR (400 MHz, CD₃OD): δ 1.66-1.71 (m, 1H), 2.11-2.16 (m, 1H), 2.77-2.81 (m, 1H), 2.93-2.97 (m, 4H), 3.16-3.20 (m, 1H), 3.30-3.38 (m, 2H), 3.43-3.50 (m, 5H), 3.69 (s, 3H), 6.75 (d, J = 8.4 Hz, 2H), 6.95 (d, J = 8.4 Hz, 2H), 7.16 (d, J = 8.4 Hz, 1H), 7.28 (d, J = 10.8 Hz, 1H), 7.50 (dd, J = 6.8, 8.0 Hz, 1H). |
| 55 | Prepared by the procedure of Example 1 | 448 | ¹H NMR (400 MHz, CD₃OD): δ 2.03-2.13 (m, 4H), 2.84 (s, 3H), 3.01-3.05 (m, 2H), 3.39-3.43 (m, 2H), 3.48 (s, 3H), 3.67 (s, 3H), 3.87-3.92 (m, 1H), 6.74 (d, J = 8.8 Hz, 2H), 6.95 (d, J = 8.8 Hz, 2H), 7.13 (dd, J = 1.2, 8.0 Hz, 1H), 7.21 (dd, J = 1.6, 10.4 Hz, 1H), 7.45 (dd, J = 6.8, 7.6 Hz, 1H). |
| 56 | Prepared by the procedure of Example 1 | 448 | ¹H NMR (400 MHz, CD₃OD): δ 1.77-1.80 (m, 1H), 2.22-2.26 (m, 1H), 2.90-2.92 (m, 1H), 3.03-3.07 (m, 4H), 3.27-3.30 (m, 1H), 3.39-3.41 (m, 2H), 3.44-3.46 (m, 5H), 3.77 (s, 3H), 6.86 (d, J = 8.4 Hz, 2H), 7.06 (d, J = 8.0 Hz, 2H), 7.29 (d, J = 8.4 Hz, 1H), 7.36 (d, J = 8.4 Hz, 1H), 7.58 (dd, J = 6.8, 7.6 Hz, 1H). |

TABLE 3-continued

| Chemical Synthesis Example | Structure (prepared by procedure of cited Example) | MS (ESI) m/z | NMR spectrum data |
|---|---|---|---|
| 57 | Prepared by the procedure of Example 1 | 448 | ¹H NMR (400 MHz, CD₃OD): δ 1.77-1.85 (m, 2H), 2.03-2.06 (m, 2H), 3.03-3.09 (m, 2H), 3.18 (s, 6H), 3.31-3.38 (m, 1H), 3.48 (s, 3H), 3.78-3.81 (m, 2H), 7.03 (d, J = 9.2 Hz, 1H), 7.28 (d, J = 7.6 Hz, 1H), 7.46 (d, J = 10.0 Hz, 1H), 7.59-7.63 (m, 2H), 7.71 (s, 1H). |
| 58 | Prepared by the procedure of Example 1 | 449 | ¹H NMR (400 MHz, CD₃OD): δ 1.83-1.88 (m, 2H), 2.21-2.24 (m, 2H), 2.77 (s, 3H), 3.06-3.14 (m, 2H), 3.31-3.32 (m, 1H), 3.58 (s, 3H), 3.87-3.91 (m, 5H), 6.83 (d, J = 11.2 Hz, 1H), 7.22 (dd, J = 2.0, 10.8 Hz, 1H), 7.42 (dd, J = 2.0, 14.4 Hz, 1H), 7.59-7.65 (m, 2H), 7.84 (d, J = 3.2 Hz, 1H). |
| 59 | Prepared by the procedure of Example 1 | 447 | ¹H NMR (400 MHz, CD₃OD): δ 1.88-1.89 (m, 2H), 2.14-2.19 (m, 2H), 3.13-3.19 (m, 2H), 3.28 (s, 6H), 3.41-3.46 (m, 1H), 3.60 (s, 3H), 3.87-3.91 (m, 2H), 7.24 (d, J = 10.8 Hz, 1H), 7.39-7.44 (m, 3H), 7.59-7.67 (m, 3H). |
| 60 | Prepared by the procedure of Example 1 | 474 | ¹H NMR (400 MHz, CD₃OD): δ 1.91-1.97 (m, 2H), 2.16-2.20 (m, 6H), 3.14-3.20 (m, 2H), 3.47-3.49 (m, 1H), 3.60-3.63 (m, 7H), 3.89-3.92 (m, 2H), 7.31 (d, J = 9.6 Hz, 1H), 7.01 (d, J = 9.6 Hz, 1H), 7.41 (d, J = 8.0 Hz, 1H), 7.58 (d, J = 10.0 Hz, 1H), 7.68-7.75 (m, 2H), 7.79 (s, 1H). |

TABLE 3-continued

| Chemical Synthesis Example | Structure (prepared by procedure of cited Example) | MS (ESI) m/z | NMR spectrum data |
|---|---|---|---|
| 61 | Prepared by the procedure of Example 1 | 435 | ¹H NMR (400 MHz, CD₃OD): δ 2.27-2.30 (m, 2H), 3.44-.347 (m, 2H), 3.60-3.64 (m, 5H), 3.70-3.73 (m, 2H), 3.91-3.94 (m, 5H), 6.83 (d, J = 8.4 Hz, 1H), 7.24 (dd, J = 1.6, 8.0 Hz, 1H), 7.43 (dd, J = 1.2, 10.4 Hz, 1H), 7.59-7.66 (m, 2H), 7.84 (d, J = 2.4 Hz, 1H). |
| 62 | Prepared by the procedure of Example 1 | 417 | ¹H NMR (400 MHz, CD₃OD): δ 2.27-2.31 (m, 2H), 3.44-.347 (m, 2H), 3.60-3.64 (m, 5H), 3.70-3.73 (m, 2H), 3.91-3.94 (m, 5H), 6.81 (d, J = 8.4 Hz, 1H), 7.53 (d, J = 8.4 Hz, 2H), 7.58 (dd, J = 2.4, 8.8 Hz, 1H), 7.64 (d, J = 8.8 Hz, 2H), 7.84 (d, J = 1.2 Hz, 1H). |
| 63 | Prepared by the procedure of Example 1 | 448 | ¹H NMR (400 MHz, CD₃OD): δ 2.31-2.33 (m, 2H), 3.27 (s, 6H) 3.44-.347 (m, 2H), 3.60-3.67 (m, 5H), 3.73-3.76 (m, 2H), 3.96-3.99 (m, 2H), 6.81 (d, J = 8.4 Hz, 1H), 7.53 (d, J = 8.4 Hz, 1H), 7.58 (dd, J = 2.4, 8.8 Hz, 1H), 7.64 (d, J = 8.8 Hz, 2H), 7.84 (d, J = 1.2 Hz, 1H). |
| 64 | Prepared by the procedure of Example 1 | 406 | ¹H NMR (400 MHz, CD₃OD): δ 3.39 (s, 3H), 3.67 (s, 3H), 4.09-4.10 (m, 1H), 4.17-4.21 (m, 2H), 4.55-4.59 (m, 2H), 6.74 (d, J = 8.8 Hz, 2H), 6.96 (d, J = 8.8 Hz, 2H), 7.10 (dd, J = 1.6, 8.4 Hz, 1H), 7.23 (dd, J = 1.6, 10.8 Hz, 1H), 7.45 (dd, J = 6.8, 8.0 Hz, 1H). |

TABLE 3-continued

| Chemical Synthesis Example | Structure (prepared by procedure of cited Example) | MS (ESI) m/z | NMR spectrum data |
|---|---|---|---|
| 65 | Prepared by the procedure of Example 1 | 472 | ¹H NMR (400 MHz, CD₃OD): δ 1.85-1.98 (m, 2H), 2.23-2.27 (m, 2H), 2.78 (s, 3H), 3.38-3.40 (m, 1H), 3.62 (s, 3H), 3.90-3.95 (m, 2H), 4.41 (s, 3H), 7.26 (d, J = 10.8 Hz, 1H), 7.40 (d, J = 13.6 Hz, 1H), 7.49-7.57 (m, 2H), 7.65 (dd, J = 6.8, 11.6 Hz, 1H), 7.73 (s, 1H), 8.66 (s, 1H). |
| 66 | Prepared by the procedure of Example 1 | 458 | ¹H NMR (400 MHz, CD₃OD): δ 2.19-2.20 (m, 2H), 3.33-3.36 (m, 2H), 3.50-3.53 (m, 5H), 3.60-3.63 (m, 2H), 3.83-3.85 (m, 2H), 4.42 (s, 3H), 7.13 (d, J = 7.6 Hz, 1H), 7.28 (d, J = 10.4 Hz, 1H), 7.34 (d, J = 9.2 Hz, 1H), 7.40 (t, J = 7.2 Hz, 1H), 7.52 (d, J = 8.8 Hz, 1H), 7.58 (s, 1H), 8.48 (s, 1H). |
| 67 | Prepared by the procedure of Example 1 | 430 | ¹H NMR (400 MHz, CD₃OD): δ 2.33-2.35 (m, 2H), 3.27 (s, 6H), 3.46-3.49 (m, 2H), 3.62-3.66 (m, 5H), 3.75-3.78 (m, 2H), 3.98-4.02 (m, 2H), 6.73 (d, J = 9.2 Hz, 1H), 7.67-7.72 (m, 5H), 7.80 (s, 1H). |
| 68 | Prepared by the procedure of Example 1 | 490 | ¹H NMR (400 MHz, CD₃OD): δ 1.89-1.97 (m, 2H), 2.15-2.18 (m, 2H), 3.15-3.21 (m, 2H), 3.43-3.49 (m, 1H), 3.61 (s, 3H), 3.69-3.71 (m, 4H), 3.86-3.94 (m, 6H), 7.31 (d, J = 9.6 Hz, 1H), 7.41 (d, J = 8.0 Hz, 1H), 7.59 (d, J = 10.0 Hz, 1H), 7.72-7.80 (m, 2H), 7.91 (s, 1H). |

TABLE 3-continued

| Chemical Synthesis Example | Structure (prepared by procedure of cited Example) | MS (ESI) m/z | NMR spectrum data |
|---|---|---|---|
| 69 | Prepared by the procedure of Example 1 | 420 | ¹H NMR (400 MHz, CD₃OD): δ 2.99-3.06 (m, 1H), 3.30-3.32 (m, 2H), 3.49 (s, 3H), 3.78 (s, 3H), 4.10-4.15 (m, 2H), 4.46-4.52 (m, 2H), 6.83 (d, J = 8.4 Hz, 2H), 7.01 (d, J = 8.8 Hz, 2H), 7.19 (dd, J = 2.0, 10.8 Hz, 1H), 7.33 (dd, J = 2.0, 14.4 Hz, 1H), 7.45 (dd, J = 8.8, 10.8 Hz, 1H). |
| 70 | Prepared by the procedure of Example 1 | 434 | ¹H NMR (400 MHz, CD₃OD): δ 2.78 (s, 3H), 3.07-3.10 (m, 1H), 3.37-3.39 (m, 2H), 3.48 (s, 3H), 3.78 (s, 3H), 4.12-4.15 (m, 2H), 4.47-4.52 (m, 2H), 6.84 (d, J = 8.8 Hz, 2H), 7.01 (d, J = 8.8 Hz, 2H), 7.20 (d, J = 8.0 Hz, 1H), 7.33 (d, J = 10.4 Hz, 1H), 7.45 (t, J = 7.2 Hz, 1H). |
| 71 | Prepared by the procedure of Example 1 | 486 | ¹H NMR (400 MHz, CD₃OD): δ 1.67-1.73 (m, 2H), 2.02-2.06 (m, 2H), 2.33 (s, 6H), 2.41-2.45 (m, 1H), 2.95-3.03 (m, 2H), 3.59 (s, 3H), 3.79-3.84 (m, 2H), 4.18 (s, 3H), 7.10 (dd, J = 2.0, 12.0 Hz, 1H), 7.23 (dd, J = 1.6, 10.8 Hz, 1H), 7.37 (dd, J = 2.0, 14.4 Hz, 1H), 7.46-7.56 (m, 3H), 8.11 (s, 1H). |
| 72 | Prepared by the procedure of Example 1 | 486 | ¹H NMR (400 MHz, DMSO-d₆): δ 1.50-1.63 (m, 2H), 1.85-1.89 (m, 2H), 2.18 (s, 6H), 2.21-2.27 (m, 1H), 2.85-2.92 (m, 2H), 3.45 (s, 3H), 3.67-3.71 (m, 2H), 4.00 (s, 3H), 7.09-7.17 (m, 2H), 7.39 (dd, J = 1.6, 14.4 Hz, 1H), 7.51-7.54 (m, 2H), 7.69 (t, J = 9.2 Hz, 1H), 7.97 (s, 1H). |

TABLE 3-continued

| Chemical Synthesis Example | Structure (prepared by procedure of cited Example) | MS (ESI) m/z | NMR spectrum data |
|---|---|---|---|
| 73 | Prepared by the procedure of Example 18 | 443 | ¹H NMR (400 MHz, CD₃OD): δ 1.85-1.91 (m, 2H), 2.11-2.16 (m, 2H), 3.06-3.14 (m, 2H), 3.36-3.40 (m, 1H), 3.57 (s, 3H), 3.81-3.85 (m, 2H), 6.85 (d, J = 8.4 Hz, 2H), 7.22 (d, J = 3.0 Hz, 1H), 7.24 (s, 1H), 7.33-7.48 (m, 4H). |
| 74 | Prepared by the procedure of Example 18 | 456 | ¹H NMR (400 MHz, CD₃OD): δ 1.53-1.56 (m, 2H), 1.88-1.91 (m, 2H), 2.87-2.95 (m, 3H), 3.49 (s, 3H), 3.62 (d, J = 13.6 Hz, 2H), 3.69 (s, 3H), 6.26 (s, 1H), 6.81 (d, J = 4.0 Hz, 1H), 7.04-7.35 (m, 6H). |
| 75 | Prepared by the procedure of Example 18 | 442 | ¹H NMR (400 MHz, CD₃OD): δ 1.88-1.94 (m, 2H), 2.13-2.16 (m, 2H), 3.05-3.16 (m, 2H), 3.33-3.42 (m, 1H), 3.60 (s, 3H), 3.84-3.86 (m, 2H), 6.74-6.77 (m, 1H), 7.20-7.50 (m, 7H). |
| 76 | Prepared by the procedure of Example 1 | 457 | ¹H NMR (400 MHz, CD₃OD): δ 1.51-1.54 (m, 2H), 1.88-1.91 (m, 2H), 2.84-2.97 (m, 3H), 3.49 (s, 3H), 3.62-3.65 (m, 5H), 6.31 (d, J = 2.8 Hz, 1H), 6.61 (d, J = 8.0 Hz, 1H), 7.06 (d, J = 3.2 Hz, 1H), 7.13-7.18 (m, 3H), 7.27 (d, J = 10.8 Hz, 1H), 7.33-7.37 (m, 2H). |

TABLE 3-continued

| Chemical Synthesis Example | Structure (prepared by procedure of cited Example) | MS (ESI) m/z | NMR spectrum data |
|---|---|---|---|
| 77 | Prepared by the procedure of Example 1 | 444 | ¹H NMR (400 MHz, CD₃OD): δ 1.65-1.68 (m, 2H), 2.01-2.04 (m, 2H), 2.98-3.12 (m, 3H), 3.63 (s, 3H), 3.78-3.82 (m, 2H), 6.94 (d, J = 8.4 Hz, 1H), 7.24 (d, J = 8.0 Hz, 1H), 7.43-7.45 (m, 2H), 7.50 (t, J = 7.2 Hz, 1H), 7.72 (d, J = 8.4 Hz, 1H), 8.06 (s, 1H). |
| 78 | Prepared by the procedure of Example 1 | 452 | ¹H NMR (300 MHz, CD₃OD): δ 1.84-1.91 (m, 1H), 2.01-2.06 (m, 1H), 3.00-3.08 (m, 2H), 3.16-3.21 (m, 1H), 3.58 (s, 3H), 3.75-3.82 (m, 4H), 3.93-4.01 (m, 1H), 4.70-4.82 (m, 1H), 6.86 (d, J = 9.0 Hz, 2H), 7.06 (d, J = 8.7 Hz, 2H), 7.24 (dd, J = 0.9, 8.1 Hz, 1H), 7.34 (dd, J = 1.5, 10.8 Hz, 1H), 7.54-7.58 (m, 1H). |
| 79 | Prepared by the procedure of Example 1 | 452 | ¹H NMR (400 MHz, CD₃OD): δ 1.87-1.91 (m, 1H), 2.03-2.07 (m, 1H), 3.02-3.08 (m, 2H), 3.19-3.29 (m, 1H), 3.59 (s, 3H), 3.77-3.83 (m, 4H), 3.95-4.01 (m, 1H), 4.73-4.85 (m, 1H), 6.87 (d, J = 8.8 Hz, 2H), 7.07 (d, J = 8.8 Hz, 2H), 7.26 (dd, J = 1.2, 8.4 Hz, 1H), 7.36 (dd, J = 1.2, 10.8 Hz, 1H), 7.56 (t, J = 6.8 Hz, 1H). |
| 80 | Prepared by the procedure of Example 1 | 486 | ¹H NMR (400 MHz, CD₃OD): δ 1.71-1.77 (m, 2H), 2.05-2.08 (m, 2H), 2.38 (s, 6H), 2.45-2.48 (m, 1H), 2.98-3.05 (m, 2H), 3.61 (s, 3H), 3.83-3.86 (m, 2H), 4.20 (s, 3H), 6.93 (dd, J = 12., 8.8 Hz, 1H), 7.27 (dd, J = 1.2, 7.6 Hz, 1H), 7.36-7.41 (m, 2H), 7.49-7.53 (m, 1H), 7.66 (d, J = 8.8 Hz, 1H), 8.18 (s, 1H). |

TABLE 3-continued

| Chemical Synthesis Example | Structure (prepared by procedure of cited Example) | MS (ESI) m/z | NMR spectrum data |
|---|---|---|---|
| 81 | Prepared by the procedure of Example 1 | 477 | ¹H NMR (400 MHz, CD₃OD): δ 2.03-2.06 (m, 2H), 2.25-2.27 (m, 2H), 2.98 (s, 6H), 3.14-3.20 (m, 2H), 3.36 (s, 6H), 3.56-3.60 (m, 1H), 3.62 (s, 3H), 4.01-4.04 (m, 2H), 7.49 (d, J = 4.4 Hz, 1H), 7.67 (d, J = 10.0 Hz, 1H), 7.75-7.78 (m, 1H), 8.43 (s, 2H). |
| 82 | Prepared by the procedure of Example 1 | 447 | ¹H NMR (400 MHz, CD₃OD): δ 1.56-1.62 (m, 2H), 1.91-1.94 (m, 2H), 2.25 (s, 6H), 2.31-2.37 (m, 1H), 2.41 (s, 3H), 2.87-2.93 (m, 2H), 3.47 (s, 3H), 3.72-3.76 (m, 2H), 7.10 (dd, J = 1.2, 8.0 Hz, 1H), 7.15 (d, J = 8.0 Hz, 1H), 7.28-7.31 (m, 1H), 7.49-7.52 (m, 2H), 7.80 (d, J = 2.0 Hz, 1H). |
| 83 | Prepared by the procedure of Example 1 | 462 | ¹H NMR (400 MHz, CD₃OD): δ 1.92-2.04 (m, 2H), 2.24-2.26 (m, 2H), 2.79 (s, 3H), 3.14-3.20 (m, 2H), 3.30 (s, 6H), 3.37-3.40 (m, 1H), 3.61 (s, 3H), 3.94-3.98 (m, 2H), 7.16 (d, J = 9.6 Hz, 1H), 7.42 (d, J = 8.0 Hz, 1H), 7.61 (d, J = 10.0 Hz, 1H), 7.71-7.76 (m, 2H), 7.84 (d, J = 1.2 Hz, 1H). |
| 84 | Prepared by the procedure of Example 1 | 472 | ¹H NMR (400 MHz, CDCl₃): δ 1.61-1.69 (m, 2H), 1.98-2.01 (m, 2H), 2.32 (s, 6H), 2.32-2.33 (m, 1H), 2.88-2.94 (m, 2H), 3.53 (s, 3H), 3.65-3.69 (m, 2H), 6.73 (dd, J = 1.2, 8.8 Hz, 1H), 7.00 (dd, J = 1.2, 8.0 Hz, 1H), 7.19-7.30 (m, 2H), 7.37 (s, 1H), 7.52 (d, J = 8.4 Hz, 1H), 7.90 (s, 1H), 10.65 (br, 1H). |

TABLE 3-continued

| Chemical Synthesis Example | Structure (prepared by procedure of cited Example) | MS (ESI) m/z | NMR spectrum data |
|---|---|---|---|
| 85 | Prepared by the procedure of Example 1 | 455 | ¹H NMR (400 MHz, CD₃OD): δ 1.88-1.92 (m, 2H), 2.15-2.18 (m, 2H), 3.12-3.18 (m, 2H), 3.40-3.46 (m, 1H), 3.85-3.88 (m, 5H), 6.81 (d, J = 8.4 Hz, 1H), 6.98-7.05 (m, 2H), 7.25 (dd, J = 1.2, 8.4 Hz, 1H), 7.42 (d, J = 11.2 Hz, 1H), 7.61 (t, J = 7.2 Hz, 1H). |
| 86 | Prepared by the procedure of Example 1 | 455 | ¹H NMR (400 MHz, CD₃OD): δ 1.88-1.92 (m, 2H), 2.14-2.17 (m, 2H), 3.11-3.17 (m, 2H), 3.42-3.47 (m, 1H), 3.59 (s, 3H), 3.85-3.88 (m, 2H), 6.81 (d, J = 8.4 Hz, 1H), 6.98-7.05 (m, 2H), 7.25 (dd, J = 1.2, 8.0 Hz, 1H), 7.42 (d, J = 10.4 Hz, 1H), 7.60 (dd, J = 0.8, 7.6 Hz, 1H). |
| 87 | Prepared by the procedure of Example 1 | 472 | ¹H NMR (400 MHz, DMSO-d₆): δ ppm 1.79 (br. s., 2 H) 2.11 (br. s., 2 H) 2.97 (br. s., 2 H) 3.10-3.31 (m, 1 H) 3.46 (br. s., 3 H) 3.74 (d, J = 18.19 Hz, 2 H) 4.03 (br. s., 3 H) 7.12 (d, J = 13.39 Hz, 1 H) 7.40-7.61 (m, 4 H) 7.71 (br. s., 1 H) 7.87-8.07 (m, 1 H) 9.15 (br. s., 2 H). |
| 88 | Prepared by the procedure of Example 1 | 444 | ¹H NMR (400 MHz, Methanol-d₄): δ ppm 1.84 (d, J = 13.39 Hz, 2 H) 2.11 (d, J = 13.14 Hz, 2 H) 3.05-3.17 (m, 2 H) 3.35-3.40 (m, 1 H) 3.59 (s, 3 H) 3.83 (d, J = 14.40 Hz, 2 H) 7.17 (d, J = 8.08 Hz, 2 H) 7.41 (d, J = 10.61 Hz, 1 H) 7.44-7.52 (m, 2 H) 7.57 (s, 1 H) 7.98 (s, 1 H) 8.54 (br. s., 1 H). |

TABLE 3-continued

| Chemical Synthesis Example | Structure (prepared by procedure of cited Example) | MS (ESI) m/z | NMR spectrum data |
|---|---|---|---|
| 89 | Prepared by the procedure of Example 1 | 419 | ¹H NMR (400 MHz, Methanol-d₄): δ ppm 1.74-1.96 (m, 2 H) 2.11 (d, J = 12.13 Hz, 2 H) 3.08 (q, J = 11.54 Hz, 2 H) 3.38 (br. s., 1 H) 3.57 (br. s., 3 H) 3.71-3.93 (m, 2 H) 6.64 (d, J = 8.08 Hz, 2 H) 6.86 (d, J = 8.08 Hz, 2 H) 7.07-7.17 (m, 1 H) 7.18-7.30 (m, 1 H) 7.31-7.43 (m, 1 H). |
| 90 | Prepared by the procedure of Example 1 | 433 | ¹H NMR (400 MHz, Methanol-d₄): δ ppm 1.72-1.93 (m, 2 H) 2.09 (d, J = 11.62 Hz, 2 H) 2.75 (s, 3 H) 2.99-3.14 (m, 2 H) 3.36-3.43 (m, 1 H) 3.56 (s, 3 H) 3.78 (d, J = 12.38 Hz, 2 H) 6.54 (d, J = 7.83 Hz, 2 H) 6.89 (d, J = 7.83 Hz, 2 H) 7.27 (d, J = 8.34 Hz, 1 H) 7.32-7.43 (m, 1 H) 7.48-7.62 (m, 1 H). |
| 91 | Prepared by the procedure of Example 1 | 451 | ¹H NMR (400 MHz, Methanol-d₄): δ ppm 1.86 (d, J = 11.87 Hz, 2 H) 2.12 (d, J = 11.12 Hz, 2 H) 2.96 (s, 3 H) 3.11 (t, J = 12.25 Hz, 2 H) 3.40 (br. s., 1 H) 3.57 (s, 3 H) 3.84 (d, J = 12.38 Hz, 2 H) 6.90 (d, J = 8.59 Hz, 1 H) 7.05 (t, J = 8.46 Hz, 1 H) 7.12 (d, J = 12.38 Hz, 1 H) 7.26 (d, J = 8.34 Hz, 1 H) 7.40 (d, J = 10.61 Hz, 1 H) 7.60 (t, J = 7.20 Hz, 1 H). |
| 92 | Prepared by the procedure of Example 1 | 463 | ¹H NMR (400 MHz, Chloroform-d): δ ppm 1.71 (m, J = 11.37 Hz, 2 H) 1.74 (br. s., 1 H) 2.04 (d, J = 11.87 Hz, 2 H) 2.38 (br. s., 6 H) 2.96 (t, J = 12.76 Hz, 2 H) 3.55 (s, 3 H) 3.71 (d, J = 12.88 Hz, 2 H) 3.91 (s, 3 H) 6.73 (d, J = 8.59 Hz, 1 H) 7.12 (d, J = 7.83 Hz, 1 H) 7.34 (d, J = 10.11 Hz, 1 H) 7.43 (t, J = 7.07 Hz, 1 H) 7.53 (d, J = 8.34 Hz, 1 H) 7.81 (br. s., 1 H). |

TABLE 3-continued

| Chemical Synthesis Example | Structure (prepared by procedure of cited Example) | MS (ESI) m/z | NMR spectrum data |
|---|---|---|---|
| 93 | Prepared by the procedure of Example 1 | 467 | ¹H NMR (400 MHz, DMSO-d₆): δ ppm 1.32 (td, J = 7.01, 1.39 Hz, 3 H) 1.58 (d, J = 11.62 Hz, 2 H) 1.92 (d, J = 11.62 Hz, 2 H) 2.80 (s, 3 H) 2.91-3.03 (m, 2 H) 3.08 (br. s., 1 H) 3.69 (d, J = 10.36 Hz, 2 H) 4.29-4.40 (m, 2 H) 6.86 (s, 1 H) 6.89 (d, J = 8.08 Hz, 1 H) 7.21 (d, J = 8.08 Hz, 1 H) 7.56 (d, J = 1.77 Hz, 1 H) 7.81-7.86 (m, 1 H) 8.33 (s, 3 H). |
| 94 | Prepared by the procedure of Example 1 | 449 | ¹H NMR (400 MHz, DMSO-d₆): δ ppm 1.28 (td, J = 7.01, 2.40 Hz, 3 H) 1.58 (br. s., 2 H) 1.89 (br. s., 2 H) 2.92-3.02 (m, 2 H) 3.07 (br. s., 1 H) 3.43 (s, 3 H) 3.68 (d, J = 13.39 Hz, 2 H) 4.21-4.29 (m, 2 H) 6.73 (d, J = 3.79 Hz, 1 H) 6.80 (s, 1 H) 6.93 (d, J = 7.83 Hz, 1 H) 7.20 (d, J = 8.59 Hz, 1 H) 7.54 (d, J = 8.08 Hz, 1 H) 7.80-7.85 (m, 1 H) 8.31 (s, 3 H). |
| 95 | Prepared by the procedure of Example 1 | 448 | ¹H NMR (400 MHz, DMSO-d₆): δ ppm 1.31 (t, J = 6.69 Hz, 3 H) 1.73 (d, J = 9.09 Hz, 2 H) 2.00 (d, J = 12.13 Hz, 2 H) 2.99 (t, J = 12.51 Hz, 2 H) 3.28 (br. s., 1 H) 3.43 (s, 3 H) 3.71 (d, J = 12.38 Hz, 2 H) 3.95-4.06 (m, 2 H) 6.83 (d, J = 8.08 Hz, 2 H) 7.01 (d, J = 8.59 Hz, 2 H) 7.18 (d, J = 8.59 Hz, 1 H) 7.41 (d, J = 10.86 Hz, 1 H) 7.61 (m, 1H) 7.79 (t, J = 7.83 Hz, 1 H) 8.07 (br. s., 3 H). |
| 96 | Prepared by the procedure of Example 1 | 464 | ¹H NMR (400 MHz, DMSO-d₆): δ ppm 1.74 (d, J = 10.36 Hz, 2 H) 2.00 (d, J = 11.62 Hz, 2H) 2.99 (t, J = 12.25 Hz, 2 H) 3.43 (s, 3H) 3.64 (br. s., 2 H) 3.71 (d, J = 11.87 Hz, 2 H) 4.07 (br. s., 2 H) 6.85 (d, J = 8.34 Hz, 2 H) 7.01 (d, J = 8.34 Hz, 2 H) 7.18 (d, J = 8.08 Hz, 1 H) 7.41 (d, J = 10.36 Hz, 1 H) 7.58-7.67 (m, 1 H) 7.79 (t, J = 7.45 Hz, 1 H) 8.14 (br. s., 3 H). |

TABLE 3-continued

| Chemical Synthesis Example | Structure (prepared by procedure of cited Example) | MS (ESI) m/z | NMR spectrum data |
|---|---|---|---|
| 97 | Prepared by the procedure of Example 1 | 446 | ¹H NMR (400 MHz, Methanol-d₄): δ ppm 1.87 (d, J = 11.12 Hz, 2 H) 2.13 (d, J = 12.13 Hz, 2 H) 3.04-3.21 (m, 2 H) 3.38 (d, J = 10.61 Hz, 1 H) 3.57 (s, 3 H) 3.77-3.88 (m, 4 H) 4.02 (br. s., 2 H) 6.86 (d, J = 7.83 Hz, 2 H) 7.04 (d, J = 8.34 Hz, 2 H) 7.47-7.53 (m, 2 H) 7.57 (d, 7.58 Hz, 2 H). |
| 98 | Prepared by the procedure of Example 1 | 478 | ¹H NMR (400 MHz, DMSO-d₆) δ ppm: 1.74 (d, J = 11.87 Hz, 2 H) 2.00 (d, J = 12.38 Hz, 2 H) 2.99 (t, J = 12.25 Hz, 2 H) 3.28 (br. s., 1 H) 3.43 (s, 3 H) 3.44-3.54 (m, 2 H) 3.70 (m, 5 H) 3.90-4.05 (m, 2 H) 6.85 (d, J = 8.34 Hz, 2 H) 7.01 (d, J = 7.83 Hz, 2 H) 7.18 (d, J = 8.08 Hz, 1 H) 7.42 (d, J = 10.61 Hz, 1 H) 7.79 (t, J = 7.20 Hz, 1 H) 8.11 (br. s., 3 H). |
| 99 | Prepared by the procedure of Example 1 | 448 | ¹H NMR (400 MHz, DMSO-d₆): δ ppm 1.73 (d, J = 11.37 Hz, 2 H) 2.00 (d, J = 12.63 Hz, 2 H) 2.64-2.76 (m, 2 H) 3.00 (t, J = 12.13 Hz, 2 H) 3.29 (br. s., 1 H) 3.43 (br. s., 3 H) 3.48 (d, J = 9.85 Hz, 2 H) 3.69-3.77 (m, 2 H) 7.00 (d, J = 7.33 Hz, 2 H) 7.13 (d, J = 7.83 Hz, 2 H) 7.18 (d, J = 8.34 Hz, 1 H) 7.34-7.42 (m, 1 H) 7.75-7.80 (m, 1 H) 8.06 (br. s., 3 H). |
| 100 | Prepared by the procedure of Example 1 | 434 | ¹H NMR (400 MHz, DMSO-d₆): δ ppm 1.73 (d, J = 12.13 Hz, 2 H) 1.94-2.03 (m, 2 H) 3.00 (br. s., 2 H) 3.29 (br. s., 1 H) 3.44 (s, 3 H) 3.48 (d, J = 9.60 Hz, 2 H) 3.70 (br. s., 2 H) 7.06 (d, J = 7.33 Hz, 2 H) 7.16-7.25 (m, 3 H) 7.41 (d, J = 10.86 Hz, 1 H) 7.75-7.82 (m, 1 H) 8.05 (br. s., 3 H). |
| 101 | Prepared by the procedure of Example 1 | 422 | ¹H NMR (400 MHz, Methanol-d₄): δ ppm 1.78-1.94 (m, 2 H) 2.13 (d, J = 11.87 Hz, 2 H) 3.10 (t, J = 12.51 Hz, 2 H) 3.39 (d, J = 12.13 Hz, 1 H) 3.57 (s, 3 H) 3.73-3.93 (m, 2 H) 6.99-7.09 (m, 2 H) 7.12-7.25 (m, 3 H) 7.37 (d, J = 10.36 Hz, 1 H) 7.57 (t, J = 6.95 Hz, 1 H). |

TABLE 3-continued

| Chemical Synthesis Example | Structure (prepared by procedure of cited Example) | MS (ESI) m/z | NMR spectrum data |
|---|---|---|---|
| 102 | Prepared by the procedure of Example 1 | 422 | ¹H NMR (400 MHz, Methanol-d$_4$): δ ppm 1.79-1.93 (m, 2 H) 2.13 (d, J = 12.38 Hz, 2 H) 3.11 (t, J = 12.63 Hz, 2 H) 3.39 (d, J = 11.62 Hz, 1 H) 3.57 (s, 3 H) 3.85 (d, J = 13.64 Hz, 2 H) 6.89 (d, J = 7.83 Hz, 1 H) 6.96-7.07 (m, 2 H) 7.23 (d, J = 8.34 Hz, 1 H) 7.25-7.33 (m, 1 H) 7.38 (d, J = 10.36 Hz, 1 H) 7.58 (t, J = 7.20 Hz, 1 H). |
| 103 | Prepared by the procedure of Example 1 | 440 | ¹H NMR (400 MHz, Methanol-d$_4$): δ ppm 1.77-1.95 (m, 2 H) 2.13 (d, J = 11.62 Hz, 2 H) 3.12 (t, J = 12.76 Hz, 2 H) 3.36-3.45 (m, 1 H) 3.55 (s, 3 H) 3.86 (d, J = 13.64 Hz, 2 H) 6.78 (d, J = 6.57 Hz, 2 H) 6.89 (t, J = 9.22 Hz, 1 H) 7.24 (d, J = 8.08 Hz, 1 H) 7.43 (d, J = 10.11 Hz, 1 H) 7.62 (t, J = 7.07 Hz, 1 H). |
| 104 | Prepared by the procedure of Example 1 | 440 | ¹H NMR (400 MHz, Methanol-d$_4$): δ ppm 1.79-1.93 (m, 2 H) 2.12 (d, J = 11.62 Hz, 2 H) 3.11 (t, J = 12.63 Hz, 2 H) 3.33-3.49 (m, 1 H) 3.57 (s, 3 H) 3.85 (d, J = 13.64 Hz, 2 H) 6.87 (br. s., 1 H) 7.11-7.25 (m, 3 H) 7.42 (d, J = 10.36 Hz, 1 H) 7.60 (t, J = 7.20 Hz, 1 H). |
| 105 | Prepared by the procedure of Example 1 | 482 | ¹H NMR (400 MHz, Methanol-d$_4$): δ ppm 1.79-1.92 (m, 2 H) 2.12 (d, J = 11.62 Hz, 2 H) 3.05-3.29 (m, 5 H) 3.40 (br. s., 1 H) 3.58 (s, 3 H) 3.80-3.94 (m, 2 H) 7.16 (d, J = 7.58 Hz, 1 H) 7.36-7.48 (m, 3 H) 7.58 (t, J = 7.20 Hz, 1 H) 7.87 (d, J = 8.08 Hz, 2 H). |

TABLE 3-continued

| Chemical Synthesis Example | Structure (prepared by procedure of cited Example) | MS (ESI) m/z | NMR spectrum data |
|---|---|---|---|
| 106 | Prepared by the procedure of Example 1 | 438 | ¹H NMR (400 MHz, Chloroform-d): δ ppm 1.89 (d, J = 11.12 Hz, 2 H) 2.16 (d, J = 10.86 Hz, 2 H) 3.05 (t, J = 11.87 Hz, 2 H) 3.28 (br. s., 1 H) 3.55 (s, 3 H) 3.71 (d, J = 12.13 Hz, 2 H) 7.04 (d, J = 8.34 Hz, 1 H) 7.10 (d, J = 8.08 Hz, 2 H) 7.27-7.30 (m, 1 H) 7.33-7.44 (m, 2 H) 8.31 (br. s., 1 H). |
| 107 | Prepared by the procedure of Example 1 | 448 | ¹H NMR (400 MHz, Methanol-d₄): δ ppm 1.81-1.94 (m, 2 H) 2.13 (d, J = 12.13 Hz, 2 H) 3.12 (t, J = 12.38 Hz, 2 H) 3.36 (s, 3 H) 3.41 (br. s., 1 H) 3.58 (s, 3 H) 3.84 (d, J = 12.63 Hz, 2 H) 4.45 (s, 2 H) 7.14 (d, J = 7.58 Hz, 2 H) 7.23 (d, J = 7.83 Hz, 1 H) 7.28 (d, J = 7.83 Hz, 2 H) 7.34 (d, J = 10.61 Hz, 1 H) 7.55 (t, J = 7.20 Hz, 1 H). |
| 108 | Prepared by the procedure of Example 13 | 328 | ¹H NMR (400 MHz, DMSO-d₆): δ ppm 1.62-1.78 (m, 2 H) 2.00 (d, J = 11.87 Hz, 2 H) 3.02 (t, J = 12.00 Hz, 2H) 3.32 (s, 3 H) 3.76 (d, J = 12.88 Hz, 2 H) 6.87 (s, 1 H) 7.95 (br. s., 3 H) 8.01-8.08 (m, 1 H) 8.08-8.12 (m, 1 H) 8.16 (d, J = 11.12 Hz, 1 H). |
| 109 | Prepared by the procedure of Example 13 | 368 | ¹HNMR (400 MHz, CD₃OD): δ 0.37-0.39 (m, 2H), 0.60-0.65 (m, 2H), 1.29-1.32 (m, 1H), 1.59-1.64 (m, 2H), 2.10-2.14 (m, 2H), 3.07-3.14 (m, 2H), 3.43-3.47 (m, 1H), 6.81 (d, J = 7.2 Hz, 2H), 4.92-4.95 (m, 2H), 6.66 (s, 1H), 7.84-7.88 (m, 1H), 7.99-8.05 (m, 2H). |
| 110 | Prepared by the procedure of Example 14 | 352 | ¹H NMR (400 MHz, CD₃OD): δ 1.40-1.41 (m, 2H), 1.81-1.84 (m, 2H), 2.75-2.78 (m, 1H), 2.89-2.95 (m, 2H), 3.37 (s, 3H), 3.65-3.68 (m, 2H), 3.77 (s, 1H), 7.66 (t, J = 8.0 Hz, 1H), 7.89 (d, J = 8.0 Hz, 1H), 7.96 (d, J = 8.4 Hz, 1H). |

TABLE 3-continued

| Chemical Synthesis Example | Structure (prepared by procedure of cited Example) | MS (ESI) m/z | NMR spectrum data |
|---|---|---|---|
| 111 | Prepared by the procedure of Example 1 | 442 | $^1$H NMR (400, MHz, DMSO-$d_6$): 1.75-1.83 (m, 2H), 2.06 (d, J = 10.8 Hz, 2H), 2.99 (t, J = 11.6 Hz, 2H), 3.28-3.30 (m, 1H), 3.42 (s, 3H), 3.68-3.74 (m, 5H), 6.85 (d, J = 8.0 Hz, 2H), 7.02-7.08 (m, 3H)), 7.28-7.45 (m, 2H), 8.38-8.44 (m, 2H). |
| 112 | Prepared by the procedure of Example 1 | 429 | $^1$H NMR (400 MHz, CD$_3$OD): 1.09-1.17 (m, 2H), 1.57-1.62 (m, 2H), 2.46-2.56 (m, 3H), 2.96-3.03 (m, 2H), 3.35 (s, 3H), 3.78 (s, 3H), 6.02 (s, 1H), 6.37 (s, 1H), 6.79-6.97 (m, 3H), 7.13-7.27 (m, 2H), 7.42-7.52 (m, 2H). |
| 113 | Prepared by the procedure of Example 1 | 431 | $^1$H NMR (400 MHz, CD$_3$OD): 1.06-1.17 (m, 2H), 1.57-1.62 (m, 2H), 2.49-2.56 (m, 3H), 2.96-3.09 (m, 2H), 3.36 (s, 3H), 3.78 (s, 3H), 6.07 (s, 1H), 6.40 (s, 1H), 6.97-7.20 (m, 4H), 7.27 (d, J = 11.8 Hz, 1H), 7.45 (s, 1H), 7.61-7.66 (m, 1H). |
| 114 | Prepared by the procedure of Example 1 | 414 | $^1$H NMR (400 MHz, CD$_3$OD): δ 1.52-1.55 (m, 2H), 1.87-1.90 (m, 2H), 2.83-3.95 (m, 3H), 3.49 (s, 3H), 3.59-3.67 (m, 5H), 6.23 (s, 1H), 6.81 (d, J = 8.4 Hz, 1H), 6.98-7.08 (m, 4H), 8.14 (t, J = 8.0 Hz, 1H), 7.24 (m, 3H). |
| 115 | Prepared by the procedure of Example 1 | 410 | $^1$H NMR (400 MHz, CD$_3$OD): δ 1.90-2.05 (m, 2H), 2.16-2.19 (m, 2H), 3.12-3.20 (m, 2H), 3.44-3.49 (m, 1H), 3.62 (s, 3H), 3.88 (s, 3H), 3.90-3.92 (m, 2H), 6.88-6.90 (m, 1H), 7.02-7.06 (m, 1H), 7.08-7.13 (m, 1H), 8.07 (d, J = 6.0 Hz, 2H), 8.79 (d, J = 6.0 Hz, 2H). |

TABLE 3-continued

| Chemical Synthesis Example | Structure (prepared by procedure of cited Example) | MS (ESI) m/z | NMR spectrum data |
|---|---|---|---|
| 116 | Prepared by the procedure of Example 1 | 415 | ¹H NMR (400 MHz, CD₃OD): δ 1.50-1.53 (m, 2H), 1.86-1.89 (m, 2H), 2.82-3.95 (m, 3H), 3.48 (s, 3H), 3.60-3.69 (m, 5H), 6.24 (s, 1H), 6.81 (d, J = 8.4 Hz, 1H), 7.03 (s, 1H), 7.18-7.24 (m 4H), 8.17 (t, J = 4.4 Hz, 1H). |
| 117 | Prepared by the procedure of Example 1 | 444 | ¹H NMR (400 MHz, CD₃OD): δ 1.62-1.68 (m, 2H), 2.01-2.03 (m, 2H), 2.96-3.06 (m, 3H), 3.55 (s, 3H), 3.71-3.74 (m, 5H), 3.81 (s, 3H), 6.36 (d, J = 3.2 Hz, 1H), 6.65 (d, J = 8.8 Hz, 1H), 6.93 (t, J = 8.8 Hz, 1H), 7.13 (d, J = 3.2 Hz, 1H), 7.29-7.38 (m, 4H). |
| 118 | Prepared by the procedure of Example 1 | 434 | ¹H NMR (300 MHz, CD₃OD): δ 1.84-1.89 (m, 2H), 2.12-2.16 (m, 2H), 3.13 (t, J = 12.0 Hz, 2H), 3.31-3.41 (m, 1H), 3.57 (s, 3H), 3.84 (s, 3H), 3.84-3.86 (m, 2H), 6.79-6.82 (m, 1H), 6.93-7.00 (m, 2H), 7.38 (t, J = 7.5 Hz, 1H), 7.54 (d, J = 8.4 Hz, 1H), 7.64 (d, J = 7.8 Hz, 1H), 7.78 (s, 1H). |
| 119 | Prepared by the procedure of Example 1 | 434 | ¹H NMR (300 MHz, DMSO-d6): δ 1.70-1.74 (m, 2H), 1.99-2.03 (m, 2H), 2.95 (t, J = 12.0 Hz, 2H), 3.23-3.24 (m, 1H), 3.44 (s, 3H), 3.74 (s, 3H), 3.84-3.86 (m, 2H), 6.68-6.70 (m, 1H), 6.91-6.96 (m, 2H), 7.31-7.34 (m, 1H), 7.40-7.59 (m, 2H), 7.77-7.80 (m, 1H), 8.34 (m, 3H). |

Preparation 120A: [1-(5-chloro-4-cyano-1-methyl-6-oxo-1,6-dihydro-pyrimidin-2-yl)-piperidin-4-yl]-carbamic Acid Tert-Butyl Ester

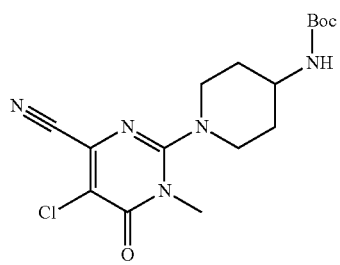 [SMILES: Cn1c(N2CCC(NC(=O)OC(C)(C)C)CC2)nc(C#N)c(Cl)c1=O]

A mixture of N-[1-(5,6-dichloro-3-methyl-4-oxo(3-hydropyrimidin-2-yl))(4-piperidyl)](tert-butoxy)carboxamide (2.4 g, 6.38 mmol), Zn(CN)$_2$ (388 mg, 3.32 mmol) and Pd(PPh$_3$)$_4$ (740 mg, 0.64 mmol) in DMF (20 mL) was stirred at 130° C. for 5 h under N$_2$ atmosphere. The reaction mixture was cooled to RT and filtered. The filtrate was concentrated in vacuo, and the residue was purified by preparative HPLC to give 200 mg of the title product (9%). [M+H] Calc'd for C$_{16}$H$_{22}$ClN$_5$O$_3$, 368. Found, 368.

Preparation 120B: {1-[4-cyano-5-(3-fluoro-4-methoxy-phenyl)-1-methyl-6-oxo-1,6-dihydro-pyrimidin-2-yl]-piperidin-4-yl}-carbamic Acid Tert-Butyl Ester

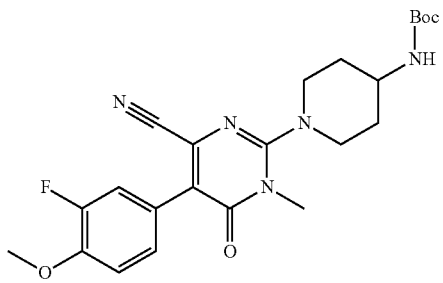 [SMILES: COc1ccc(-c2c(C#N)nc(N3CCC(NC(=O)OC(C)(C)C)CC3)n(C)c2=O)cc1F]

A mixture of [1-(5-chloro-4-cyano-1-methyl-6-oxo-1,6-dihydro-pyrimidin-2-yl)-piperidin-4-yl]-carbamic acid tert-butyl ester (200 mg, 0.54 mmol), 3-fluoro-4-methoxybenzeneboronic acid (278 mg, 1.63 mmol), Pd(dppf)$_2$Cl$_2$ (119 mg, 0.16 mmol), and Na$_2$CO$_3$ (173 mg, 1.63 mmol) in dioxane (5 mL) and H$_2$O (1 mL) was degassed with N$_2$ and stirred at 145° C. in the microwave for 2 h. The reaction mixture was cooled to RT and filtered. The filtrate was concentrated in vacuo and the residue purified by preparative HPLC to give 110 mg of the desired product (45%). [M+H] Calc'd for C$_{23}$H$_{28}$FN$_5$O$_4$, 458. Found, 458.

Example 120: 2-(4-amino-piperidin-1-yl)-5-(3-fluoro-4-methoxy-phenyl)-1-methyl-6-oxo-1,6-dihydro-pyrimidine-4-carbonitrile

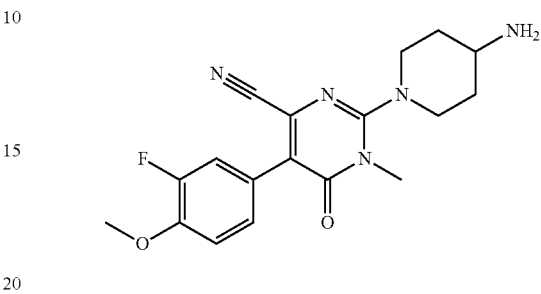

A mixture of {1-[4-cyano-5-(3-fluoro-4-methoxy-phenyl)-1-methyl-6-oxo-1,6-dihydro-pyrimidin-2-yl]-piperidin-4-yl}-carbamic acid tert-butyl ester (100 mg, 0.23 mmol) in EA (5 mL) was added a 5N HCl solution in EA (5 mL) was stirred at RT for 2 h. The solvent was concentrated in vacuo to give 85 mg of the title product as the HCl salt (93%). $^1$H NMR (400 MHz, CD$_3$OD): δ 1.71-1.75 (m, 2H), 1.89-2.03 (m, 2H), 2.96-3.02 (m, 2H), 3.27-3.31 (m, 1H), 3.42 (s, 3H), 3.69-3.73 (m, 2H), 3.83 (s, 3H), 7.06 (t, J=8.0 Hz, 1H), 7.17-2.01 (m, 2H). [M+H] Calc'd for C$_{18}$H$_{20}$FN$_5$O$_2$, 358. Found, 358.

Preparation 121A: {1-[5-cyano-4-(4-cyano-3-fluoro-phenyl)-1-methyl-6-oxo-1,6-dihydro-pyrimidin-2-yl]-piperidin-4-yl}-carbamic Acid Tert-Butyl Ester

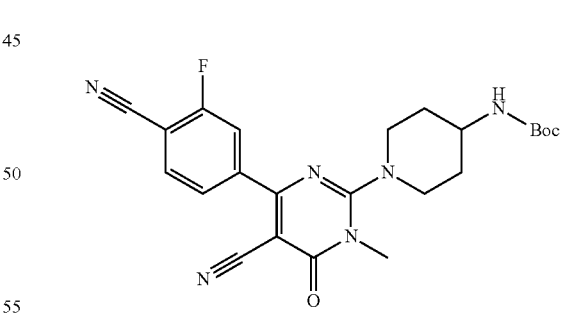

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (460 mg, 1 mmol), Zn(CN)$_2$ (175 mg, 1.5 mmol) and Pd(PPh$_3$)$_4$ (116 mg, 0.0.1 mmol) in DMF (5 mL) was stirred 4 h at 150° C. under N$_2$ atmosphere. The mixture was cooled to RT and filtered. The filtrate was concentrated in vacuo, and the residue purified by preparative HPLC to give 150 mg of the title product as a yellow solid (33%). [M+H] Calc'd for C$_{23}$H$_{25}$FN$_6$O$_3$, 453. Found, 453.

Example 121: 2-(4-amino-piperidin-1-yl)-4-(4-cyano-3-fluoro-phenyl)-1-methyl-6-oxo-1,6-dihydro-pyrimidine-5-carbonitrile

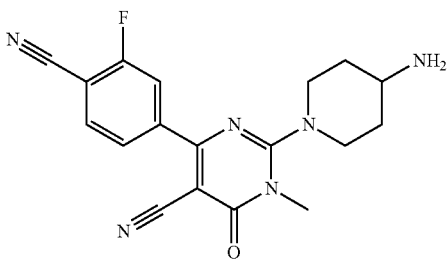

To a mixture of {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5 N HCl solution in EA (5 mL), and the mixture was stirred at RT for 2 h. The solvent was concentrated in vacuo to give 120 mg the title product as HCl salt (94%). $^1$H NMR (400 MHz, CD$_3$OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C$_{18}$H$_{17}$FN$_6$O, 353. Found, 353.

Preparation 122A: 4-cyano-3-fluoro-benzoyl Chloride

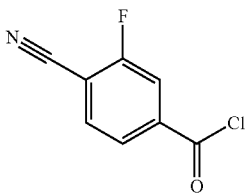 [SMILES: N#Cc1ccc(C(=O)Cl)cc1F]

A mixture of 4-cyano-3-fluoro-benzoic acid (2.0 g, 12.12 mmol) in SOCl$_2$ (20 mL) was refluxed for 2 h, and SOCl$_2$ was removed in vacuo to give 4-cyano-3-fluoro-benzoyl chloride (2.2 g, 99%). The crude was carried to the next step without further purification.

Preparation 122B: 3-(4-cyano-3-fluoro-phenyl)-2-(4-methoxy-phenyl)-3-oxo-propionic Acid Methyl Ester

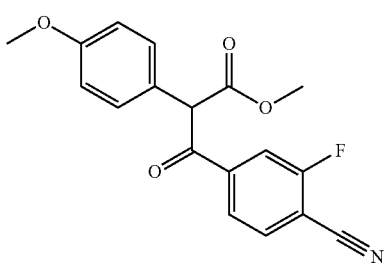 [SMILES: COC(=O)C(C(=O)c1ccc(C#N)c(F)c1)c1ccc(OC)cc1]

To a solution of (4-methoxy-phenyl)-acetic acid (2.18 g, 12.12 mmol) in THF (20 mL) was added LiHMDS (18.2 mL, 18.18 mmol) at −78° C. and the mixture was stirred for 30 min. A solution of 4-cyano-3-fluoro-benzoyl chloride (2.2 g, 12 mmol) in THF was added dropwise at −78° C., and the reaction mixture was allowed to warm up to RT and stirred at overnight. Aqueous NH$_4$Cl was added and the aqueous was extracted with EA (3×). The combined organics were concentrated in vacuo and the residue was purified by silica column chromatography (1:5, EA: PE) to give 1.8 g (45%) of the title compound. [M+H] Calc'd for C$_{18}$H$_{14}$FNO$_4$, 328. Found, 328.

Preparation 122C: {1-[4-(4-cyano-3-fluoro-phenyl)-5-(4-methoxy-phenyl)-6-oxo-1,6-dihydro-pyrimidin-2-yl]-piperidin-4-yl}-carbamic Acid Tert-Butyl Ester

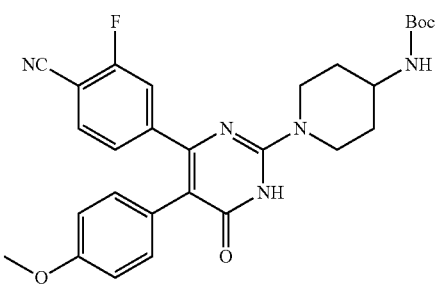 [SMILES: COc1ccc(-c2c(-c3ccc(C#N)c(F)c3)nc(N3CCC(NC(=O)OC(C)(C)C)CC3)[nH]c2=O)cc1]

A mixture of 3-(4-cyano-3-fluoro-phenyl)-2-(4-methoxy-phenyl)-3-oxo-propionic acid methyl ester (1.8 g, 5.5 mmol), (1-carbamimidoyl-piperidin-4-yl)-carbamic acid tert-butyl ester (2.6 g, 9.2 mmol), DIEA (2.4 g, 18.3 mmol) in toluene (50 mL) was refluxed overnight. The solvent was concentrated in vacuo. The residue was suspended in MeOH and the solids were filtered to give 100 mg (4%) of the title compound. [M+H] Calc'd for C$_{28}$H$_{30}$FN$_5$O$_4$, 520. Found, 520.

Example 122: 4-[2-(4-amino-piperidin-1-yl)-5-(4-methoxy-phenyl)-6-oxo-1,6-dihydro-pyrimidin-4-yl]-2-fluoro-benzonitrile

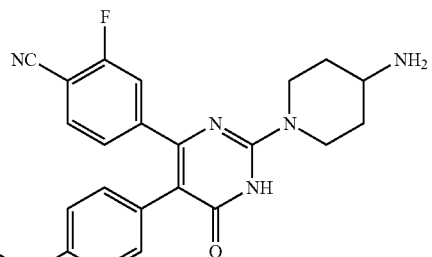

To a solution of {1-[4-(4-cyano-3-fluoro-phenyl)-5-(4-methoxy-phenyl)-6-oxo-1,6-dihydro-pyrimidin-2-yl]-piperidin-4-yl}-carbamic acid tert-butyl ester (50 mg, 0.096 mmol) in EA (10 mL) was added a 5M HCl solution in EA and the mixture was stirred at RT for 2 h. The solvent was removed in vacuo and the residue was purified by preparative HPLC to give 18 mg (40%) of the title compound as the hydrochloride salt. $^1$H NMR (400 MHz, CD$_3$OD): δ 1.81-1.87 (m, 2H), 2.22-2.25 (m, 2H), 3.34-3.38 (m, 2H), 3.56-3.60 (m, 1H), 3.78 (s, 3H), 4.61-4.64 (m, 2H), 6.86 (d, J=7.2 Hz, 2H), 7.08 (d, J=8.4 Hz, 2H), 7.37-7.38 (m, 1H), 7.51-7.53 (m, 1H), 7.74 (s, 1H). [M+H] Calc'd for C$_{23}$H$_{22}$FN$_5$O$_2$, 420. Found, 420.

II. Biological Evaluation

Example 1a: In Vitro Enzyme Inhibition Assay—LSD-1

This assay determines the ability of a test compound to inhibit LSD1 demethylase activity. *E. coli* expressed full-length human LSD1 (Accession number 060341) was purchased from Active Motif (Cat #31334).

The enzymatic assay of LSD1 activity is based on Time Resolved-Fluorescence Resonance Energy Transfer (TR-FRET) detection. The inhibitory properties of compounds to LSD1 were determined in 384-well plate format under the following reaction conditions: 0.1-0.5 nM LSD1, 50 nM H3K4me1-biotin labeled peptide (Anaspec cat #64355), 2 μM FAD in assay buffer of 50 mM HEPES, pH7.3, 10 mM NaCl, 0.005% Brij35, 0.5 mM TCEP, 0.2 mg/ml BSA. Reaction product was determined quantitatively by TR-FRET after the addition of detection reagent Phycolink Streptavidin-allophycocyanin (Prozyme) and Europium-anti-unmodified histone H3 lysine 4 (H3K4) antibody (PerkinElmer) in the presence of LSD1 inhibitor such as 1.8 mM of Tranylcypromine hydrochloride (2-PCPA) in LANCE detection buffer (PerkinElmer) to final concentration of 12.5 nM and 0.25 nM respectively.

The assay reaction was performed according to the following procedure: 2 μL of the mixture of 150 nM H3K4me1-biotin labeled peptide with 2 μL of 11-point serial diluted test compound in 3% DMSO were added to each well of plate, followed by the addition of 2 μL of 0.3 nM LSD1 and 6 μM of FAD to initiate the reaction. The reaction mixture was then incubated at room temperature for one hour, and terminated by the addition of 6 μL of 1.8 mM 2-PCPA in LANCE detection buffer containing 25 nM Phycolink Streptavidin-allophycocyanin and 0.5 nM Europium-anti-unmodified H3K4 antibody. Enzymatic reaction is terminated within 15 minutes if 0.5 LSD1 enzyme is used in the plate. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

The ability of the compounds disclosed herein to inhibit LSD1 activity was quantified and the respective IC$_{50}$ value was determined. Table 4 provides the IC$_{50}$ values of various substituted heterocyclic compounds disclosed herein.

TABLE 4

| Chemical Synthesis Example | Name | LSD1 IC$_{50}$ (μM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 2 | 4-[2-(4-amino-piperidin-1-yl)-5-(4-methoxy-phenyl)-1-methyl-6-oxo-1,6-dihydro-pyrimidin-4-yl]-benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-piperidin-1-yl)-1-methyl-5-(6-methyl-pyridin-3-yl)-6-oxo-1,6-dihydro-pyrimidin-4-yl]-benzonitrile | A |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 10 | 4-[2-(4-amino-piperidin-1-yl)-5-(6-ethyl-pyridin-3-yl)-1-methyl-6-oxo-1,6-dihydro-pyrimidin-4-yl]-benzonitrile | A |
| 11 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile | A |
| 12 | 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile | A |
| 13 | 4-[2-(4-amino-piperidin-1-yl)-1-ethyl-6-oxo-1,6-dihydro-pyrimidin-4-yl]-2-fluoro-benzonitrile | B |
| 14 | 4-[2-(4-amino-piperidin-1-yl)-5-cyclopentylethynyl-1-methyl-6-oxo-1,6-dihydro-pyrimidin-4-yl]-2-fluoro-benzonitrile | A |
| 15 | [2-(4-amino-piperidin-1-yl)-4-(4-cyano-3-fluoro-phenyl)-5-(4-methoxy-phenyl)-6-oxo-6H-pyrimidin-1-yl]-acetic acid | A |
| 16 | 2-[2-(4-amino-piperidin-1-yl)-4-(4-cyano-3-fluoro-phenyl)-5-(4-methoxy-phenyl)-6-oxo-6H-pyrimidin-1-yl]-acetamide | A |
| 17 | 4-[2-(4-amino-piperidin-1-yl)-1-(3-hydroxy-propyl)-6-oxo-1,6-dihydro-pyrimidin-4-yl]-2-fluoro-benzonitrile | B |
| 18 | 4-[2-(4-amino-piperidin-1-yl)-5-benzofuran-5-yl-1-methyl-6-oxo-1,6-dihydro-pyrimidin-4-yl]-2-fluoro-benzonitrile | A |
| 19 | 2-(4-amino-piperidin-1-yl)-4-(4-cyano-3-fluoro-phenyl)-1-methyl-6-oxo-1,6-dihydro-pyrimidine-5-carbonitrile | A |
| 20 | 4-[2-(4-aminopiperidin-1-yl)-5-chloro-1-methyl-6-oxopyrimidin-4-yl]-2-fluorobenzonitrile | A |

TABLE 4-continued

| Chemical Synthesis Example | Name | LSD1 IC$_{50}$ (μM) |
|---|---|---|
| 21 | 2-fluoro-4-[1-methyl-2-(4-methylamino-piperidin-1-yl)-5-(6-methyl-pyridin-3-yl)-6-oxo-1,6-dihydro-pyrimidin-4-yl]-benzonitrile | A |
| 22 | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluoro-benzonitrile | A |
| 23 | 4-{2-(4-aminopiperidyl)-1-methyl-6-oxo-5-[6-(trifluoromethyl) (3-pyridyl)] hydropyrimidin-4-yl}-2-fluorobenzenecarbonitrile | A |
| 24 | 4-[2-(4-aminopiperidyl)-1-methyl-5-(2-methyl(2H-indazol-5-yl))-6-oxohydropyrimidin-4-yl]benzenecarbonitrile | A |
| 25 | 4-[2-((3R)-3-aminopiperidyl)-5-(3-fluoro-4-methoxyphenyl)-1-methyl-6-oxohydropyrimidin-4-yl]-2-fluorobenzenecarbonitrile | A |
| 26 | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile | A |
| 27 | 4-[2-((3R)-3-aminopyrrolidinyl)-5-(3-fluoro-4-methoxyphenyl)-1-methyl-6-oxohydropyrimidin-4-yl]-2-fluorobenzenecarbonitrile | A |
| 28 | 4-[2-((3S)-3-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 29 | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile | A |
| 30 | 4-[2-((3R)-3-aminopiperidyl)-5-(4-methoxyphenyl)-1-methyl-6-oxohydro pyrimidin-4-yl]-2-fluorobenzenecarbonitrile | A |
| 31 | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile | A |
| 32 | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrile | A |
| 33 | 4-[2-(4-aminopiperidyl)-1-methyl-5-(1-methyl(1H-indazol-5-yl))-6-oxohydropyrimidin-4-yl]benzenecarbonitrile | A |
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile | A |
| 37 | 4-[2-(4-aminopiperidyl)-1-methyl-5-(2-methyl(2H-indazol-5-yl))-6-oxohydropyrimidin-4-yl]-2-fluorobenzenecarbonitrile | A |
| 38 | 4-[2-(4-aminopiperidyl)-5-(3,5-difluoro-4-methoxyphenyl)-1-methyl-6-oxohydropyrimidin-4-yl]benzenecarbonitrile | A |
| 39 | 4-[2-(4-aminopiperidyl)-6-(4-cyano-3-fluorophenyl)-3-methyl-4-oxo-3-hydropyrimidin-5-yl]benzoic acid | B |
| 40 | {4-[2-(4-aminopiperidyl)-6-(4-cyanophenyl)-3-methyl-4-oxo(3-hydro-pyrimidin-5-yl)]-2-fluorophenyl}-N-methylcarboxamide | A |
| 41 | 4-[2-(4-aminopiperidyl)-6-(4-cyanophenyl)-3-methyl-4-oxo(3-hydro-pyrimidin-5-yl)]-2-fluorobenzamide | A |
| 42 | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile | A |
| 43 | 3-[2-(4-amino-piperidin-1-yl)-4-(4-cyano-3-fluoro-phenyl)-1-methyl-6-oxo-1,6-dihydro-pyrimidin-5-yl]-benzoic acid | C |
| 44 | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl}-benzonitrile | A |
| 45 | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl}-benzonitrile | A |
| 46 | 4-[2-[1,4]diazepan-1-yl-5-(3-fluoro-4-methoxy-phenyl)-1-methyl-6-oxo-1,6-dihydro-pyrimidin-4-yl]-2-fluoro-benzonitrile | A |
| 47 | 2-fluoro-4-[5-(3-fluoro-4-methoxy-phenyl)-1-methyl-6-oxo-2-piperazin-1-yl-1,6-dihydro-pyrimidin-4-yl]-benzonitrile | A |
| 48 | 4-[5-(3-fluoro-4-methoxy-phenyl)-1-methyl-6-oxo-2-(piperidin-4-ylamino)-1,6-dihydro-pyrimidin-4-yl]-benzonitrile | A |
| 49 | 4-[2-(4-amino-piperidin-1-yl)-2'-dimethylamino-1-methyl-6-oxo-1,6-dihydro-[5,5']bipyrimidinyl-4-yl]-2-fluoro-benzonitrile | A |
| 50 | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide | A |
| 51 | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl}-benzonitrile | A |
| 52 | 2-luoro-4-{5-(4-methoxy-phenyl)-1-methyl-6-oxo-2-[(3R)-(pyrrolidin-3-ylmethyl)-amino]-1,6-dihydro-pyrimidin-4-yl}-benzonitrile | A |
| 53 | 2-fluoro-4-[5-(4-methoxy-phenyl)-1-methyl-6-oxo-2-(piperidin-4-yl amino)-1,6-dihydro-pyrimidin-4-yl]-benzonitrile | A |
| 54 | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile | A |
| 55 | 2-fluoro-4-[5-(4-methoxy-phenyl)-1-methyl-2-(methyl-piperidin-4-yl-amino)-6-oxo-1,6-dihydro-pyrimidin-4-yl]-benzonitrile | A |
| 56 | 2-fluoro-4-[5-(4-methoxy-phenyl)-1-methyl-2-(methyl-pyrrolidin-3-ylmethyl-amino)-6-oxo-1,6-dihydro-pyrimidin-4-yl]-benzonitrile | A |
| 57 | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile | A |

TABLE 4-continued

| Chemical Synthesis Example | Name | LSD1 IC$_{50}$ (μM) |
|---|---|---|
| 58 | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile | A |
| 59 | 4-[2-(4-amino-piperidin-1-yl)-5-(4-dimethylamino-phenyl)-1-methyl-6-oxo-1,6-dihydro-pyrimidin-4-yl]-2-fluoro-benzonitrile | A |
| 60 | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile | A |
| 61 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 62 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 63 | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile | A |
| 64 | 4-[2-(3-amino-azetidin-1-yl)-5-(4-methoxy-phenyl)-1-methyl-6-oxo-1,6-dihydro-pyrimidin-4-yl]-2-fluoro-benzonitrile | A |
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile | A |
| 67 | 4-[2-[1,4]diazepan-1-yl-5-(6-dimethylamino-pyridin-3-yl)-1-methyl-6-oxo-1,6-dihydro-pyrimidin-4-yl]-benzonitrile | A |
| 68 | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile | A |
| 69 | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile | A |
| 70 | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 72 | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile | A |
| 73 | 4-[2-(4-amino-piperidin-1-yl)-5-(1H-indol-5-yl)-1-methyl-6-oxo-1,6-dihydro-pyrimidin-4-yl]-2-fluoro-benzonitrile | A |
| 74 | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile | A |
| 75 | 4-[2-(4-amino-piperidin-1-yl)-5-(1H-indol-6-yl)-1-methyl-6-oxo-1,6-dihydro-pyrimidin-4-yl]-2-fluoro-benzonitrile | A |
| 76 | 4-[2-(4-amino-piperidin-1-yl)-1-methyl-5-(1-methyl-1H-indol-6-yl)-6-oxo-1,6-dihydro-pyrimidin-4-yl]-2-fluoro-benzonitrile | A |
| 77 | 4-[2-(4-amino-piperidin-1-yl)-5-(1H-indazol-6-yl)-1-methyl-6-oxo-1,6-dihydro-pyrimidin-4-yl]-2-fluoro-benzonitrile | A |
| 78 | 4-[2-((4R,3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 79 | 4-[2-((4S,3R)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 80 | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile | A |
| 81 | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile | A |
| 82 | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile | A |
| 83 | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile | A |
| 84 | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile | A |
| 85 | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile | A |
| 86 | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile | A |
| 87 | 2-fluoro-4-[1-methyl-2-[4-(methylamino)piperidin-1-yl]-5-(1-methylindazol-5-yl)-6-oxopyrimidin-4-yl]benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |
| 89 | 4-[5-(4-aminophenyl)-2-(4-aminopiperidin-1-yl)-1-methyl-6-oxopyrimidin-4-yl]-2-fluorobenzonitrile | A |
| 90 | 4-[2-(4-aminopiperidin-1-yl)-1-methyl-5-[4-(methylamino)phenyl]-6-oxopyrimidin-4-yl]-2-fluorobenzonitrile | A |
| 91 | 4-[2-(4-aminopiperidin-1-yl)-5-[3-fluoro-4-(methylamino)phenyl]-1-methyl-6-oxopyrimidin-4-yl]-2-fluorobenzonitrile | A |
| 92 | 4-[2-[4-(dimethylamino)piperidin-1-yl]-5-(6-methoxypyridin-3-yl)-1-methyl-6-oxopyrimidin-4-yl]-2-fluorobenzonitrile | A |
| 93 | 4-[2-(4-aminopiperidin-1-yl)-5-(6-ethoxy-5-fluoropyridin-3-yl)-1-methyl-6-oxopyrimidin-4-yl]-2-fluorobenzonitrile | A |
| 94 | 4-[2-(4-aminopiperidin-1-yl)-5-(6-ethoxypyridin-3-yl)-1-methyl-6-oxopyrimidin-4-yl]-2-fluorobenzonitrile | A |
| 95 | 4-[2-(4-aminopiperidin-1-yl)-5-(4-ethoxyphenyl)-1-methyl-6-oxopyrimidin-4-yl]-2-fluorobenzonitrile | A |

TABLE 4-continued

| Chemical Synthesis Example | Name | LSD1 IC$_{50}$ (µM) |
|---|---|---|
| 96 | 4-[2-(4-aminopiperidin-1-yl)-5-[4-(2-hydroxyethoxy)phenyl]-1-methyl-6-oxopyrimidin-4-yl]-2-fluorobenzonitrile | A |
| 97 | 4-[2-(4-aminopiperidin-1-yl)-5-[4-(2-hydroxyethoxy)phenyl]-1-methyl-6-oxopyrimidin-4-yl]benzonitrile | A |
| 98 | 4-[2-(4-aminopiperidin-1-yl)-5-[4-(2-methoxyethoxy)phenyl]-1-methyl-6-oxopyrimidin-4-yl]-2-fluorobenzonitrile | A |
| 99 | 4-[2-(4-aminopiperidin-1-yl)-5-[4-(2-hydroxyethyl)phenyl]-1-methyl-6-oxopyrimidin-4-yl]-2-fluorobenzonitrile | A |
| 100 | 4-[2-(4-aminopiperidin-1-yl)-5-[4-(hydroxymethyl)phenyl]-1-methyl-6-oxopyrimidin-4-yl]-2-fluorobenzonitrile | A |
| 101 | 4-[2-(4-aminopiperidin-1-yl)-5-(4-fluorophenyl)-1-methyl-6-oxopyrimidin-4-yl]-2-fluorobenzonitrile | A |
| 102 | 4-[2-(4-aminopiperidin-1-yl)-5-(3-fluorophenyl)-1-methyl-6-oxopyrimidin-4-yl]-2-fluorobenzonitrile | A |
| 103 | 4-[2-(4-aminopiperidin-1-yl)-5-(3,5-difluorophenyl)-1-methyl-6-oxopyrimidin-4-yl]-2-fluorobenzonitrile | A |
| 104 | 4-[2-(4-aminopiperidin-1-yl)-5-(3,4-difluorophenyl)-1-methyl-6-oxopyrimidin-4-yl]-2-fluorobenzonitrile | A |
| 105 | 4-[2-(4-aminopiperidin-1-yl)-1-methyl-5-(4-methylsulfonylphenyl)-6-oxopyrimidin-4-yl]-2-fluorobenzonitrile | A |
| 106 | 4-[2-(4-aminopiperidin-1-yl)-5-(4-chlorophenyl)-1-methyl-6-oxopyrimidin-4-yl]-2-fluorobenzonitrile | A |
| 107 | 4-[2-(4-aminopiperidin-1-yl)-5-[4-(methoxymethyl)phenyl]-1-methyl-6-oxopyrimidin-4-yl]-2-fluorobenzonitrile | A |
| 108 | 4-[2-(4-aminopiperidin-1-yl)-1-methyl-6-oxopyrimidin-4-yl]-2-fluorobenzonitrile | A |
| 109 | 4-[2-(4-amino-piperidin-1-yl)-1-cyclopropylmethyl-6-oxo-1,6-dihydro-pyrimidin-4-yl]-2-fluoro-benzonitrile | B |
| 110 | 4-[2-(4-amino-piperidin-1-yl)-1-cyclopropylmethyl-6-oxo-1,6-dihydro-pyrimidin-4-yl]-2-fluoro-benzonitrile | A |
| 111 | 2-(4-amino-piperidin-1-yl)-6-(4-chloro-3-fluoro-phenyl)-5-(4-methoxy-phenyl)-3-methyl-3H-pyrimidin-4-one | B |
| 112 | 2-(4-amino-piperidin-1-yl)-6-(4-hydroxy-phenyl)-3-methyl-5-(1-methyl-1H-indol-5-yl)-3H-pyrimidin-4-one | D |
| 113 | 2-(4-amino-piperidin-1-yl)-6-(4-fluoro-phenyl)-3-methyl-5-(1-methyl-1H-indol-5-yl)-3H-pyrimidin-4-one | B |
| 114 | 2-(4-amino-piperidin-1-yl)-3-methyl-5-(1-methyl-1H-indol-5-yl)-6-phenyl-3H-pyrimidin-4-one | D |
| 115 | 2-(4-amino-piperidin-1-yl)-5-(3-fluoro-4-methoxy-phenyl)-3-methyl-6-pyridin-4-yl-3H-pyrimidin-4-one | C |
| 116 | 2-(4-amino-piperidin-1-yl)-3-methyl-5-(1-methyl-1H-indol-5-yl)-6-pyridin-4-yl-3H-pyrimidin-4-one | B |
| 117 | 2-(4-amino-piperidin-1-yl)-6-(4-methoxy-phenyl)-3-methyl-5-(1-methyl-1H-indol-5-yl)-3H-pyrimidin-4-one | C |
| 118 | 3-[2-(4-aminopiperidin-1-yl)-5-(3-fluoro-4-methoxyphenyl)-1-methyl-6-oxopyrimidin-4-yl]benzonitrile | D |
| 119 | 2-[2-(4-aminopiperidin-1-yl)-5-(3-fluoro-4-methoxyphenyl)-1-methyl-6-oxopyrimidin-4-yl]benzonitrile | D |
| 120 | 2-(4-amino-piperidin-1-yl)-5-(3-fluoro-4-methoxy-phenyl)-1-methyl-6-oxo-1,6-dihydro-pyrimidine-4-carbonitrile | C |
| 121 | 2-(4-amino-piperidin-1-yl)-4-(4-cyano-3-fluoro-phenyl)-1-methyl-6-oxo-1,6-dihydro-pyrimidine-5-carbonitrile | B |
| 122 | 4-[2-(4-aminopiperidin-1-yl)-5-(4-methoxyphenyl)-6-oxo-1H-pyrimidin-4-yl]-2-fluorobenzonitrile | A |

Note:
Biochemical assay IC$_{50}$ data are designated within the following ranges:
A: ≤0.10 µM;
B: >0.10 µM to ≤1.0 µM;
C: >1.0 µM to ≤10 µM;
D: >10 µM

Example 2: In Vitro Enzyme Inhibition Assay—MAO Selectivity

Human recombinant monoamine oxidase proteins MAO-A and MAO-B are obtained. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay is performed. 3-(2-Aminophenyl)-3-oxopropanamine (kynuramine dihydrobromide, Sigma Aldrich), a non-fluorescent compound is chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µl. The assay buffer was 100 mM HEPES, pH 7.5. Each experiment was performed in triplicate within the same experiment.

Briefly, a fixed amount of MAO (0.25 µg for MAO-A and 0.5 µg for AO-B) was incubated on ice for 15 minutes in the reaction buffer, in the absence and/or in the presence of various concentrations of compounds as disclosed herein (e.g., from 0 to 50 µM, depending on the inhibitor strength). Tranylcypromine (Biomol International) was used as a control for inhibition.

After leaving the enzyme(s) interacting with the test compound, 60 to 90 µM of kynuramine was added to each reaction for MAO-B and MAO-A assay respectively, and the reaction was left for 1 hour at 37° C. in the dark. The oxidative deamination of the substrate was stopped by adding 50 µl of 2N NaOH. The conversion of kynuramine to 4-hydroxyquinoline was monitored by fluorescence (excitation at 320 nm, emission at 360 nm) using a microplate reader (Infinite 200, Tecan). Arbitrary units were used to measure levels of fluorescence produced in the absence and/or in the presence of test compound.

The maximum of oxidative deamination activity was obtained by measuring the amount of 4-hydroxyquinoline formed from kynuramine deamination in the absence of test compound and corrected for background fluorescence. The $K_i$ ($IC_{50}$) of each inhibitor was determined at Vmax/2. Chemical synthesis examples 1-94, 101-106, 108-117, and 120-122 were tested in the above described assay and found to have an $IC_{50}$ greater than 2 micromolar.

Example 3: LSD1 CD11b Cellular Assay

To analyze LSD1 inhibitor efficacy in cells, a CD11b flow cytometry assay was performed. LSD1 inhibition induces CD11b expression in THP-1 (AML) cells which is measured by flow cytometry. THP-1 cells were seeded at 100,000 cells/well in 10% Fetal Bovine Serum containing RPMI 1640 media in a 24 well plate with a final volume of 500 µL per well. LSD1 test compounds where serially diluted in DMSO. The dilutions were added to each well accordingly to a final concentration of 0.2% DMSO. The cells were incubated at 37 degrees Celsius in 5% $CO_2$ for 4 days. 250 µL of each well was transferred to a well in a 96 well round bottom plate. The plate was centrifuged at 1200 rpm at 4 degrees Celsius in a Beckman Coulter Alegra 6KR centrifuge for 5 minutes. The media was removed leaving the cells at the bottom of the wells. The cells were washed in 100 µL cold HBSS (Hank's Balanced Salt Solution) plus 2% BSA (Bovine Serum Albumin) solution and centrifuged at 1200 rpm at 4 degrees Celsius for 5 minutes. The wash was removed. The cells were resuspended in 100 µL HBSS plus 2 BSA containing 1:15 dilution of APC conjugated mouse anti-CD11b antibody (BD Pharmingen Cat #555751) and incubated on ice for 25 minutes. The cells were centrifuged and washed two times in 100 PI HBSS plus 2% BSA. After the final spin the cells were resuspended in 100 µL HBSS plus 2% BSA containing 1 ug/mL DAPI (4',6-diamidino-2-phenylindole). The cells were then analyzed by flow cytometry in a BD FACSAria machine. Cells were analyzed for CD11b expression. The percent of CD11b expressing cells for each inhibitor concentration was used to determine an $IC_{50}$ curve for each compound analyzed.

Table 4 provides the cellular $IC_{50}$ values of various substituted heterocyclic compounds disclosed herein.

TABLE 5

| Chemical Synthesis Example | Name | THP-1 $IC_{50}$ (µM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 2 | 4-[2-(4-amino-piperidin-1-yl)-5-(4-methoxy-phenyl)-1-methyl-6-oxo-1,6-dihydro-pyrimidin-4-yl]-benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-piperidin-1-yl)-1-methyl-5-(6-methyl-pyridin-3-yl)-6-oxo-1,6-dihydro-pyrimidin-4-yl]-benzonitrile | A |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 10 | 4-[2-(4-amino-piperidin-1-yl)-5-(6-ethyl-pyridin-3-yl)-1-methyl-6-oxo-1,6-dihydro-pyrimidin-4-yl]-benzonitrile | B |
| 11 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile | A |
| 12 | 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile | A |
| 14 | 4-[2-(4-amino-piperidin-1-yl)-5-cyclopentylethynyl-1-methyl-6-oxo-1,6-dihydro-pyrimidin-4-yl]-2-fluoro-benzonitrile | A |
| 15 | [2-(4-amino-piperidin-1-yl)-4-(4-cyano-3-fluoro-phenyl)-5-(4-methoxy-phenyl)-6-oxo-6H-pyrimidin-1-yl]-acetic acid | C |
| 16 | 2-[2-(4-amino-piperidin-1-yl)-4-(4-cyano-3-fluoro-phenyl)-5-(4-methoxy-phenyl)-6-oxo-6H-pyrimidin-1-yl]-acetamide | A |
| 18 | 4-[2-(4-amino-piperidin-1-yl)-5-benzofuran-5-yl-1-methyl-6-oxo-1,6-dihydro-pyrimidin-4-yl]-2-fluoro-benzonitrile | A |
| 20 | 4-[2-(4-aminopiperidin-1-yl)-5-chloro-1-methyl-6-oxopyrimidin-4-yl]-2-fluorobenzonitrile | B |
| 22 | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluoro-benzonitrile | A |
| 23 | 4-{2-(4-aminopiperidyl)-1-methyl-6-oxo-5-[6-(trifluoromethyl)-(3-pyridyl)] hydropyrimidin-4-yl}-2-fluorobenzenecarbonitrile | A |

TABLE 5-continued

| Chemical Synthesis Example | Name | THP-1 IC$_{50}$ (μM) |
|---|---|---|
| 24 | 4-[2-(4-aminopiperidyl)-1-methyl-5-(2-methyl(2H-indazol-5-yl))-6-oxohydropyrimidin-4-yl]benzenecarbonitrile | A |
| 25 | 4-[2-((3R)-3-aminopiperidyl)-5-(3-fluoro-4-methoxyphenyl)-1-methyl-6-oxohydropyrimidin-4-yl]-2-fluorobenzenecarbonitrile | A |
| 26 | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile | A |
| 27 | 4-[2-((3R)-3-aminopyrrolidinyl)-5-(3-fluoro-4-methoxyphenyl)-1-methyl-6-oxohydropyrimidin-4-yl]-2-fluorobenzenecarbonitrile | A |
| 29 | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile | B |
| 30 | 4-[2-((3R)-3-aminopiperidyl)-5-(4-methoxy-phenyl)-1-methyl-6-oxohydro pyrimidin-4-yl]-2-fluorobenzenecarbonitrile | A |
| 31 | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile | A |
| 32 | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrile | A |
| 33 | 4-[2-(4-aminopiperidyl)-1-methyl-5-(1-methyl(1H-indazol-5-yl))-6-oxohydropyrimidin-4-yl]benzenecarbonitrile | A |
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile | A |
| 37 | 4-[2-(4-aminopiperidyl)-1-methyl-5-(2-methyl (2H-indazol-5-yl))-6-oxohydropyrimidin-4-yl]-2-fluorobenzenecarbonitrile | A |
| 38 | 4-[2-(4-aminopiperidyl)-5-(3,5-difluoro-4-methoxyphenyl)-1-methyl-6-oxohydropyrimidin-4-yl]benzenecarbonitrile | A |
| 40 | {4-[2-(4-aminopiperidyl)-6-(4-cyanophenyl)-3-methyl-4-oxo(3-hydro pyrimidin-5-yl)]-2-fluorophenyl}-N-methylcarboxamide | B |
| 41 | 4-[2-(4-aminopiperidyl)-6-(4-cyanophenyl)-3-methyl-4-oxo (3-hydro pyrimidin-5-yl)]-2-fluorobenzamide | B |
| 42 | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile | B |
| 44 | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl}-benzonitrile | B |
| 45 | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl}-benzonitrile | B |
| 46 | 4-[2-[1,4] diazepan-1-yl-5-(3-fluoro-4-methoxy-phenyl)-1-methyl-6-oxo-1,6-dihydro-pyrimidin-4-yl]-2-fluoro-benzonitrile | A |
| 47 | 2-fluoro-4-[5-(3-fluoro-4-methoxy-phenyl)-1-methyl-6-oxo-2-piperazin-1-yl-1,6-dihydro-pyrimidin-4-yl]-benzonitrile | B |
| 48 | 4-[5-(3-fluoro-4-methoxy-phenyl)-1-methyl-6-oxo-2-(piperidin-4-ylamino)-1,6-dihydro-pyrimidin-4-yl]-benzonitrile | B |
| 49 | 4-[2-(4-amino-piperidin-1-yl)-2'-dimethylamino-1-methyl-6-oxo-1,6-dihydro-[5,5']bipyrimidinyl-4-yl]-2-fluoro-benzonitrile | A |
| 50 | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide | A |
| 51 | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl}-benzonitrile | B |
| 52 | 2-luoro-4-{5-(4-methoxy-phenyl)-1-methyl-6-oxo-2-[(3R)-(pyrrolidin-3-ylmethyl)-amino]-1,6-dihydro-pyrimidin-4-yl}-benzonitrile | B |
| 53 | 2-fluoro-4-[5-(4-methoxy-phenyl)-1-methyl-6-oxo-2-(piperidin-4-ylamino)-1,6-dihydro-pyrimidin-4-yl]-benzonitrile | B |
| 54 | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile | A |
| 55 | 2-fluoro-4-[5-(4-methoxy-phenyl)-1-methyl-2-(methyl-piperidin-4-yl-amino)-6-oxo-1,6-dihydro-pyrimidin-4-yl]-benzonitrile | B |
| 56 | 2-fluoro-4-[5-(4-methoxy-phenyl)-1-methyl-2-(methyl-pyrrolidin-3-ylmethyl-amino)-6-oxo-1,6-dihydro-pyrimidin-4-yl]-benzonitrile | A |
| 57 | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile | A |
| 58 | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile | A |
| 59 | 4-[2-(4-amino-piperidin-1-yl)-5-(4-dimethylamino-phenyl)-1-methyl-6-oxo-1,6-dihydro-pyrimidin-4-yl]-2-fluoro-benzonitrile | A |
| 60 | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile | A |
| 61 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 62 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | B |
| 63 | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile | A |
| 64 | 4-[2-(3-amino-azetidin-1-yl)-5-(4-methoxy-phenyl)-1-methyl-6-oxo-1,6-dihydro-pyrimidin-4-yl]-2-fluoro-benzonitrile | B |

TABLE 5-continued

| Chemical Synthesis Example | Name | THP-1 IC$_{50}$ (μM) |
|---|---|---|
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile | A |
| 67 | 4-[2-[1,4]diazepan-1-yl-5-(6-dimethylamino-pyridin-3-yl)-1-methyl-6-oxo-1,6-dihydro-pyrimidin-4-yl]-benzonitrile | A |
| 68 | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile | A |
| 69 | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile | B |
| 70 | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 72 | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile | A |
| 73 | 4-[2-(4-amino-piperidin-1-yl)-5-(1H-indol-5-yl)-1-methyl-6-oxo-1,6-dihydro-pyrimidin-4-yl]-2-fluoro-benzonitrile | A |
| 74 | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile | A |
| 75 | 4-[2-(4-amino-piperidin-1-yl)-5-(1H-indol-6-yl)-1-methyl-6-oxo-1,6-dihydro-pyrimidin-4-yl]-2-fluoro-benzonitrile | A |
| 76 | 4-[2-(4-amino-piperidin-1-yl)-1-methyl-5-(1-methyl-1H-indol-6-yl)-6-oxo-1,6-dihydro-pyrimidin-4-yl]-2-fluoro-benzonitrile | A |
| 77 | 4-[2-(4-amino-piperidin-1-yl)-5-(1H-indazol-6-yl)-1-methyl-6-oxo-1,6-dihydro-pyrimidin-4-yl]-2-fluoro-benzonitrile | A |
| 78 | 4-[2-((4R,3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 79 | 4-[2-((4S,3R)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 80 | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile | A |
| 81 | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile | B |
| 82 | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile | B |
| 83 | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile | A |
| 84 | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile | A |
| 85 | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile | A |
| 86 | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile | A |
| 87 | 2-fluoro-4-[1-methyl-2-[4-(methylamino)piperidin-1-yl]-5-(1-methylindazol-5-yl)-6-oxopyrimidin-4-yl]benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |
| 89 | 4-[5-(4-aminophenyl)-2-(4-aminopiperidin-1-yl)-1-methyl-6-oxopyrimidin-4-yl]-2-fluorobenzonitrile | A |
| 90 | 4-[2-(4-aminopiperidin-1-yl)-1-methyl-5-[4-(methylamino)phenyl]-6-oxopyrimidin-4-yl]-2-fluorobenzonitrile | A |
| 91 | 4-[2-(4-aminopiperidin-1-yl)-5-[3-fluoro-4-(methylamino)phenyl]-1-methyl-6-oxopyrimidin-4-yl]-2-fluorobenzonitrile | A |
| 92 | 4-[2-[4-(dimethylamino)piperidin-1-yl]-5-(6-methoxypyridin-3-yl)-1-methyl-6-oxo-pyrimidin-4-yl]-2-fluorobenzonitrile | A |
| 93 | 4-[2-(4-aminopiperidin-1-yl)-5-(6-ethoxy-5-fluoropyridin-3-yl)-1-methyl-6-oxopyrimidin-4-yl]-2-fluorobenzonitrile | A |
| 94 | 4-[2-(4-aminopiperidin-1-yl)-5-(6-ethoxypyridin-3-yl)-1-methyl-6-oxopyrimidin-4-yl]-2-fluorobenzonitrile | A |
| 95 | 4-[2-(4-aminopiperidin-1-yl)-5-(4-ethoxyphenyl)-1-methyl-6-oxopyrimidin-4-yl]-2-fluorobenzonitrile | A |
| 96 | 4-[2-(4-aminopiperidin-1-yl)-5-[4-(2-hydroxyethoxy)phenyl]-1-methyl-6-oxopyrimidin-4-yl]-2-fluorobenzonitrile | A |
| 97 | 4-[2-(4-aminopiperidin-1-yl)-5-[4-(2-hydroxyethoxy)phenyl]-1-methyl-6-oxopyrimidin-4-yl]benzonitrile | A |
| 98 | 4-[2-(4-aminopiperidin-1-yl)-5-[4-(2-methoxyethoxy)phenyl]-1-methyl-6-oxopyrimidin-4-yl]-2-fluorobenzonitrile | A |
| 99 | 4-[2-(4-aminopiperidin-1-yl)-5-[4-(2-hydroxyethyl)phenyl]-1-methyl-6-oxopyrimidin-4-yl]-2-fluorobenzonitrile | A |
| 100 | 4-[2-(4-aminopiperidin-1-yl)-5-[4-(hydroxymethyl)phenyl]-1-methyl-6-oxopyrimidin-4-yl]-2-fluorobenzonitrile | A |
| 101 | 4-[2-(4-aminopiperidin-1-yl)-5-(4-fluorophenyl)-1-methyl-6-oxopyrimidin-4-yl]-2-fluorobenzonitrile | A |
| 102 | 4-[2-(4-aminopiperidin-1-yl)-5-(3-fluorophenyl)-1-methyl-6-oxopyrimidin-4-yl]-2-fluorobenzonitrile | A |

TABLE 5-continued

| Chemical Synthesis Example | Name | THP-1 IC$_{50}$ (µM) |
|---|---|---|
| 103 | 4-[2-(4-aminopiperidin-1-yl)-5-(3,5-difluorophenyl)-1-methyl-6-oxopyrimidin-4-yl]-2-fluorobenzonitrile | A |
| 104 | 4-[2-(4-aminopiperidin-1-yl)-5-(3,4-difluorophenyl)-1-methyl-6-oxopyrimidin-4-yl]-2-fluorobenzonitrile | A |
| 105 | 4-[2-(4-aminopiperidin-1-yl)-1-methyl-5-(4-methylsulfonylphenyl)-6-oxo-pyrimidin-4-yl]-2-fluorobenzonitrile | A |
| 106 | 4-[2-(4-aminopiperidin-1-yl)-5-(4-chlorophenyl)-1-methyl-6-oxopyrimidin-4-yl]-2-fluorobenzonitrile | A |
| 107 | 4-[2-(4-aminopiperidin-1-yl)-5-[4-(methoxymethyl)phenyl]-1-methyl-6-oxopyrimidin-4-yl]-2-fluorobenzonitrile | A |
| 108 | 4-[2-(4-aminopiperidin-1-yl)-1-methyl-6-oxo-pyrimidin-4-yl]-2-fluorobenzonitrile | B |
| 110 | 4-[2-(4-amino-piperidin-1-yl)-1-cyclopropylmethyl-6-oxo-1,6-dihydro-pyrimidin-4-yl]-2-fluoro-benzonitrile | B |
| 111 | 2-(4-amino-piperidin-1-yl)-6-(4-chloro-3-fluoro-phenyl)-5-(4-methoxy-phenyl)-3-methyl-3H-pyrimidin-4-one | B |
| 122 | 4-[2-(4-aminopiperidin-1-yl)-5-(4-methoxyphenyl)-6-oxo-1H-pyrimidin-4-yl]-2-fluorobenzonitrile | A |

Note:
Cellular assay IC$_{50}$ data are designated within the following ranges:
A: ≤0.10 µM;
B: >0.10 µM to ≤1.0 µM;
C: >1.0 µM to ≤10 µM;
D: >10 µM

Example 4: Kasumi-1 AML Cell Line Proliferation Assay (Cell-MTS Assay)

Colorimetric cellular assay to assess the ability of LSD-1 small molecule inhibitors to effect the proliferation of the established AML cancer cell line Kasumi-1.

Assay Background

The LSD-1 protein has been shown to play a key role in the biology of a variety of cancer types including SCLC and AML. To demonstrate small molecule inhibition of LSD-1 as a potential anti-cancer therapy, an assay to measure the degree of proliferative inhibition in an established cancer cell line of AML was implemented.

Assay Principle

This Cell-MTS assay is a 7-day plate based colorimetric assay which quantifies the amount of newly generated NADH in the presence and absence of test compound. These NADH levels are used as a proxy for the quantification of cancer cell proliferation.

Assay Method

The established cancer cell line Kasumi-1 with a verified p53 mutation were purchased from American Type Culture Collection (ATCC) and routinely passaged according to ATCC published protocols. For routine assay these cells were seeded at a density of 20,000 cells per 96-well. 24 hours after plating, cells received an 11 point dilution of test compound with final concentration ranges from 100 µM to 2.0 nM. Cells are incubated in the presence of compound for 168 hours at 37° C., 5% CO$_2$. At the end of this compound incubation period, 80 µl of media is removed and 20 µL of CellTiter 96® AQueous Non-Radioactive Cell Proliferation Assay solution (Promega) is added. The cells are incubated until the OD490 is >0.6. IC$_{50}$ values are calculated using the IDBS XLfit software package and include background subtracted OD490 values and normalization to DMSO controls.

Table 6 provides the Kasumi-1 cellular IC$_{50}$ values of various substituted heterocyclic compounds disclosed herein.

TABLE 6

| Chemical Synthesis Example | Name | Kasumi-1 IC$_{50}$ (µM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-piperidin-1-yl)-1-methyl-5-(6-methyl-pyridin-3-yl)-6-oxo-1,6-dihydro-pyrimidin-4-yl]-benzonitrile | B |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 24 | 4-[2-(4-aminopiperidyl)-1-methyl-5-(2-methyl(2H-indazol-5-yl))-6-oxohydropyrimidin-4-yl]benzenecarbonitrile | A |

TABLE 6-continued

| Chemical Synthesis Example | Name | Kasumi-1 IC$_{50}$ (μM) |
|---|---|---|
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile | A |
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |

Example 5: In Vivo Xenograph Study—MCF-7 Xenograph

Time release pellets containing 0.72 mg 17-β Estradiol are subcutaneously implanted into nu/nu mice. MCF-7 cells are grown in RPMI containing 10% FBS at 5%/CO$_2$, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 6: In Vivo Xenograph Study—LNCaP Xenograph

LNCaP cells with a stable knockdown of LSD1 (shLSD1 cells) or control cells (such as shNTC cells) are inoculated in the dorsal flank of nude mice by subcutaneous injection (such as 3×10$^6$ cells in 100 μl of 50% RPMI 1640/BD Matrigel). Mouse weight and tumor size are measured once per week and tumor volume is estimated using the formula (7i/6)(L×W), where L=length of tumor and W=width of tumor. A two sample t-test is performed to determine statistical differences in mean tumor volume between the two groups.

Unmodified LNCaP cells are inoculated by subcutaneous injection into the dorsal flank of nude mice (such as 3×10$^6$ cells in 100 μl of 50% RPMI 1640/BD Matrigel). After three weeks, mice are injected intraperitoneally once per day with water (control), pargyline (0.53 mg or 1.59 mg; 1 or 3 mM final concentration, assuming 70% bioavailability), or XB154 (4 or 20 μg; 1 or 5 μM final concentration, assuming 70% bioavailability) or treated with a test compound (5 mg/kg each week or 10 mg/kg each week). Treatment continues for three weeks, during which time mouse weight and tumor volume are measured as above.

shLSD1 LNCaP cells or control cells are injected in nude mice as above. After three weeks, mice are treated with 2.6 μg mitomycin C (predicted final concentration of 1 μM assuming 40% bioavailability), olaparib (for example, about 0.5 mg/kg to 25 mg/kg), or vehicle intraperitoneally once per day for three weeks. In other examples, unmodified LNCaP cells are injected in nude mice as above.

After three weeks, mice are treated with test compounds, or vehicle as above, plus MMC or olaparib. Treatment continues for three weeks, during which time mouse weight and tumor volume are measured as above.

A decrease in tumor volume compared to control in mice injected with shLSD1 cells indicates that LSD1 inhibition decreases tumor growth in vivo.

Similarly, a decrease in tumor volume compared to control in mice injected with LNCaP cells and treated with a compound disclosed herein indicates that LSD1 inhibition decreases tumor growth in vivo. Finally, a decrease in tumor volume in mice injected with LNCaP cells and treated with a compound disclosed herein plus olaparib as compared to mice treated with a compound disclosed herein alone indicates that inhibition of LSD1 plus inhibition of PARP decreases tumor growth in vivo.

The harvested xenograft tissue is examined for evidence of LSD1 inhibition. This is assessed with Western blots to examine global levels of the 2MK4 and 2MK9 histone marks, expression of FA/BRCA genes, FANCD2 ubiquitination, and LSD1 protein levels in the cases of the shRNA cells. A decrease in one or more of these parameters indicates the effective inhibition of LSD 1. Additionally, effects on DNA damage repair are assessed with staining for H2AX foci.

III. Preparation of Pharmaceutical Dosage Forms

Example 1: Oral Tablet

A tablet is prepared by mixing 48% by weight of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A method for treating cancer selected from the group consisting of acute myeloid leukemia (AML), breast cancer, and prostate cancer in a subject in need thereof comprising administering to the subject a therapeutically effective dose of a compound of Formula (I), or a pharmaceutically acceptable salt thereof:

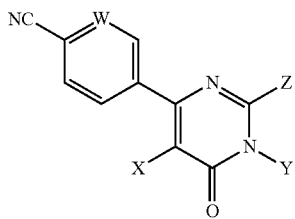

wherein:

W is N, C—H, or C—F;

Y is hydrogen, optionally substituted alkyl, optionally substituted cycloalkyl, or optionally substituted cycloalkylalkyl; and (i) X is hydrogen, halogen, —CN, optionally substituted alkyl, optionally substituted alkynyl, optionally substituted carbocyclylalkynyl, or optionally substituted heteroaryl; and Z is an optionally substituted group chosen from alkyl, carbocyclyl, C-attached heterocyclyl, N-attached heterocyclyl, heterocyclylalkyl, heterocyclylalkenyl, —O-heterocyclyl, —N(R)-heterocyclyl, —O-heterocyclylalkyl, —N(R)-heterocyclylalkyl, —N(R)($C_1$-$C_4$alkylene)-$NR_2$, or —O($C_1$-$C_4$alkylene)-$NR_2$; wherein R is hydrogen or $C_1$-$C_4$alkyl; or (ii) X is optionally substituted aryl; and Z is an optionally substituted group chosen from C-attached heterocyclyl, heterocyclylalkyl, heterocyclylalkenyl, —O-heterocyclyl, —N(R)-heterocyclyl, —O—heterocyclylalkyl, —N(R)-heterocyclylalkyl, —N(R)($C_1$-$C_4$alkylene)-$NR_2$, or —O($C_1$-$C_4$alkylene)-$NR_2$; wherein R is hydrogen or $C_1$-$C_4$alkyl.

2. The method of claim 1, wherein the cancer is acute myeloid leukemia (AML).

3. The method of claim 1, wherein the cancer is breast cancer.

4. The method of claim 1, wherein the cancer is prostate cancer.

* * * * *